(12) United States Patent
Capelli et al.

(10) Patent No.: US 12,097,162 B2
(45) Date of Patent: Sep. 24, 2024

(54) SYSTEMS, DEVICES, AND METHODS OF TREATING TISSUE AND CELLULITE BY NON-INVASIVE ACOUSTIC SUBCISION

(71) Applicant: SOLITON, INC., Houston, TX (US)

(72) Inventors: Christopher C. Capelli, Houston, TX (US); David W. Robertson, Houston, TX (US)

(73) Assignee: SOLITON, INC., Houston, TX (US)

( * ) Notice: Subject to any disclaimer, the term of this patent is extended or adjusted under 35 U.S.C. 154(b) by 277 days.

(21) Appl. No.: 17/601,276

(22) PCT Filed: Apr. 2, 2020

(86) PCT No.: PCT/US2020/026425
§ 371 (c)(1),
(2) Date: Oct. 4, 2021

(87) PCT Pub. No.: WO2020/206146
PCT Pub. Date: Oct. 8, 2020

(65) Prior Publication Data
US 2022/0218562 A1 Jul. 14, 2022

Related U.S. Application Data

(60) Provisional application No. 62/892,973, filed on Aug. 28, 2019, provisional application No. 62/829,026, filed on Apr. 3, 2019.

(51) Int. Cl.
*A61B 8/00* (2006.01)
*A61H 9/00* (2006.01)
(Continued)

(52) U.S. Cl.
CPC ......... *A61H 23/008* (2013.01); *A61H 9/0057* (2013.01); *A61H 23/02* (2013.01);
(Continued)

(58) Field of Classification Search
CPC .................. A61H 23/008; A61H 23/02; A61H 2201/0188; A61H 2201/0214; A61H 2201/1238
See application file for complete search history.

(56) References Cited

U.S. PATENT DOCUMENTS

| | | |
|---|---|---|
| 3,234,429 A | 2/1966 | Schrom |
| 3,364,708 A | 1/1968 | Padberg |

(Continued)

FOREIGN PATENT DOCUMENTS

| | | |
|---|---|---|
| CN | 1245410 | 2/2000 |
| CN | 101028525 | 9/2007 |

(Continued)

OTHER PUBLICATIONS

English translation of Office Action issued in Japanese Patent Application No. 2021- 184610, dated Nov. 18, 2022.

(Continued)

*Primary Examiner* — Joel F Brutus
(74) *Attorney, Agent, or Firm* — Mintz, Levin, Cohn, Ferris, Glovsky and Popeo, P.C.

(57) ABSTRACT

Embodiments of the present disclosure are directed to systems, devices, and methods of inducing physical effects in tissue, such as dermis, adipose, musculoskeletal, vascular, hepatic tissue, using unfocused or planar, non-cavitating acoustic shock waves. The physical effects include disruption of fibrous extracellular matrix of the targeted tissues. Embodiments of the present disclosure include applying rapid acoustic pulses (e.g., shock waves) to cause a breakdown in the fibrous extracellular matrix to reduce the appearance of cellulite or scars in a treatment area. Such unfocused or planar, non-cavitating acoustic shock waves may induce a tissue reaction, such as reduction of fibrosis, induction of angiogenesis, or lymphangiogenesis.

20 Claims, 31 Drawing Sheets

(51) Int. Cl.
*A61H 23/00* (2006.01)
*A61H 23/02* (2006.01)
(52) U.S. Cl.
CPC ............ *A61H 2201/0188* (2013.01); *A61H 2201/0214* (2013.01); *A61H 2201/1238* (2013.01); *A61H 2201/5056* (2013.01); *A61H 2201/5071* (2013.01); *A61H 2201/5092* (2013.01); *A61H 2207/00* (2013.01)

(56) References Cited

U.S. PATENT DOCUMENTS

| | | |
|---|---|---|
| 3,475,646 A | 10/1969 | Chapman |
| 3,604,641 A | 9/1971 | Wilson et al. |
| 3,613,069 A | 10/1971 | Cary |
| 3,735,764 A | 5/1973 | Balev |
| 3,769,963 A | 11/1973 | Goldman |
| 3,942,531 A | 3/1976 | Hoff |
| 3,983,749 A | 10/1976 | Fletcher et al. |
| 4,005,314 A | 1/1977 | Zinn |
| 4,311,147 A | 1/1982 | Hausler |
| 4,715,376 A | 12/1987 | Nowacki et al. |
| 4,858,597 A | 8/1989 | Kurtze et al. |
| 4,896,673 A | 1/1990 | Rose et al. |
| 4,905,671 A | 3/1990 | Senge |
| 4,928,671 A | 5/1990 | Reichenberger et al. |
| 4,955,143 A | 9/1990 | Hagelauer |
| 4,962,752 A | 10/1990 | Reichenberger et al. |
| 4,979,501 A | 12/1990 | Valchanov et al. |
| 5,009,232 A | 4/1991 | Hassler et al. |
| 5,015,929 A | 5/1991 | Cathignol et al. |
| 5,071,422 A | 12/1991 | Watson et al. |
| 5,146,912 A | 9/1992 | Eizenhoefer |
| 5,149,406 A | 9/1992 | Mullen et al. |
| 5,150,713 A | 9/1992 | Okazaki |
| 5,193,527 A | 3/1993 | Schafer |
| 5,195,508 A | 3/1993 | Muller et al. |
| 5,204,820 A | 4/1993 | Strobel et al. |
| 5,231,976 A | 8/1993 | Wiksell |
| 5,240,005 A | 8/1993 | Viebach |
| 5,245,988 A | 9/1993 | Einars et al. |
| 5,259,368 A | 11/1993 | Wiksell |
| 5,269,292 A | 12/1993 | Granz et al. |
| 5,284,143 A | 2/1994 | Rattner |
| 5,304,170 A | 4/1994 | Green |
| 5,304,207 A | 4/1994 | Stromer |
| 5,327,890 A | 7/1994 | Matura et al. |
| 5,360,447 A | 11/1994 | Koop |
| 5,374,236 A | 12/1994 | Hassler |
| 5,393,296 A | 2/1995 | Rattner |
| 5,409,446 A | 4/1995 | Rattner |
| 5,419,327 A | 5/1995 | Rohwedder et al. |
| 5,423,803 A | 6/1995 | Tankovich et al. |
| 5,435,304 A | 7/1995 | Oppelt et al. |
| 5,458,652 A | 10/1995 | Uebelacker |
| 5,509,200 A | 4/1996 | Frankeny et al. |
| 5,529,572 A | 6/1996 | Spector |
| 5,595,178 A | 1/1997 | Voss et al. |
| 5,618,275 A | 4/1997 | Bock |
| 5,658,239 A | 8/1997 | Delmenico |
| 5,675,495 A | 10/1997 | Biermann et al. |
| 5,676,159 A | 10/1997 | Navis |
| 5,709,676 A | 1/1998 | Alt |
| 5,722,411 A | 3/1998 | Suzuki |
| 5,737,462 A | 4/1998 | Whitehouse et al. |
| 5,790,305 A | 8/1998 | Marcellin-Dibon et al. |
| 5,827,204 A | 10/1998 | Grandia et al. |
| 6,013,122 A | 1/2000 | Klitzman et al. |
| 6,036,661 A | 3/2000 | Schwarze et al. |
| 6,039,694 A | 3/2000 | Larson |
| 6,058,932 A | 5/2000 | Hughes |
| 6,080,119 A | 6/2000 | Schwarze et al. |
| 6,096,029 A | 8/2000 | O'Donnell, Jr. |
| 6,113,559 A | 9/2000 | Klopotek |
| 6,113,560 A | 9/2000 | Simnacher |
| 6,123,679 A | 9/2000 | Lafaut et al. |
| 6,176,839 B1 | 1/2001 | Deluis et al. |
| 6,186,963 B1 | 2/2001 | Schwarze et al. |
| 6,210,329 B1 | 4/2001 | Christmas |
| 6,217,531 B1 | 4/2001 | Reitmajer |
| 6,309,355 B1 | 10/2001 | Cain et al. |
| 6,325,769 B1 | 12/2001 | Klopotek |
| 6,350,245 B1 | 2/2002 | Cimino |
| 6,368,929 B1 | 4/2002 | Hill et al. |
| 6,390,995 B1 | 5/2002 | Ogden et al. |
| 6,450,979 B1 | 9/2002 | Miwa et al. |
| 6,454,713 B1 | 9/2002 | Ishibashi et al. |
| 6,487,447 B1 | 11/2002 | Weimann et al. |
| 6,491,685 B2 | 12/2002 | Visuri |
| 6,500,141 B1 | 12/2002 | Irion et al. |
| 6,515,842 B1 | 2/2003 | Hayworth et al. |
| 6,519,376 B2 | 2/2003 | Biagi et al. |
| 6,551,308 B1 | 4/2003 | Muller et al. |
| 6,666,834 B2 | 12/2003 | Restle et al. |
| 6,755,821 B1 | 6/2004 | Fry |
| 6,800,122 B2 | 10/2004 | Anderson et al. |
| 6,905,467 B2 | 6/2005 | Bradley |
| 6,942,663 B2 | 9/2005 | Vargas et al. |
| 6,948,843 B2 | 9/2005 | Laugharn et al. |
| 6,972,116 B2 | 12/2005 | Brill et al. |
| 7,189,209 B1 | 3/2007 | Ogden et al. |
| 7,250,047 B2 | 7/2007 | Anderson et al. |
| 7,311,678 B2 | 12/2007 | Spector |
| 7,364,554 B2 | 4/2008 | Bolze et al. |
| 7,405,510 B2 | 6/2008 | Kaminski et al. |
| 7,470,240 B2 | 12/2008 | Schultheiss et al. |
| 7,507,213 B2 | 3/2009 | Schultheiss et al. |
| 7,544,171 B2 | 6/2009 | Schaden et al. |
| 7,588,547 B2 | 9/2009 | Deem et al. |
| 7,867,178 B2 | 1/2011 | Simnacher |
| 7,985,189 B1 | 7/2011 | Ogden et al. |
| 7,988,631 B2 | 8/2011 | Bohris |
| 8,057,408 B2 | 11/2011 | Cain et al. |
| 8,088,073 B2 | 1/2012 | Simnacher et al. |
| 8,092,401 B2 | 1/2012 | Schultheiss |
| 8,102,734 B2 | 1/2012 | Sliwa et al. |
| 8,235,899 B2 | 8/2012 | Hashiba |
| 8,257,282 B2 | 9/2012 | Uebelacker et al. |
| 8,298,162 B2 | 10/2012 | Del Giglio |
| 8,323,220 B2 | 12/2012 | Babaev |
| 8,343,420 B2 | 1/2013 | Cioanta et al. |
| 8,357,095 B2 | 1/2013 | Anderson et al. |
| 8,672,721 B2 | 3/2014 | Camilli |
| 8,684,970 B1 | 4/2014 | Koyfman |
| 2002/0009015 A1 | 1/2002 | Laugharn et al. |
| 2002/0193831 A1 | 12/2002 | Smith |
| 2003/0167964 A1 | 9/2003 | Anderson et al. |
| 2003/0233045 A1 | 12/2003 | Vaezy |
| 2004/0006288 A1 | 1/2004 | Spector et al. |
| 2004/0181219 A1 | 9/2004 | Goble et al. |
| 2005/0015023 A1 | 1/2005 | Ein-Gal |
| 2005/0049543 A1 | 3/2005 | Anderson et al. |
| 2005/0150830 A1 | 7/2005 | Laugharn |
| 2006/0036168 A1 | 2/2006 | Liang et al. |
| 2006/0064082 A1 | 3/2006 | Bonutti |
| 2006/0094988 A1 | 5/2006 | Tosaya et al. |
| 2006/0158956 A1 | 7/2006 | Laugharn et al. |
| 2006/0173388 A1 | 8/2006 | Ginter et al. |
| 2006/0184071 A1 | 8/2006 | Klopotek |
| 2006/0200116 A1 | 9/2006 | Ferren et al. |
| 2006/0211958 A1 | 9/2006 | Rosenberg et al. |
| 2007/0016112 A1 | 1/2007 | Schultheiss et al. |
| 2007/0038060 A1 | 2/2007 | Cerwin et al. |
| 2007/0049829 A1 | 3/2007 | Kaminski et al. |
| 2007/0055180 A1 | 3/2007 | Deem et al. |
| 2007/0065420 A1 | 3/2007 | Johnson |
| 2007/0135755 A1 | 6/2007 | Bernabei et al. |
| 2007/0198068 A1 | 8/2007 | Chan et al. |
| 2007/0219760 A1 | 9/2007 | Yang et al. |
| 2007/0239072 A1 | 10/2007 | Schultheiss et al. |
| 2007/0239082 A1 | 10/2007 | Schultheiss et al. |
| 2007/0239084 A1 | 10/2007 | Voss |
| 2007/0249939 A1 | 10/2007 | Gerbi et al. |
| 2008/0009774 A1 | 1/2008 | Capelli et al. |

(56) References Cited

U.S. PATENT DOCUMENTS

| | | | |
|---|---|---|---|
| 2008/0009885 A1 | 1/2008 | Del Giglio | |
| 2008/0021447 A1 | 1/2008 | Davison et al. | |
| 2008/0071198 A1 | 3/2008 | Ogden et al. | |
| 2008/0107744 A1 | 5/2008 | Chu | |
| 2008/0132810 A1 | 6/2008 | Scoseria et al. | |
| 2008/0146971 A1 | 6/2008 | Uebelacker et al. | |
| 2008/0154157 A1 | 6/2008 | Altshuler et al. | |
| 2008/0183200 A1 | 7/2008 | Babaev | |
| 2008/0194967 A1 | 8/2008 | Sliwa et al. | |
| 2008/0195003 A1 | 8/2008 | Sliwa et al. | |
| 2008/0215039 A1* | 9/2008 | Slatkine | A61M 5/425 606/9 |
| 2008/0262483 A1 | 10/2008 | Capelli et al. | |
| 2008/0269163 A1 | 10/2008 | Sostaric | |
| 2008/0269608 A1 | 10/2008 | Anderson et al. | |
| 2008/0319356 A1 | 12/2008 | Cain et al. | |
| 2009/0018472 A1 | 1/2009 | Soltani et al. | |
| 2009/0062644 A1 | 3/2009 | McMorrow et al. | |
| 2009/0099485 A1* | 4/2009 | Sarvazyan | A61N 7/00 601/2 |
| 2009/0275832 A1 | 11/2009 | Gelbart | |
| 2010/0049098 A1 | 2/2010 | Shalgi et al. | |
| 2010/0076349 A1 | 3/2010 | Babaev | |
| 2010/0082019 A1 | 4/2010 | Neev | |
| 2010/0087899 A1 | 4/2010 | Erez et al. | |
| 2010/0168575 A1 | 7/2010 | Hashiba | |
| 2010/0204617 A1 | 8/2010 | Ben-Ezra | |
| 2010/0208467 A1 | 8/2010 | Dross | |
| 2010/0249768 A1 | 9/2010 | Avramenko et al. | |
| 2010/0274161 A1 | 10/2010 | Alhari et al. | |
| 2010/0280420 A1 | 11/2010 | Barthe et al. | |
| 2010/0331741 A9 | 12/2010 | Cioanta et al. | |
| 2011/0034832 A1* | 2/2011 | Cioanta | A61B 17/22012 601/1 |
| 2011/0046523 A1* | 2/2011 | Altshuler | A61N 7/02 601/3 |
| 2011/0087157 A1 | 4/2011 | Cioanta et al. | |
| 2011/0319793 A1 | 12/2011 | Hynynen | |
| 2012/0157892 A1 | 6/2012 | Reitmajer et al. | |
| 2012/0167174 A1 | 6/2012 | Saxena et al. | |
| 2012/0253416 A1 | 10/2012 | Erez et al. | |
| 2012/0271169 A1 | 10/2012 | Coussios et al. | |
| 2012/0310232 A1 | 12/2012 | Erez | |
| 2012/0323147 A1 | 12/2012 | Scheirer | |
| 2012/0330288 A1 | 12/2012 | Clementi et al. | |
| 2013/0018287 A1 | 1/2013 | Capelli | |
| 2013/0046179 A1 | 2/2013 | Humayun | |
| 2013/0046207 A1 | 2/2013 | Capelli | |
| 2013/0345600 A1 | 12/2013 | Katragadda et al. | |
| 2014/0005576 A1 | 1/2014 | Adams | |
| 2014/0094718 A1 | 4/2014 | Feldman | |
| 2014/0228820 A1 | 8/2014 | Blaskowski et al. | |
| 2014/0243715 A1 | 8/2014 | Cioanta et al. | |
| 2014/0243847 A1 | 8/2014 | Hakala et al. | |
| 2014/0257144 A1 | 9/2014 | Capelli et al. | |
| 2014/0276693 A1 | 9/2014 | Altshuler et al. | |
| 2014/0276722 A1 | 9/2014 | Parihar et al. | |
| 2014/0277219 A1 | 9/2014 | Nanda | |
| 2014/0378740 A1 | 12/2014 | Wagner et al. | |
| 2015/0105702 A1 | 4/2015 | Wagner et al. | |
| 2015/0126913 A1 | 5/2015 | Jurna et al. | |
| 2015/0217111 A1 | 8/2015 | Stevenson et al. | |
| 2016/0016013 A1 | 1/2016 | Capelli et al. | |
| 2016/0067139 A1 | 3/2016 | Katragadda et al. | |
| 2016/0143802 A1* | 5/2016 | Tranfaglia | A61H 9/0057 601/6 |
| 2016/0166837 A1 | 6/2016 | Strommer et al. | |
| 2016/0262778 A1 | 9/2016 | Du | |
| 2016/0271419 A1 | 9/2016 | Varghese et al. | |
| 2017/0202514 A1 | 7/2017 | Nousiainen et al. | |
| 2017/0301474 A1 | 10/2017 | Saito | |
| 2017/0348539 A1* | 12/2017 | Schwarz | A61N 1/328 |
| 2018/0078774 A1 | 3/2018 | Strommer et al. | |
| 2018/0116905 A1 | 5/2018 | Capelli et al. | |
| 2018/0221688 A1 | 8/2018 | Cioanta et al. | |
| 2018/0236254 A1 | 8/2018 | Schwarz et al. | |
| 2019/0192873 A1* | 6/2019 | Schwarz | A61F 7/00 |

FOREIGN PATENT DOCUMENTS

| | | |
|---|---|---|
| CN | 101146574 | 3/2008 |
| CN | 101155614 | 4/2008 |
| CN | 100530868 | 8/2009 |
| CN | 101610736 | 12/2009 |
| CN | 102057422 | 5/2011 |
| CN | 102247661 | 11/2011 |
| CN | 105209117 | 12/2015 |
| CN | 105246419 | 1/2016 |
| DE | 3150430 | 7/1983 |
| DE | 3710371 | 10/1988 |
| DE | 60008898 | 1/2005 |
| DE | 102007046902 | 4/2009 |
| EP | 0008647 | 3/1980 |
| EP | 0243650 | 11/1987 |
| EP | 0322473 | 7/1989 |
| EP | 0326620 | 8/1989 |
| EP | 2964326 | 1/2016 |
| EP | 3626307 | 3/2020 |
| FR | 2605874 | 5/1988 |
| GB | 2303552 | 2/1997 |
| JP | 53-111689 | 9/1978 |
| JP | S 61-293447 | 12/1986 |
| JP | 62-192150 | 8/1987 |
| JP | S 63-023775 | 2/1988 |
| JP | S 63-183050 | 7/1988 |
| JP | H01-97995 A | 4/1989 |
| JP | H067365 | 1/1994 |
| JP | H06-505648 | 6/1994 |
| JP | H 08140984 | 6/1996 |
| JP | 8-194079 | 7/1996 |
| JP | 1996-222472 | 8/1996 |
| JP | HO-8224253 | 9/1996 |
| JP | 9-103434 | 4/1997 |
| JP | H 10192289 | 7/1998 |
| JP | H 10328192 | 12/1998 |
| JP | 2003-500126 | 1/2003 |
| JP | 2004526507 | 9/2004 |
| JP | 2005514142 | 5/2005 |
| JP | 2007-000218 | 1/2007 |
| JP | 2009-506870 | 2/2009 |
| JP | 2009-518126 | 4/2009 |
| JP | 2009-527262 | 7/2009 |
| JP | 2009-543614 | 12/2009 |
| JP | 2012-516170 | 7/2012 |
| JP | 2013-537559 | 10/2013 |
| JP | 2014-507990 | 4/2014 |
| JP | 2014-525782 | 10/2014 |
| JP | 2016523602 | 8/2016 |
| JP | 2017-500078 | 1/2017 |
| JP | 61-73644 | 8/2017 |
| KR | 101886863 | 8/2018 |
| RU | 2121812 | 11/1998 |
| RU | 2151559 | 6/2000 |
| TW | 200604017 | 2/2006 |
| TW | I 292341 | 1/2008 |
| TW | I 350249 | 10/2011 |
| WO | WO 91/10227 | 7/1991 |
| WO | WO 2000/071207 | 11/2000 |
| WO | WO 2002/030256 | 4/2002 |
| WO | WO 2004/080147 | 9/2004 |
| WO | WO 2007/067563 | 6/2007 |
| WO | WO 2007/088546 | 8/2007 |
| WO | WO 2007/146988 | 12/2007 |
| WO | WO 2008/052198 | 5/2008 |
| WO | WO 2008/074005 | 6/2008 |
| WO | WO 2008/137942 | 11/2008 |
| WO | WO 2010/086301 | 8/2010 |
| WO | WO 2010/122517 | 10/2010 |
| WO | WO 2011/077466 | 6/2011 |
| WO | WO 2011/091020 | 7/2011 |
| WO | WO 2012/107830 | 8/2012 |
| WO | WO 2013/012724 | 1/2013 |
| WO | WO 2014/138582 | 9/2014 |

(56) References Cited

FOREIGN PATENT DOCUMENTS

| WO | WO 2014/191263 | 12/2014 |
|---|---|---|
| WO | WO 2015/176001 | 11/2015 |
| WO | WO 2017/165595 | 9/2017 |
| WO | WO-2018/017414 A2 | 1/2018 |
| WO | WO 2018/136514 | 7/2018 |

OTHER PUBLICATIONS

Office Action issued in Australian Patent Application No. 2018221251, dated Nov. 10, 2022.
Office Action issued in Australian Patent Application No. 2021201670, dated Jun. 20, 2022.
Office Action issued in U.S. Appl. No. 16/478,611, dated Jun. 30, 2022.
Troilius, "Effective Treatment of traumatic Tattoos with a Q-switched Nd:YAG laser," Lasers Surg. Med., 22:103-108, 1998.
Office Communication issued in U.S. Appl. No. 16/319,509, dated Apr. 10, 2023.
Office Communication issued in U.S. Appl. No. 16/904,125, dated Mar. 23, 2023.
Office Communication issued in U.S. Appl. No. 17/096,932, dated Mar. 28, 2023.
Carlberg, "Upgrading from Stepper to Servo," Yaskawa America Inc., pp. 1-7, 2011.
Manousakas et al., "Development of a system of automatic gap-adjusted electrodes for shock wave generators," Review of Scientific Instruments, 75(11):4811-4819, 2004.
Office Action issued in U.S. Appl. No. 16/478,611, dated Oct. 31, 2022.
Notice of Allowance issued in U.S. Appl. No. 17/648,790, dated Feb. 28, 2023.
Office Communication issued in Japanese Patent Application No. 2018-550349, dated Mar. 7, 2023. (English translation).
Official Action issued in Japanese Patent Application No. 2019-544631, dated Sep. 16, 2022.
Official Action issued in U.S. Appl. No. 13/547,995, dated Sep. 15, 2022.
Official Action issued in U.S. Appl. No. 16/319,509, dated Sep. 20, 2022.
Official Action issued in U.S. Appl. No. 16/486,920, dated Sep. 14, 2022.
English translation of Office Action issued in Korean Patent Application No. 10-2019-7005043 dated Sep. 28, 2022.
Office Action issued in U.S. Appl. No. 16/087,976 dated Oct. 13, 2022.
Baumler et al., Q-Switch Laser and Tattoo Pigments: First Results of the Chemical and Photophysical Analysis of 41 Compounds, Lasers in Surgery and medicine 26:13-21 (2000), pp. 13-21.
Bickle, "Abdominal X Rays Made Easy: Calcification," Student BMJ Volume, Aug. 10, 2002, 727-274.
Boxman, et al., "Handbook of Vacuum Arc Science and Technology: Fundamentals and Applications," Park Ridge, New Jersey: Noyes Publications, pp. 316-319, 1995.
Burov, et al., "Nonlinear Ultrasound: Breakdown of Microscopic Biological Structures and Nonthermal Impact on Malignant Tumor," *Doklady Biochemistry and Biophysics*, 383(3), pp. 101-104. (2002).
Chen et al., "The disappearance of ultrasound contrast bubbles: Observations of bubble dissolution and Cavitation nucleation", Ultrasound in Med. & Biol., vol. 28, No. 6, pp. 793-803, 2002.
Delius, et al., "Biological Effects of Shock Waves: Kidney Haemorrhage by Shock Waves in Dogs—Administration Rate Dependence," Ultrasound Med Biol., 14(8), 689-694, 1988.
Eisenmenger, W. et al., "The First Clinical Results of Wide-Focus and Low-Pressure ESWL" Ultrasound in Med. & Biol., vol. 28, No. 6, pp. 769-774, 2002.
Eisenmenger, Wolfgang, "The Mechanisms of Stone Fragmentation in ESWL", Ultrasound in Med. & Biol., vol. 27, No. 5, pp. 683-693, 2001.

Extended European Search Report Issued in Corresponding European Patent Application No. 20153807.1, dated Jun. 9, 2020.
Falco, "Single-Point Nonlinearity Indicators for the Propagation of High-Amplitude Acoustic Signals," Ph.D. Thesis, Graduate Program in Acoustics, The Pennsylvania State University, University Park, PA, May 2007.
Fernando, "A Nonlinear Computational Method for the Propagation of Shock Waves in aero-Engine Inlets Towards a New Model for Buzz-Saw Noise Prediction," 15$^{th}$ AIAA/CEAS Aerocoustics Conferences (30$^{th}$ AIAA Aeronautics Conference_ May 11-13, 2009, p. 1-18.
Gillitzer, et al., "Low-Frequency Extracorporeal Shock Wave Lithotripsy Improves Renal Pelvic Stone Disintegration an a Pig Model," *BJU Int*, 176, 1284-1288, 2009.
Ho et al., "Laser-Tattoo Removal—A Study of the Mechanism and the Optimal Treatment Strategy via Computer Simulations", Lasers in Surgery and medicine 30:389-391 (2002).
International Preliminary Report on Patentability Issued in Corresponding PCT Application No. PCT/US2017/042122, dated Jan. 22, 2019.
International Search Report and Written Opinion Issued in Corresponding PCT Application No. PCT/US2017/042122, dated Jan. 9, 2018.
International Search Report and Written Opinion Issued in Corresponding PCT Application No. PCT/US14/21746, dated Sep. 12, 2014.
International Search Report and Written Opinion issued in Corresponding PCT Application No. PCT/US2020/026425, dated Sep. 2, 2020.
Kuhn et al., "Impact of extracorporeal shock waves on the human skin with cellulite: A case study of an unique instance", *Clinical Interventions of Aging*, 3(1):201-210, 2008.
Kuperman-Beade et al., "Laser Removal of Tattoos", Am J Clin Dermatol 2001: 2(1):21-25.
Kuzmin et al., "Ultrasonic Cavitational Chemical Technologies", XI Session of the Russian Acoustical Society, Moscow, Nov. 19-23, 2001.
Liu, et al., "Optimized Design of LED Freeform Lens For Uniform Circular Illumination," *Journal of Zhejiang University-Science C*, Computer & Electron, 13(12), 929-936, 2012.
Madbouly, et al., "Slow Versus Fast Shock Wave Lithotripsy Rate for Urolithiasis: A Prospective Randomized Study," *The Journal of Urology*, 173, 127-130, 2005.
Nana, et al., "Application of the Multiple Low-Energy Q-Switched Laser for the Treatment of Tattoos in 21 Cases," China Aesthetic Medicine, 4(21), 621-622, 2012. (English Abstract).
Ng et al., "Therapeutic Ultrasound: Its Application in Drug Delivery", Medicinal Research Reviews, vol. 22, No. 2, 204-223, 2002.
Office Action and Search Report issued in Corresponding Chinese Application No. 201780056472.0, dated Jan. 19, 2022 (English Translation provided).
Office Action Issued in Corresponding Japanese Patent Application No. 2019-012062, dated Jun. 16, 2020.
Ogden et al., Principles of Shock Wave Therapy, Clinical Orthopaedics and Related Research, No. 387, pp. 8-17, 2001.
Partial Supplementary Search Report Issued in Corresponding European Patent Application No. EP18754679.1, dated Jul. 29, 2020.
Reichenberger, "Electromagnetic Acoustic Source for Extracorporeal Generation of Shock Waves in Lithotripsy," Siemens Forsch, 1986, 187-194.
Ross et al., "Comparison of Responses of Tattoos to Picosecond and Nanosecond Q-Switched Neodymium: YAG Lasers" ARCH Dermatol/ vol. 134, Feb. 1998, pp. 167-171.
Schmitz, et al., "Treatment of Chronic Plantar Fasciopathy with Extracorporeal Shock Waves (Review)," *Journal of Orthopaedic Surgery and Research*, 8(1); 31, 2013.
Sheth and Pandya, "Melsama: A comprehensive update (Part I)", *Journal of the American Academy of Dermatology*, 65:689-697, 2011.
Sheth and Pandya, "Melsama: A comprehensive update (Part II)", *Journal of the American Academy of Dermatology*, 65:699-714, 2011.

(56) References Cited

OTHER PUBLICATIONS

Solis et al., "Experimental Nonsurgical Tattoo Removal in a Guinea Pig Model with Topical Imiquimod and Tretinoin", Dermatol Surg. 2002, 28:83-87.
Timko et al., "In Vitro Quantitative Chemical Analysis of Tattoo Pigments", ARCH Dermatol/vol. 137, Feb. 2001, pp. 143-147.
Ushakov, et al., "Impulse Breakdown of Liquids," New York, New York: Springer. 2007.
Varma, S., "Tattoo Ink Darkening of a yellow Tattoo after Q-Switched Laser Treatment", 2002 Blackwell Science Ltd., Clinical and Experimental Dermatology, 27, 461-463.
Vogel, et al., "Shock Wave Emission and Cavitation Bubble Generation by Picosecond and Nanosecond Optical Breakdown in Water," J. Acoust. Soc. Am. 100(1) Jul. 1996.
Wolfrum et al., "Shock wave induced interaction of microbubbles and boundaries", Physics of Fluids, vol. 15, No. 10, Oct. 2003, pp. 2916-2922.
Amore et al. (2018). "Treatment of Dimpling from Cellulite." Plast Reconstr Surg Glob Open 2018, 1-8.
Bae, S. (2017). "Antifibrotic Effects of Vibratory Stimulation." 2017. Clemson University TigerPrints, All Dissertations/1879. 204 pages.
Chandrashekar et al. (2010). "Acne Scar Subcision." J Cutan Aesthet Surg. 2010, 3(2), 125-126.
Chiquet et al. (2003). "How do fibroblasts translate mechanical signals into changes in extracellular matrix production?" Matrix Biology 2003, 22, 73-80.
Howard et al. (1997). "In vitro study of the mechanical effects of shock-wave lithotripsy." Ultrasound in Med. & Biol. 1997, 23(7), 1017-1122.
Joodaki et al. (2018). "Skin mechanical properties and modeling: A review." Proc IMechE Part H: J Engineering in Medicine 2018, 1-21. 22 pages.
Kaminer et al. (2015). "Multicenter Pivotal Study of Vacuum-Assisted Precise Tissue Release for the Treatment of Cellulite." American Soc of Derm Surg 2015, 41(3), 336-47.
Lokhandwalla, M. et al. (2001). "Mechanical haemolysis in shock wave lithotripsy (SWL):II. In vitro cell lysis due to shear." Physics in Medicine and Biology, 46(4), 1245-1264.
Marinković et al. (2013). "Matrices of Physiologic Stiffness Potently Inactivate Idiopathic Pulmonary Fibrosis Fibroblasts." Am. J. Respir. Cell Mol. Biol. 2013, 48, 422-430.
Wang et al. (2007). "Mechanoregulation of gene expression in fibroblasts." Gene. 2007, 391(1-2): 1-15. 29 pages.
Widgerow, A. D. (2011). "Cellular/extracellular matrix cross-talk in scar evolution and control." Wound Rep Reg (2011), 19, 117-133.

* cited by examiner

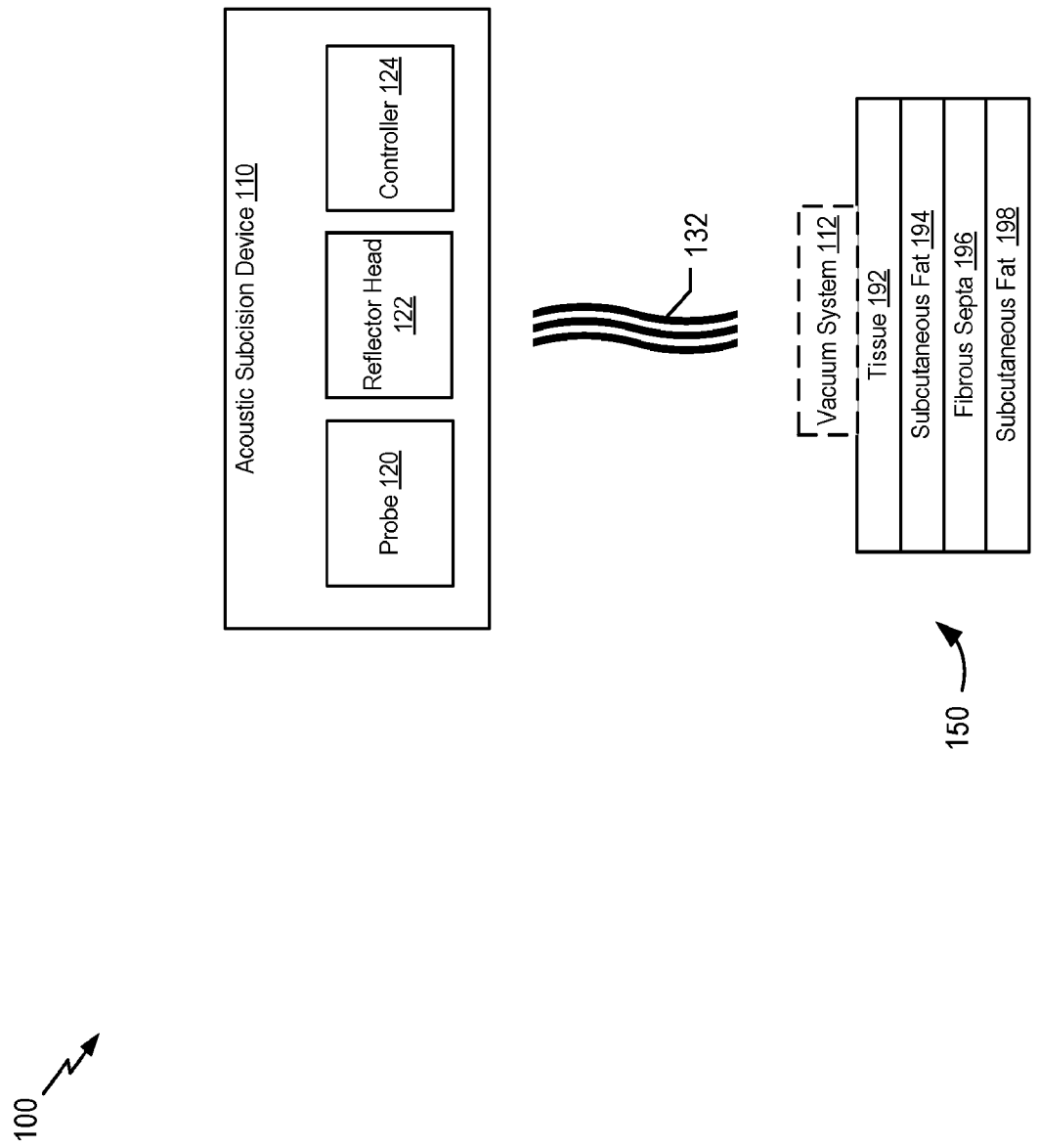

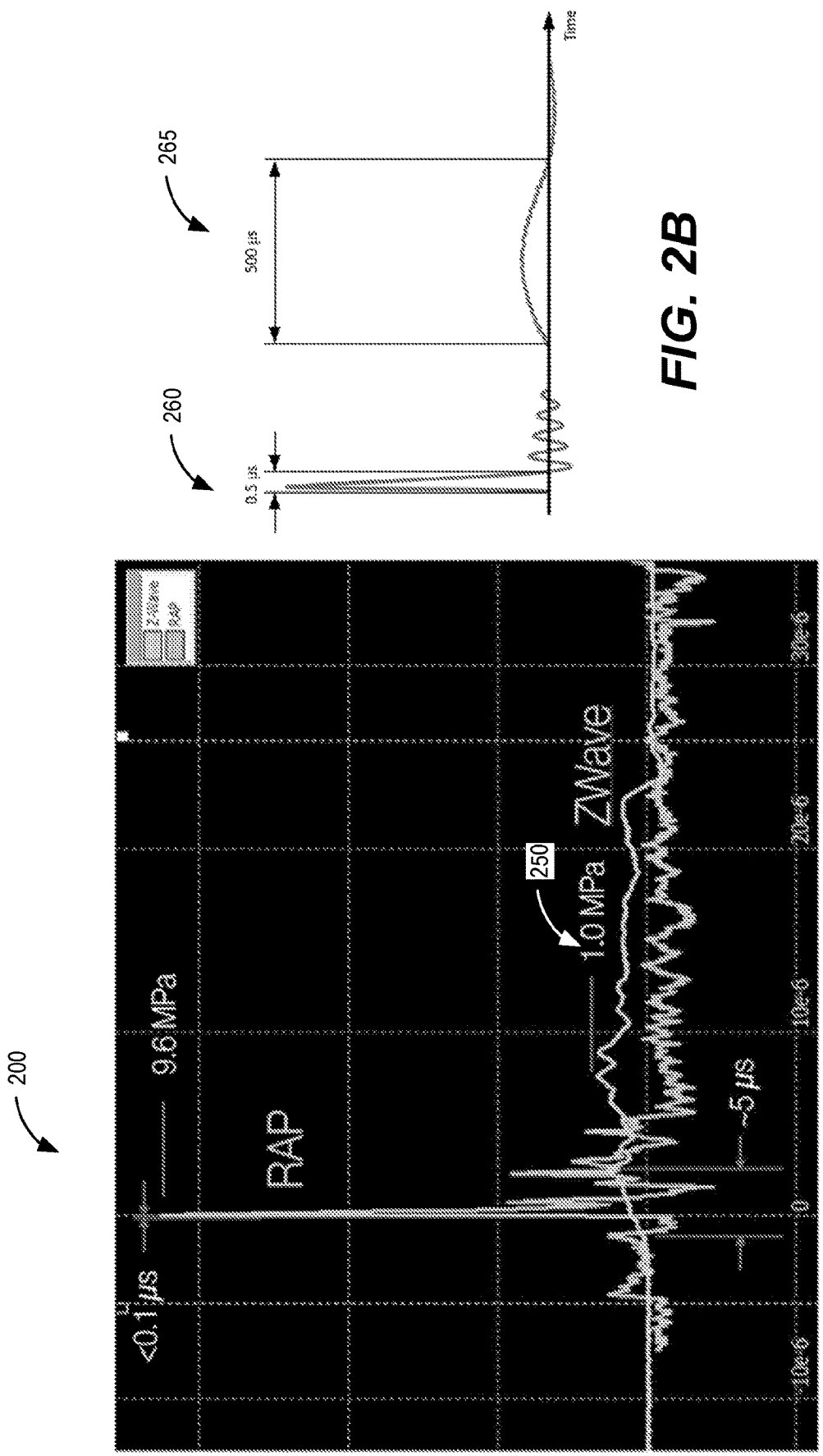
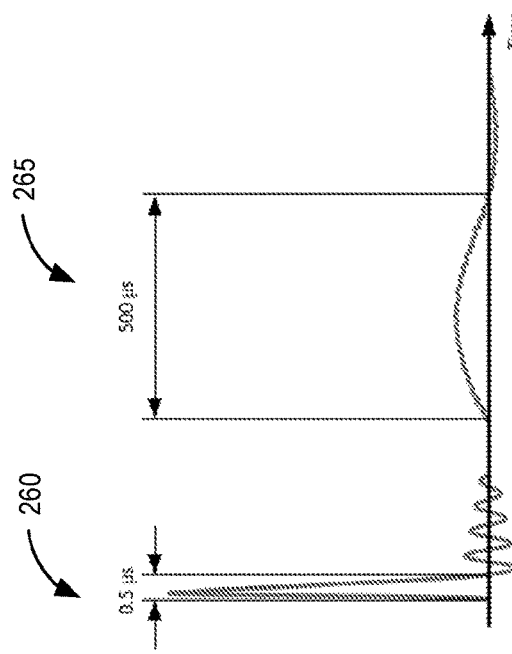
FIG. 2A
FIG. 2B

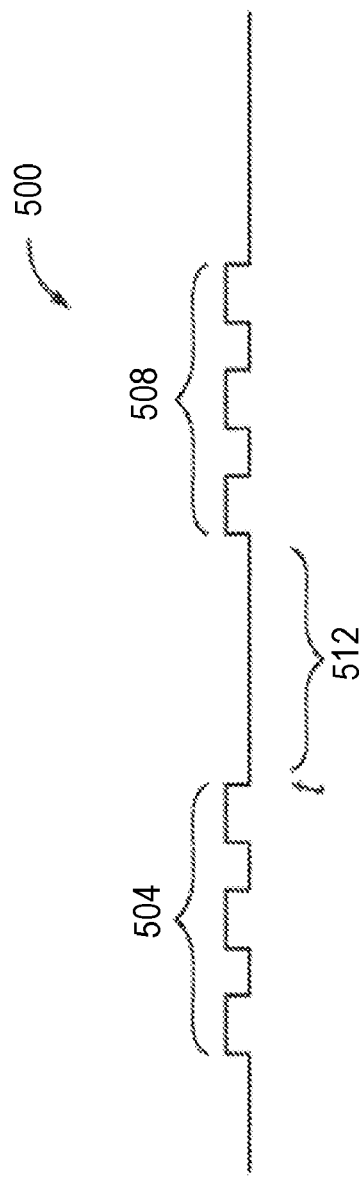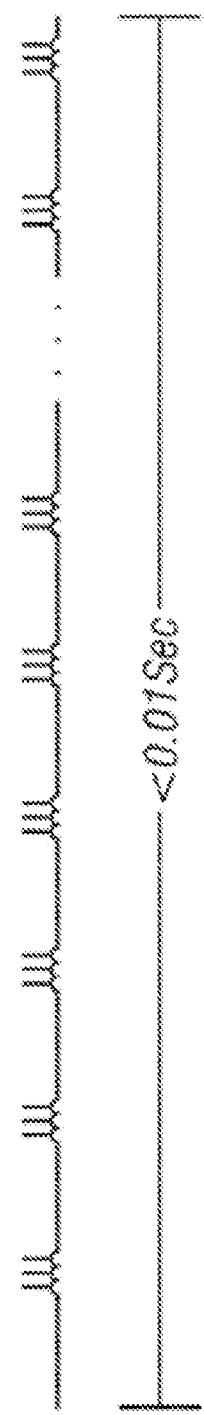

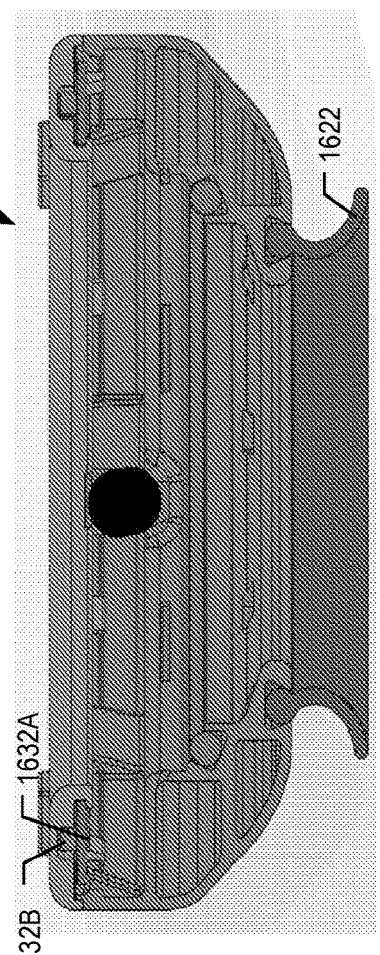
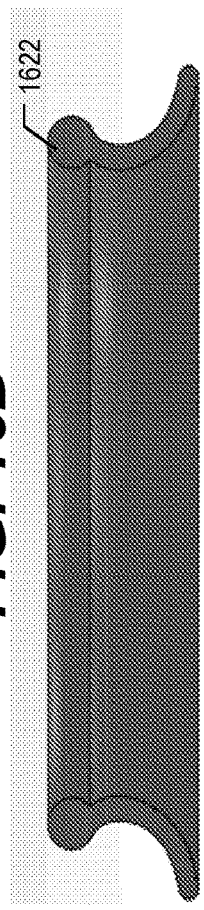
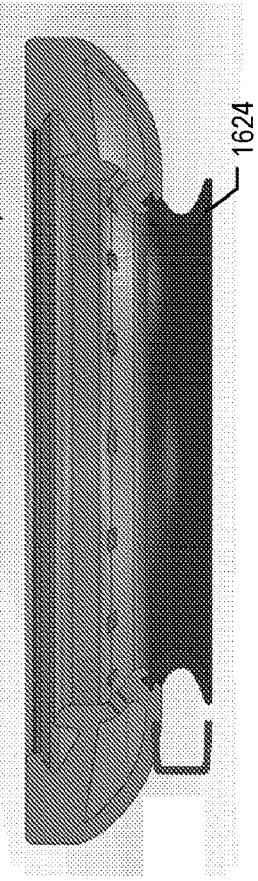
FIG. 16B
FIG. 16D
FIG. 16E
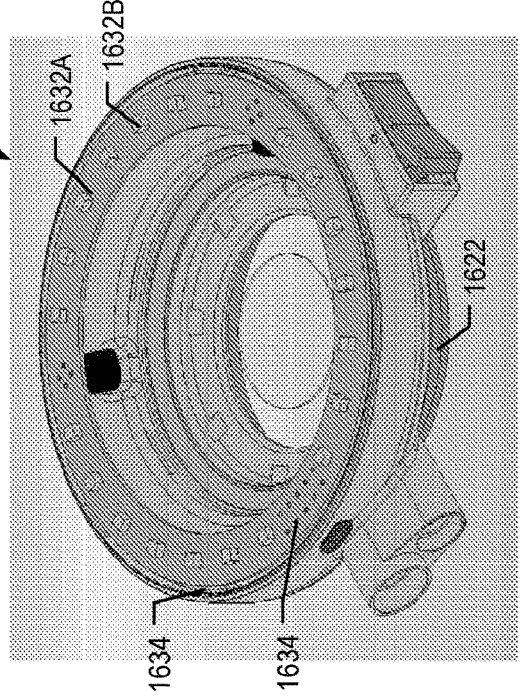
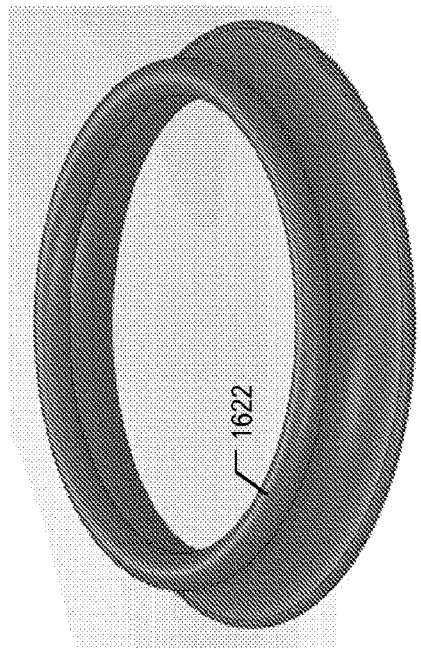
FIG. 16A
FIG. 16C

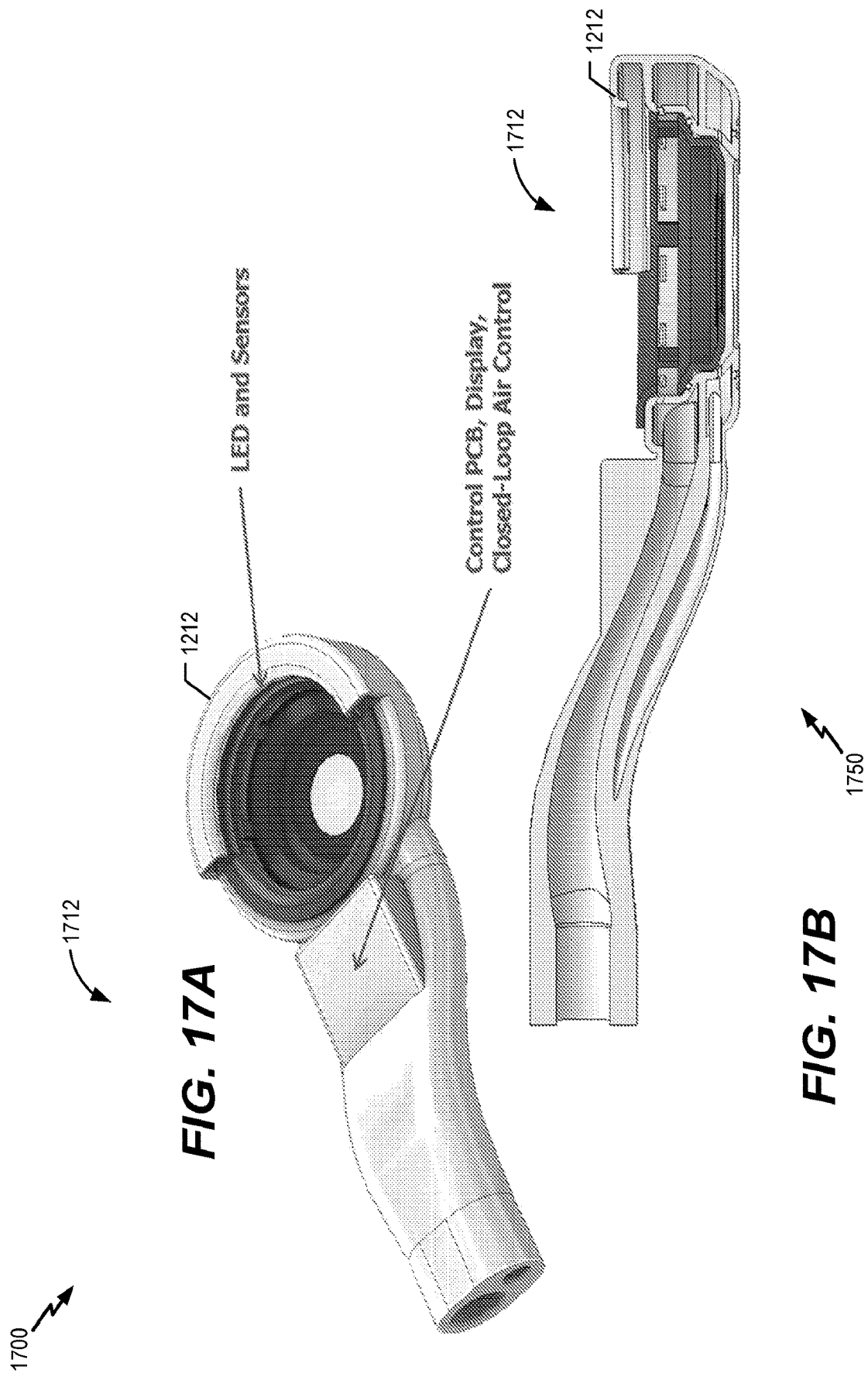

SYSTEMS, DEVICES, AND METHODS OF TREATING TISSUE AND CELLULITE BY NON-INVASIVE ACOUSTIC SUBCISION

CROSS-REFERENCE TO RELATED APPLICATIONS

This application is a national phase application under 35 U.S.C. § 371 of International Application No. PCT/US2020/026425, filed Apr. 2, 2020, which claims the benefit of U.S. Provisional Patent Application No. 62/829,026 filed Apr. 3, 2019 and of U.S. Provisional Patent Application No. 62/892,973 filed Aug. 28, 2019, which are incorporated herein by reference in their entirety.

TECHNICAL FIELD

The present invention relates generally to devices and methods of treatment for tissue and cellulite using shock waves. More particularly, but not by way of limitation, the present invention relates to methods of treatment for causing disruption of fibrous extracellular matrix of the targeted tissues using shock waves.

BACKGROUND

Gynoid lipodystrophy is a localized disorder of the subcutaneous tissue which leads to an alteration in the topography of the skin, for example, a dimpled appearance rather than smooth appearance. This condition, commonly known as "cellulite", commonly appears on the hips, buttocks, and thighs.

Cellulite is formed in the subcutaneous tissue, more specifically, in the subdermal fat layer below the epidermis and dermis layers. In this region, fat cells are arranged in chambers surrounded by bands of fibrous connective tissue called septa (also referred to as trabeculae and include bundles of collagen). Cellulite may be due to the generally parallel orientation of these fibrous structures (e.g., struts), these structures being somewhat perpendicular to the skin. Fat cells held within the perimeters defined by these fibrous structures expand with weight gain and aging, which, for example, stretches the septa and surrounding connective tissue. Eventually this connective tissue contracts and hardens (becomes sclerotic) holding the skin at a non-flexible length, while the chambers between the septa continue to expand, for example, with weight gain, or water gain. This results in areas of the skin being pulled down while adjacent sections bulge outward, resulting in the undesirable lumpy, 'orange peel' or 'cottage cheese' appearance.

Subcision is a surgical procedure used for treating depressed cutaneous scars, wrinkles, and cellulite dimples and ridges. It is also called subcutaneous incisional surgery. Subcision is performed using a special hypodermic needle (e.g., tri-beveled hypodermic needle) inserted through a puncture in the skin surface. The sharp edge of the hypodermic needle is maneuvered under the defect to make subcuticular cuts or "-cisions" to break fibrotic strands that are tethering a skin defect (e.g., scar, wrinkle, or cellulite dimple) to the underlying tissue. The principle of this procedure is to break the fibrotic strands, which tether the scar to the underlying subcutaneous tissue. The defect or depression is lifted by the releasing action of the procedure, as well as from new connective tissue that forms during the course of normal wound healing. As an alternative to performing subcision with a hypodermic needle, a laser (e.g., laser-assisted subcision) can be used to perform subcision. A laser may be inserted into a puncture in the skin surface to have a line of sight to fibrotic strands that are tethering a skin defect so that the laser can apply energy to 'cut' the fibrotic strands with radiation.

By way of example, subcision using tri-beveled hypodermic needle is performed under local anesthesia, such as a topical or infiltration. A number 18 or 20 gauge needles or a Nokor needle (1.5 inch, 18-gauge) are inserted adjacent to the dermal depression with the bevel upwards and parallel to the skin surface and inserted into the deep dermis. The needle is moved back and forth in a fan-like motion under the scar or defect to release fibrous bands at the dermal or deep dermal subcutaneous plane. The needle is removed and the wound is squeezed circumferentially around an exit point to evacuate excess blood and prevent large hematoma formation. A small hematoma is allowed to be formed, which supports the released scar. Hemostasis is maintained with pressure and ice application.

Cutting or relieving of the fibrous septa in the subdermal region by current subcision methods, is labor intensive, time consuming and techniques are highly variable. Bruising and light pain is common for the few days following the procedure and will resolve over time without intervention.

In addition to subcision, a variety of other approaches for treatment of cellulite and removal of unwanted adipose tissue have been proposed. For example, mechanical massage techniques to the affected area have been tried and proposed, with the goal of breaking up lumpy tissue and/or increasing lymphatic drainage in order to smooth the appearance of skin. As another example, application of various topical agents has been proposed with goal of breaking up lumpy tissue and/or increasing collagen. Methods and devices using ultrasound waves to disrupt subcutaneous tissues have also been described. Such methods and devices disrupt other subcutaneous tissues (e.g., tissue and structures other than fibrous septa) by causing biological effects and responses with the goal of inducing a healing response to promote collagen growth.

However, such other approaches rely on different mechanisms, as compared to subcision, to treat cellulite. Specifically, the other approaches do not attempt and have not been shown to be capable of breaking fibrotic strands that are tethering a skin defect (e.g., scar, wrinkle, or cellulite dimple) to the underlying tissue, the process used in subcision. While subcision offers longer lasting results and a capability of treating more advanced cellulite (e.g., Grade 2 cellulite and above) subcision has all the drawbacks that come with a surgical procedure such as pain, anesthesia, healing time, complications, infection risk, etc. For example, the complications include large hematoinas due to bleeding (small heinatomas are normal), pain/tenderness at treated sites, hypertrophic scars (5-10%) or keloid scars, infection, temporary post-inflammatory hyperpigmentation (for which sun protection/avoidance is required), sub-optimal response or lack of improvement, injury to nerves or blood vessels, etc. The healing process can take weeks and painful bruises and/or hematoma formation near treatment sites is common.

Also, subcision is not suitable for a certain patient populations, such as patients with a history of hypertrophic or keloid scars, current or recent (e.g., within 12 months) systemic oral retinoid (e.g., acitretin, isotretinoin, etc.) medications, bleeding or blood clotting disorders (e.g., coagulopathy), active bacterial or viral infections, etc. Thus, current non-invasive techniques are incapable of performing subcision and are not effective at reducing the appearance of advanced cellulite, scars and fibrotic disorders, and current invasive techniques cannot be used on certain patient populations and have significant complications, pain, and recovery times.

Additionally, extracorporeal shock wave therapy (ESWT) has been utilized in clinical medicine for the past four decades for a broad range of indications. The effect of the ESWT on the tissue is thought to be largely mechanistic as a result of cavitation bubbles. Strong forces exerted in the region of a collapsing cavitation bubble causes mechanical disruption or microlesions in the tissue. This tissue disruption leads to a tissue reaction (e.g., healing) such as new blood vessel formation.

Cavitation bubbles form and grow during the trailing negative pressure pulse of the shock wave. When the cavitation bubbles collapses, they generate a flow field, which induces shear stress on the adherent cells in its vicinity. The shear stress is sufficiently strong to break adhesion forces between cells and substrate, destroy cells, or transiently permeabilize cell membranes facilitating molecular uptake.

However, cavitation bubbles can result in painful treatments. ESWT and other focused shock wave therapy produce shock wave induced pain which is usually described as stinging and sharp. Formation, movement, and implosion of the shock wave generated cavitation bubbles in body fluids or tissues that lead to stimulation of the superficial nociceptors in the skin as well as the deeper, visceral nociceptors in the renal capsule, pleura, peritoneum, and muscles which results in pain. Thus, current shock wave therapies are not able to promote tissue reaction and to provide therapy without relying on cavitation and causing pain.

SUMMARY

Embodiments of the present disclosure are directed to systems, devices and methods for disrupting fibrous extracellular matrix of the targeted tissues using high frequency shock waves. In some embodiments, the high frequency shock waves are applied to the skin so as to severe sclerotic (e.g., rigid and unresponsive) fibrous septa in subcutaneous fat. Disruption and/or severing of the fibrous septa in subcutaneous fat can result in an improvement in the appearance of the cellulite on the skin (e.g., smoother skin). Disruption and/or severing of the fibrous septa in subcutaneous fat is a physical effect not produced by conventional acoustic therapy. The high frequency shock waves described herein also produce or cause similar biological effect as conventional acoustic therapy, such as collagenesis, angiogenesis, lymphangiogenesis, and inflammation inhibition. In some embodiments, the applied shock waves are applied at a rate and magnitude such that shock waves are applied to a dermal ridge, dimple, or defect. In some embodiments, the medical and cosmetic methods of treatment can reduce undesired side effects and the total times per treatment (TTPT) relative to known systems. Moreover, the present shock wave therapies can be used non-invasively to greatly reduce complications, reduce time between treatments, and increase patient comfort.

Some embodiments of the present disclosure are directed to systems, devices, and methods of inducing a tissue reaction through the mechanical disruption of the fibrous extracellular matrix of tissue structures using unfocused, non-cavitating, rapid acoustic pulses (RAP) (e.g., acoustic shock wave pulses). Such embodiments of the present disclosure include applying rapid acoustic pulses to cause disruption in tissue structures resulting in a tissue reaction without pain. In a particular embodiment, the tissue reaction is reduction of fibrosis. In another particular embodiment, the tissue reaction is induction of angiogenesis, collagenesis, and or lymphangiogenesis. Such tissue reactions have utility in the treatment of wounds, scars (i.e., keloids, hypertrophic, etc.), implant capsular contractions, fibrotic plaques (e.g., Peyronie's disease), fibrotic organs (e.g., liver fibrosis), etc.

There are two basic effects of acoustic shock waves with the first being characterized as a direct generation of mechanical forces (such as a primary effect from the positive, compressive high pressure rise), and the second being an indirect generation of mechanical forces (e.g., high velocity pressure micro jets) produced by cavitation. Cavitation is a secondary effect from the negative, tensile pressure region of the shock wave. Furthermore, the positive and negative parts/regions of the shock wave work in tandem and have synergetic effects enhancing the acoustic pressure shock waves effects.

In focused acoustic shock waves, cavitation plays a primary role in destroying an outer membrane of pathogens present in the respective tissue conditions or for stimulating tissue regeneration. In focused acoustic shock waves, "In order to have maximum potential for the cavitation phase of focused acoustic pressure shock waves, or radial acoustic pressure waves, or planar acoustic pressure waves, or cylindrical acoustic pressure waves, the repetition rate or frequency is preferably in the range of 1 to 8 Hz." U.S. Patent No. US20180221688A1. Furthermore, the cavitation bubbles need sufficient time to grow to their maximum dimension and then collapse with high speed jets that have velocities of more than 100 m/s. Frequencies higher than 8 Hz are not usually preferable in the treatment of tissue conditions. See U.S. Patent No. US20180221688A1.

As disclosed in U.S. Pat. No. 6,390,995, micro-disruptions resulting from focused shock wave therapy are believed to induce cellular changes, and extracellular matrix and macromolecular changes in a controlled fashion for the purpose of stimulating increased neoangiogenesis, leading to adequate tissue vascularization. The increased circulation and vascularization then induce the body's natural cellular (tissue specific) healing processes. A significant tissue effect is from the cavitation caused by the negative phase of the wave propagation.

However, one problem with focused shock wave therapy is that cavitation bubbles can result in painful treatments. Shock wave induced pain is usually described as stinging and sharp. Formation, movement, and implosion of the shock wave generated cavitation bubbles in body fluids or tissues that lead to stimulation of the superficial nociceptors in the skin as well as the deeper, visceral nociceptors in the renal capsule, pleura, peritoneum, and muscles which results in pain and discomfort for a patient undergoing treatment.

Given the problem caused by cavitation induced pain, many of the beneficial effects from conventional (e.g., focused) shock waves can be obtained through the use of unfocused and/or planar shock waves to provide tissue reactions through the 'microbiology effects' rather than mechanistic effects. Specifically, unfocused and/or planar shock waves can be used to stimulate a cellular response without creating the cavitation bubbles that would result in cellular or tissue damage and treatment pain. The stimulated cells and tissues would then release or produce one or more of the growth factors that accelerate healing. Avoiding the mechanistic effects resulting from cavitation bubbles effectively insures the patient does not have to experience the sensation of pain so common in the focused shock wave forms.

Some embodiments of the present apparatuses (e.g., an acoustic subcision device configured to cause disruption of fibrous structures (dermal and/or subdermal) using rapid acoustic pulses) comprise: a housing; a pulse generation system coupled to the housing; and a controller coupled to the pulse generation system and configured to cause the pulse generation system to generate shock wave pulses, wherein the shock wave pulses are configured to cause disruption of fibrous adipose septa.

In some of the foregoing embodiments of the present apparatuses, the housing defines a chamber and a shock wave outlet, the chamber configured to receive a liquid, and the apparatuses further comprise: a plurality of electrodes configured to be disposed in the chamber to define one or more spark gaps; an acoustic reflector disposed in the chamber; and a single servomotor mechanically coupled to the plurality of electrodes; wherein each of the spark gaps have a spark gap size and a spark gap location, and wherein the single servomotor is configured to adjust each electrode of the plurality of electrodes to maintain a consistent spark gap size and spark gap location.

In some of the foregoing embodiments of the present apparatuses, the acoustic reflector comprises a free-form acoustic reflector. In some implementations, the plurality of electrodes comprises a first electrode and a second electrode; and the single servomotor is mechanically coupled to the first electrode and the second electrode.

In some of the foregoing embodiments of the present apparatuses, the apparatuses further comprise a plurality of pivot arms mechanically coupled to the second electrode. In some implementations, the plurality of pivot arms are configured to advance the second electrode towards the first electrode responsive to the single servomotor being actuated.

In some of the foregoing embodiments of the present apparatuses, the apparatuses further comprise a controller configured to signal the single servomotor via a closed loop control to operate to move the plurality of electrodes and maintain the spark gap at a consistent length. In some implementations, the controller is further configured to signal the single servomotor via the closed loop control, and wherein, to signal the single servomotor, the controller is configured to: measure a pulse time of an electrical discharge of the plurality of electrodes at an identified charge voltage; and signal the single servomotor to move based on the measured pulse time thereby maintaining the spark gap at a consistent length.

In some of the foregoing embodiments of the present apparatuses, the pulse generation system is configured to be coupled to the plurality of electrodes such that the housing is movable relative to the pulse generation system, and that the pulse generation system is in electrical communication with the plurality of electrodes. In some implementations, the acoustic reflector is unitary with the housing. In some of the foregoing embodiments of the present apparatuses, the pulse generation system comprises electrohydraulic (EH) spark heads.

In some of the foregoing embodiments of the present apparatuses, each high frequency wavefront of the shock wave pulses has a rise time of less than 500 ns. In some implementations, each high frequency wavefront of the shock wave pulses has a rise time of less than 100 ns. Additionally, or alternatively, the shock wave pulses have a peak output pressure of 1-20 MPa, 6-20 MPa, 1-30 MPa, or 6-30 MPa.

In some of the foregoing embodiments of the present apparatuses, the acoustic subcision device is configured to output the shock wave pulses at a pulse repetition rate of greater than 10 Hz. In some implementations, the acoustic subcision device is configured to output the shock wave pulses at a pulse repetition rate of greater than 20 Hz.

Some embodiments of the present systems (e.g., an acoustic subcision system configured to cause disruption of fibrous structures using rapid acoustic pulses) comprise: a shock wave generating probe including: a housing; a pulse generation system coupled to the housing; a free-form reflector head coupled to the housing; and a controller coupled to the pulse generation system and configured to cause the pulse generation system to generate shock wave pulses, wherein the shock wave pulses are configured to cause disruption of fibrous adipose septa; and a vacuum head configured to generate negative pressure at a treatment site.

In some of the foregoing embodiments of the present systems, the systems further comprise a vacuum system including: a control unit comprising: a valve; a motor coupled to the valve and configured to adjust the valve; an indicator configured to output an indication corresponding to a position of the valve; and a controller configured to send control signals to the motor and the indicator; a conduit configured to couple to the control unit and to the vacuum head; and the vacuum head comprising: a vacuum head housing defining a window and one or more ports; a compliant member coupled to the vacuum head housing; one or more sensors coupled to the housing; and one or more lights coupled to the vacuum head housing. In some of the foregoing embodiments of the present systems, the controller is integrated with the vacuum head, and the fibrous structures include dermal fibrous structures, sub dermal fibrous structures, or both.

Some embodiments of the present methods of treating a patient to improve an appearance of cellulite using an acoustic subcision device comprise: positioning the acoustic subcision device proximate to a treatment site; and applying a shock wave to the treatment site, wherein the shock wave is configured to cause disruption to fibrous adipose septa. In some of the foregoing embodiments of the present methods, the methods further comprise applying a plurality of shock waves to the treatment site, wherein the plurality of shock waves are applied at a pulse repetition rate of 10 Hz and 200 Hz.

In some of the foregoing embodiments of the present methods, the plurality of shock waves are applied for multiple treatment durations over a treatment session. In some implementations, the treatment site includes multiple treatment locations, and the plurality of shock waves cause disruption of dermal fibrous structures, subdermal fibrous structures, or both.

In some of the foregoing embodiments of the present methods, the methods further comprise: repositioning the acoustic subcision device to a second treatment location of the treatment site; applying second shock waves to the second treatment location; and ceasing a treatment session for the treatment site. In some implementations, the treatment site has an area of 100 $cm^2$. In other implementations, the treatment site has an area of 400 $cm^2$.

In some of the foregoing embodiments of the present methods, a treatment session includes applying one or more treatments to one or more treatment locations of the treatment site, wherein a treatment session is repeated daily, weekly, or monthly.

In some of the foregoing embodiments of the present methods, the methods further comprise locating a dermal ridge within the treatment site, and wherein multiple shock waves are applied to the dermal ridge.

In some of the foregoing embodiments of the present methods, the methods further comprise: positioning a vacuum head on the treatment site; applying the vacuum head to the treatment site; and generating negative pressure at the treatment site. In some implementations, the methods further comprise applying chilled air to the treatment site. Additionally, or alternatively, the methods further comprise removing the vacuum head from the treatment site.

In some of the foregoing embodiments of the present methods, the shock wave is emitted from a free-form acoustic reflector. In some implementations, the free-form acoustic reflector is not parabolic in shape or not parabaloid shaped.

In some of the foregoing embodiments of the present methods, a high frequency wavefront of the shock wave has a rise time of less than 500 ns. In some implementations, a high frequency wavefront of the shock wave has a rise time of less than 250 ns. In some implementations, a high frequency wavefront of the shock wave has a rise time of less than 100 ns. In some of the foregoing embodiments of the present methods, the shock wave has a peak output pressure of 6-30 MPa.

In some of the foregoing embodiments of the present methods, the shock wave has a peak output pressure of 5 MPa, and wherein the acoustic subcision device has a pulse repetition rate of 50 Hz. In some such implementations, a treatment duration for a treatment location of the treatment site is one minute, and wherein a treatment session for the treatment site is twenty minutes. In some such implementations, a treatment duration for a treatment location of the treatment site is two minutes, and wherein a treatment session for the treatment site is twenty-five to fort-five minutes. In a particular implementation, a treatment session for the treatment site is thirty minutes.

In some of the foregoing embodiments of the present methods, the shock wave has a peak output pressure of 10 MPa, and wherein the acoustic subcision device has a pulse repetition rate of 50 Hz. In some such implementations, a treatment duration for a treatment location of the treatment site is two minutes, and wherein a treatment session for the treatment site is twenty minutes.

In some of the foregoing embodiments of the present methods, the shock wave has a peak output pressure of 6 MPa, and wherein the acoustic subcision device has a pulse repetition rate of 100 Hz. In some such implementations, a treatment duration for a treatment location of the treatment site is three minutes, and wherein a treatment session for the treatment site is twenty minutes.

In some of the foregoing embodiments of the present methods, the methods further comprise applying 500 to 60,000 acoustic pulses per treatment location of the treatment site.

Some embodiments of the present methods of treating a patient to improve an appearance of cellulite by causing disruption to fibrous structures using rapid acoustic pulses comprise: identifying a treatment site including cellulite; and applying a series of shock wave pulses to the treatment site.

In some of the foregoing embodiments of the present methods, a treatment area corresponding to the treatment site is within a depth of 0.5-6 cm from an exterior of the treatment site. In some implementations, the treatment site is a buttock, thigh, abdomen, waist, upper arm area, or a portion thereof.

In some of the foregoing embodiments of the present methods, the shock wave pulses correspond to shock waves. In some implementations, the shock wave pulses have a shock wave front of less than 100 ns. Additionally or alternatively, the shock wave pulses have at least 0.015 mJ per $mm^2$ or at least 0.3 mJ per $mm^2$. In some such implementations, the shock wave pulses have between 0.1 mJ per $mm^2$ to 5 mJ per $mm^2$ or between 0.4 mJ per $mm^2$ to 1.5 mJ per $mm^2$. In some implementation, such as when causing disruption of fibrous extracellular matrix structures of tissue, the shock wave pulses have between 0.020 mJ per $mm^2$ to 0.035 mJ per $mm^2$. In a particular implementation, the shock wave pulses have 0.027 mJ per $mm^2$.

In some of the foregoing embodiments of the present methods, the shock wave pulses have pulse repetition rate of at least 10 Hz. In some implementations, the shock wave pulses have pulse repetition rate of between 20 Hz and 1000 Hz.

In some of the foregoing embodiments of the present methods, the shock wave pulses are propagated via a shock wave outlet window that has an area of 0.5 $cm^2$ to 20 $cm^2$. Additionally, or alternatively, the shock wave pulses are substantially planar shock waves.

In some of the foregoing embodiments of the present methods, the shock wave pulses are emitted by a probe including an electrohydraulic wave generator. In some implementations, the probe comprises a fluid-filled chamber and a plurality of electrodes configured to be disposed in the chamber to define one or more spark gaps, wherein the plurality of electrodes are configured to receive voltage pulses from a pulse generation system such that portions of a liquid of the fluid-filled chamber are vaporized to propagate shock waves through the liquid to the shock wave outlet window in contact with treatment site or a vacuum head.

In some of the foregoing embodiments of the present methods, the probe comprises a housing that is configured to receive the plurality of electrodes and to define the fluid-filled chamber, wherein the housing comprises a free-form acoustic reflector surface that defines the chamber. In some implementations, the shock wave pulses are emitted for a treatment time of between 1 to 40 minutes for the treatment site. Additionally, or alternatively, a treatment for the treatment site occurs at least once per two weeks to once per twelve weeks.

Some embodiments of the present systems (e.g., a vacuum system) comprise: a control unit configured to couple to a pump; a conduit configured to couple to the control unit and to a vacuum head; and the vacuum head configured to couple to a treatment site, the vacuum head comprising: a vacuum head housing defining a window and one or more ports; a compliant member coupled to the vacuum head housing; one or more sensors coupled to the vacuum head housing; and one or more lights coupled to the vacuum head housing.

In some of the foregoing embodiments of the present systems, the systems further comprise the pump. In some implementations, the control unit is integrated with the pump, and the vacuum head is configured to assist in acoustic subcision by lifting skin of the tissue site into the vacuum head.

In some of the foregoing embodiments of the present systems, the compliant member comprises a photopolymer flange configured to adhere to a treatment site and create a seal between the treatment site and the vacuum head. In other implementations, the compliant member comprises an overmolded flange configured to adhere to a treatment site and create a seal between the treatment site and the vacuum head. In some such implementations, the photopolymer flange or the overmolded flange has a hardness of 30 Shore A to 50 Shore A.

In some of the foregoing embodiments of the present systems, the one or more sensors are configured to generate data that indicates a vacuum state of the vacuum head.

In some implementations, the one or more lights are configured to illuminate a treatment site, indicate a vacuum state of the vacuum head, or both. Additionally, or alternatively, the one or more sensors include a pressure sensor, an infrared sensor, or both.

In some of the foregoing embodiments of the present systems, the control unit further comprises: a valve; a motor coupled to the valve and configured to adjust the valve; an indicator configured to output an indication corresponding to a position of the valve; and a controller configured to send control signals to the motor and the indicator.

Some embodiments of the present systems (e.g., a vacuum system) comprise: an integrated vacuum device configured to couple to a pump; the integrated vacuum device including: a body defining one or more ports and one or more through channels; and a vacuum head coupled to the body and opposite the one or more ports, the vacuum head comprising: a vacuum head housing defining a window and one or more ports; a compliant member coupled to the vacuum head housing; one or more sensors coupled to the vacuum head housing; and one or more lights coupled to the vacuum head housing. In some of the foregoing embodiments of the present systems, the systems further comprise the pump. Additionally, or alternatively, the vacuum head is configured to assist in acoustic subcision by lifting skin of the tissue site into the vacuum head.

In some of the foregoing embodiments of the present systems, the compliant member comprises a photopolymer flange configured to adhere to a treatment site and create a seal between the treatment site and the vacuum head. In other implementations, the compliant member comprises an overmolded flange configured to adhere to a treatment site and create a seal between the treatment site and the vacuum head. In some such implementations, the photopolymer flange or the overmolded flange has a hardness of 30 Shore A to 50 Shore A.

In some of the foregoing embodiments of the present systems, the one or more sensors are configured to generate data that indicates a vacuum state of the vacuum head.

In some implementations, the one or more lights are configured to illuminate a treatment site, indicate a vacuum state of the vacuum head, or both. Additionally, or alternatively, the one or more sensors include a pressure sensor, an infrared sensor, or both.

In some of the foregoing embodiments of the present systems, the body further includes a control unit comprising: a valve; a motor coupled to the valve and configured to adjust the valve; an indicator configured to output an indication corresponding to a position of the valve; and a controller configured to send control signals to the motor and the indicator.

Some embodiments of the present apparatuses (e.g., an acoustic subcision device) comprise: a housing; a pulse generation system coupled to the housing; and a controller coupled to the pulse generation system and configured to cause the pulse generation system to generate shock wave pulses, wherein the shock wave pulses are configured to cause disruption of fibrous extracellular matrix structures of the tissue.

In some of the foregoing embodiments of the present apparatuses, the shock wave pulses are unfocused and non-cavitating. In some of the foregoing embodiments of the present apparatuses, the shock wave pulses have a negative pulse component of less than 2 microseconds. In some such implementations, wherein the shock wave pulses have a negative pulse component of less than 1 microsecond. In other such implementations, the shock wave pulses have a negative pulse component of less than 0.5 microseconds.

Some embodiments of the present methods (e.g., a method of treating a tissue condition of a human or animal by inducing disruption of tissue structures using non-cavitating rapid acoustic pulses) comprise: identifying a treatment site; and applying a series of shock wave pulses to the treatment site.

In some of the foregoing embodiments of the present methods, the treatment site includes a keloid, a hypertrophic scar, or an implant capsular contraction. In some of the foregoing embodiments of the present methods, the treatment site includes a fibrous plaque. In some of the foregoing embodiments of the present methods, the treatment site includes an fibrotic organ.

In some of the foregoing embodiments of the present methods, the rapid acoustic pulses are unfocused. In some of the foregoing embodiments of the present methods, the rapid acoustic pulses are substantially planar.

In some of the foregoing embodiments of the present apparatuses, the rapid acoustic pulses have a negative pulse component of less than 2 microseconds. In some such implementations, wherein the rapid acoustic pulses have a negative pulse component of less than 1 microsecond. In other such implementations, the rapid acoustic pulses have a negative pulse component of less than 0.5 microseconds.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system or apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the present systems, apparatuses, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Further, a structure (e.g., a component of an apparatus) that is configured in a certain way is configured in at least that way, but it can also be configured in other ways than those specifically described.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

FIG. 1 depicts a block diagram of an example of an acoustic subcision system for providing acoustic subcision treatments to target tissue.

FIG. 2A depicts a waveform that can be emitted by the system of FIG. 1 into target tissue.

FIG. 2B depicts reference waveforms for mechanical waves.

FIGS. 5A-5B depict a timing diagrams of one example of the timed application of energy cycles or voltage pulses in the system of the present acoustic subcision devices.

FIGS. 16A-16E depict additional views illustrating examples of vacuum heads of a vacuum system.

FIGS. 17A and 17B depict two views illustrating an example of an integrated vacuum system of an acoustic subcision system.

FIGS. 20A and 20B depict two photographs of slides illustrating comparisons of fibrous septa.

DESCRIPTION OF ILLUSTRATIVE EMBODIMENTS

Figure 2C:
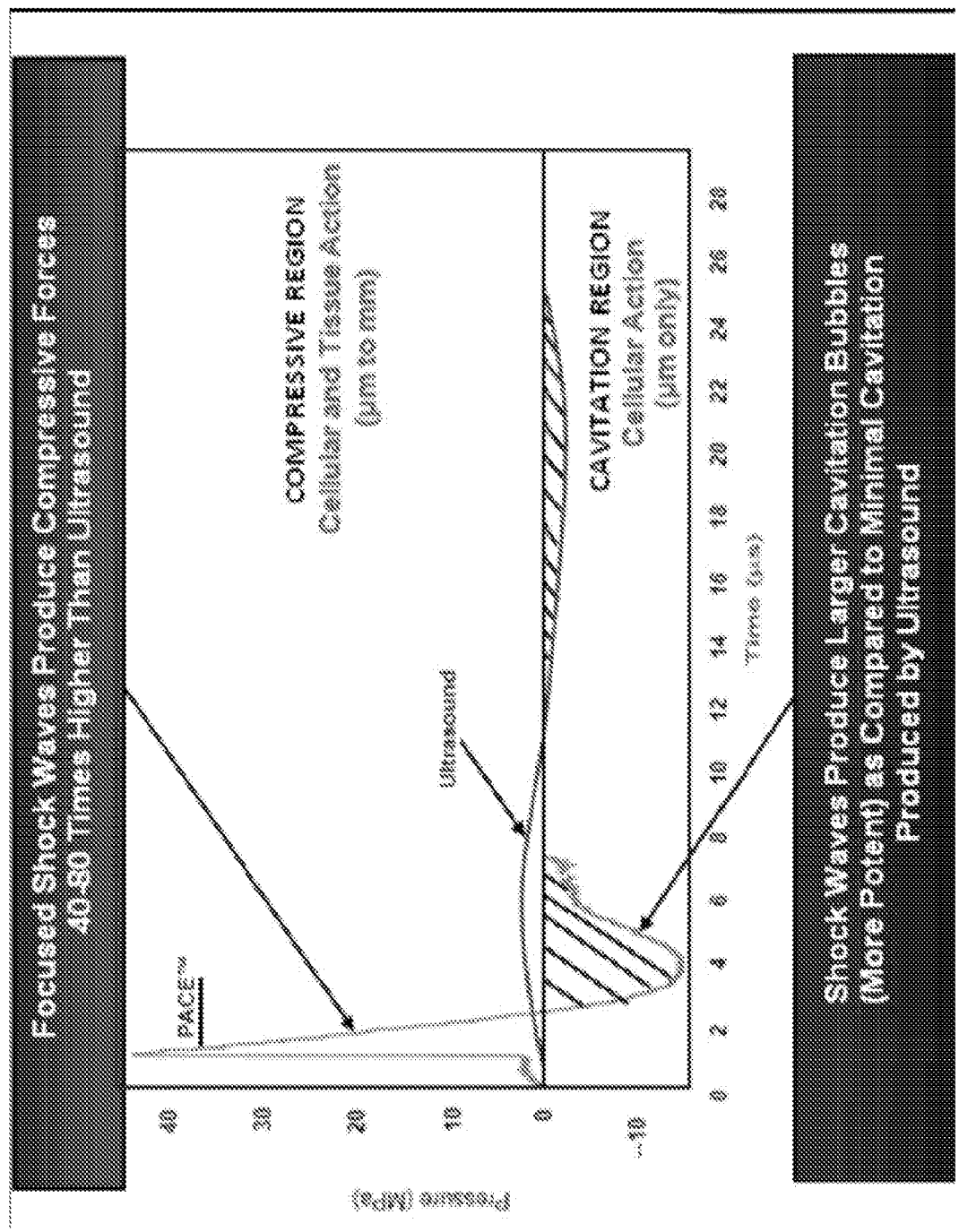
FIG. 2C depicts a comparison between waveforms of focused shock waves and pressure waves.

Embodiments of the present disclosure are directed to systems, devices and methods for disrupting fibrous extracellular matrix structures of targeted tissues using high frequency shock waves. In some embodiments, the high frequency shock waves are applied to the skin so as to severe sclerotic (e.g., rigid and unresponsive) fibrous septa in subcutaneous fat. Disruption and/or severing of the fibrous septa in subcutaneous fat can result in an improvement in the appearance of the cellulite on the skin (e.g., smoother skin). Disruption and/or severing of the fibrous septa in subcutaneous fat is a physical effect not produced by conventional acoustic therapy or other non-invasive therapies.

The high frequency shock waves described herein also produce or cause similar biological effects as conventional acoustic therapy, such as collagenesis, angiogenesis, lymphangiogenesis, and inflammation inhibition, etc. In some embodiments, the applied shock waves are applied to a dermal ridge, dimple or defect at a rate and magnitude such that shock waves cause disruption in sclerotic septa corresponding to the dermal ridge, dimple or defect. In some embodiments, the medical and cosmetic methods of treatment can reduce undesired side effects and the total times per treatment (TTPT) relative to known systems. Moreover, the present shock wave therapies can be used non-invasively to greatly reduce complications, reduce time between treatments, and increase patient comfort.

The ability to cause physical effects (disruption) of the fibrous extracellular matrix is dependent on four factors: (1) applied intensity (Pa), (2) the rate of wave pulses (Hz), (3) wave form shape (e.g., wave front rise time and duration (ns)), and (4) duration of exposure. One or more of these factors can be manipulated to cause disruption of fibrous extracellular matrix in subcutaneous fat. Additionally, the ability to induce tissue reaction is dependent on limiting or eliminating cavitation caused by mechanical waves.

In some embodiments of the present devices, an acoustic subcision device is provided that uses high frequency shock waves (i.e., rapid acoustic pulses or (RAP)) transmitted through the skin to disrupt the fibrous structures that cause cellulite and other fibrotic defects. The acoustic subcision device is non-invasive. As a result, anesthesia, risk of infection from puncture wounds, and long-recovery times are eliminated.

In certain embodiments, rapid acoustic pulses include high frequency shock waves at a pulse repetition rate of between 10 Hz and 200 Hz for a duration to deliver greater than 500 to 60,000 acoustic pulses per treatment location. Each high frequency pulse (i.e., a wavefront thereof) has a rise times less than 500 ns and mean peak output pressures between 1 MPa to 50 MPa. In a preferred embodiment, rapid acoustic pulses include high frequency shock waves provided at a pulse repetition rate of between 50 Hz and 100 Hz for a duration to provide greater than 500 to 30,000 acoustic pulses per treatment location with each acoustic wave having a rise times less than 100 ns and mean peak output pressures between 2 MPa to 15 MPa.

The biological effects are as a result of the mechanotransduction where cells convert mechanical signals into cellular biological events, such as gene expression of extracellular matrix components (e.g., collagen) (Wang, Thampatty, Lin, & Im, 2007). When the cells are exposed to a variety of micromechanical stimuli, transmembrane integrins transfer mechanical forces from the extracellular matrix (ECM) to the cytoskeleton. This activates signal transduction cascades, which in turn alter cytoskeletal functions and induce ECM remodeling. (Bae, 2017).

The rapid acoustic pulse waves of this invention are able to induce physical effects in form of disruption (i.e. subcision) of the fibrous structures that make up the extracellular matrix or in the case of subcutaneous tissue, the fibrous septa. These physical effects are caused by the shearing of the fibrous structures.

The high frequency wavefront fast rise time (<500 ns) and high mean peak output pressures (1 MPa to 50 MPa) are used in shear-induced tissue injury. The greater pressure gradient, the more tissue injury occurs. (Lokhandwalla, McAteer, Williams, & Sturtevant, 2001). Importantly, while shock-induced shearing might initiate injury, individual high frequency acoustic waves do not produce sufficient shear to do so. (Freund, Colonius, & Evan, 2007).

To produce enough tissue damage from shearing, multiple acoustic shock waves need to be administered to the treatment site. For example, in a paper by Howard of the mechanical effects of focused shock waves on tissue-mimicking structures, membrane damage is observed to increase progressively as the number of shock waves increases. For example, kidney injury from shock waves during lithotripsy pervade the focal region of the kidney parenchyma after 1000 or 2000 shock waves. (Howard & Sturtevant, 1997)

However, it just not the number of shock waves that are important to affect tissue. For example, if 1000 shock waves are provided to a kidney over a period of hours or days, there will be little if any tissue damage. Therefore, in addition to the number of acoustic pulses, the acoustic pulse rate of which the acoustic pulses are provided to the tissue is a determining factor.

One exemplary reason for this is that human skin is an anisotropic, nonlinear viscoelastic, loading history—dependent material (Jookaki & Panzer, 2018). At a given acoustic pulse repetition rate, the slower the relaxation time for the tissue, the more tissue degradation from cumulative shock-induced shearing ("A cumulative shear mechanism") (Freund, Colonius, & Evan, 2007). Accordingly, when pulses are applied to tissue at a pulse repetition rate slower than the tissue relaxation time, there typically is no cumulated damage. However, if pulses are applied to tissue at a pulse repetition rate that is faster than the tissue relaxation time, membrane damage is observed to increase progressively as the number of shock waves increases (Howard & Sturtevant, 1997).

Surprisingly, the acoustic subcision devices described herein disrupt the fibrous structures through the skin by applying high frequency shock waves at a pulse rate of between 10 Hz and 200 Hz for a duration to deliver greater than 500 to 30,000 acoustic pulses per treatment location, where each high frequency shock wave (e.g., a wavefront thereof) has a rise times less than 500 ns and mean peak output pressures between 1 MPa to 50 MPa. As a result, in one embodiment, meaningful cellulite improvement can occur in a single treatment visit.

In some embodiments, a method of treating a patient to disrupt fibrous septa in subcutaneous fat of a treatment area can comprise: directing a shock wave generating probe (such as probe 38 or 38a described below) to expose an external area of the patient to a series of shock waves, where the shock wave generating probe comprises a shock wave outlet window, where the shock wave generating probe is configured to generate at least 0.01 mJ per $mm^2$ or at least 0.3 mJ per $mm^2$ at the shock wave outlet window. For example, the shock waves can have 0.01, 0.015. 0.02 . . . 0.5, 0.6, 0.8, 0.9, 1, 1.2, 1.4, 1.6, 1.8, 2, 2.2, 2.4, 2.6, 2.8, 3, 3.4, 3.8, 4, 4.4, 4.8, 5, 5.5, 6, 6.5, 7 mJ per $mm^2$, or any value or range therebetween. In some embodiments, the shock wave generating probe is configured to generate or generates between 0.4 mJ per $mm^2$ to 1.5 mJ per $mm^2$. In some embodiments, the shock wave outlet window has an area of 0.5 $cm^2$ to 20 $cm^2$. For example, the outlet window can have an area of at least 0.5, 0.8, 1, 2, 3, 4, 5, 6, 7. 8, 9, 10, 11, 12, 13, 14, 15, 16, 17, 18, 19, 20 $cm^2$, or any value or range therebetween.

In some embodiments, the shock waves are unfocused and substantially planar prior to entering into the treatment area of the patient. In some embodiments, one or more shock waves is directed to a depth at which there is adipose tissue. In some embodiments, one or more shock waves is directed to a depth of targeted tissue.

In some embodiments, the treatment area is a portion of genitals, buttock, thigh, stomach, waist, and/or upper arm area. In some embodiments, the treatment area of subcutaneous fat is within a depth of 0-6 cm from the external area, such as 0.01, 0.05, 0.1, 0.5, 1, 2, 3, 4, 5, 6 cm, or any value or range therebetween. In some embodiments, the treatment area is at a depth of 0.1-4 cm.

In some embodiments, the treatment area is a portion of the peripheral vasculature. In some embodiments, the treatment area of peripheral vasculature is within a depth of 0-6 cm from the external area, such as 0.01, 0.05, 0.1, 0.5, 1, 2, 3, 4, 5, 6 cm, or any value or range therebetween. In some embodiments, the treatment area is at a depth of 0.1-4 CM.

In some embodiments, the treatment area is a portion of the musculoskeletal system. In some embodiments, the treatment area of musculoskeletal system is within a depth of 0-6 cm from the external area, such as 0.01, 0.05, 0.1, 0.5, 1, 2, 3, 4, 5, 6 cm, or any value or range therebetween. In some embodiments, the treatment area is at a depth of 0.1-4 CM.

In some embodiments, the treatment area is a portion of the hepatic portal system. In some embodiments, the treatment area of hepatic portal system is within a depth of 0-6 cm from the external area, such as 0.01, 0.05, 0.1, 0.5, 1, 2, 3, 4, 5, 6, 12, 20 cm, or any value or range therebetween. In some embodiments, the treatment area is at a depth of 0.1-4 CM.

Referring to FIG. 1, a block diagram of an example of an acoustic subcision system 100 is illustrated. In FIG. 1, the acoustic subcision system 100 include an acoustic subcision device 110, and optionally, a vacuum system 112. The acoustic subcision system 100 is configured to apply therapeutic treatments or medical treatments to a tissue site 150 of a patient. The acoustic subcision device 110 is configured to generate and apply a shock wave pulse 132 to the tissue site 150.

The acoustic subcision device 110 includes a probe 120, a reflector head 122, and a controller 124. In FIG. 1, the reflector head 122 and the controller 124 are illustrated as being separate from the probe 120. However, in other implementations, the reflector head 122, the controller 124, or both, may be integral with the probe 120. The probe 120 is configured to generate a shock wave and apply the shock wave to the reflector head 122. The reflector head 122 is configured to focus or distribute the received shock wave to form the shock wave pulse 132 and to direct the shock wave pulse 132 to the tissue site 150. The controller 124 is configured to control, e.g., activate, the probe 120 and optionally adjust the reflector head 122. Additional details of the acoustic subcision device 110 and components thereof are described with reference to FIGS. 3, 4, 6, and 9-11C. The shock wave pulse 132 is further described with reference to FIGS. 2A and 2B.

The vacuum system 112 may include one or more components configured to generate negative pressure, colloquially referred to as a "vacuum." The vacuum system 112 is configured to be applied to tissue site 150 and to "pull" (e.g., create negative pressure or suction that lifts) tissue 192 upwards towards the acoustic subcision device 110 and away from the patient's body. Examples of a vacuum system 112 are described further with reference to FIGS. 12-16B. Although the term vacuum system is used, the vacuum system may be a single device in some implementations.

The vacuum system 112 may increase an efficacy of application of the shock wave pulse 132. For example, the vacuum system 112 may pull the layers of the tissue site 150 away from other parts of the patient's body, such as bone, organs, other tissue, etc. Accordingly, the shock wave pulse 132 may be able to be directed to the layers of tissue site 150 illustrated in FIG. 1, such as 192-198, and the shock wave pulse 132 may dissipate (e.g., spread out) or weaken (reduce in peak output pressure) by the time the shock wave pulse 132 propagates to (e.g., reaches) other parts or portions of the patient's body (e.g., unintended treatment areas, such as bones, internal organs, muscle tissue, etc.).

Tissue site 150 includes tissue 192 (e.g., dermis or skin), subcutaneous fat 194, 198, and fibrous septa 196. As illustrated in FIG. 1, underneath the tissue 192 is one or more layers of subcutaneous fat 194, 198. The subcutaneous fat 194, 198 may be arranged in chambers and separated by the fibrous septa 196.

The acoustic subcision device 110 is configured to cause disruption of the fibrous septa 196 by applying shock wave pulses 132. The pulses 132 (e.g., a plurality of pulses) may be applied according to the diagram of FIGS. 5A and 5B, as described further herein. Accordingly, the acoustic subcision system 100 is configured to non-invasively cause or induce physical effects in the tissue site 150, and the appearance (e.g., a smoothness) of the tissue site 150 is improved.

Referring to FIGS. 2A-2E, FIGS. 2A-2E illustrate waveforms of various types of mechanical waves, such as ultrasound/pressure waves and shock waves. FIGS. 2A-2E each illustrate shock waves and FIGS. 2A-2C also illustrate pressure waves.

RAPs of FIGS. 2A-2E may cause physical effects and promote healing by compressive forces (i.e., positive pressures). RAPs of FIGS. 2A, 2D and 2E may further promote healing by inducing a tissue reaction, such as vascularization, independent of or without the effect of cavitation, which is caused by negative pressures and/or pressure oscillations.

Referring to FIG. 2A, an image of an oscilloscope reading showing a comparison of an RAP, pulse 200, and a non-RAP, waveform 250, overlapped in time. The vertical axis depicts pressure and the horizontal axis depicts time. The units of the vertical axis are in MPa and the units of the horizontal axis are in microseconds.

In FIG. 2A, a waveform of a shock wave, i.e., a pulse 200, that can be emitted from a probe (e.g., 110) and into a volume of tissue is illustrated. The waveform, i.e., a rapid acoustic pulse (RAP), depicted is capable of causing physical effects, i.e., shearing, in tissue. To illustrate, tension induced in the tissue by repeating pulses (e.g. shock waves) cumulatively builds when applied at a rate greater than a relaxation rate of the tissue. Once a threshold tension is reached, the tissue breaks down, i.e., is sheared apart, by the pressure induced by the pulses.

Pulse 200 illustrates one example pulse shape for an impulse generated by the electrohydraulic (EH) spark heads described below. For example, pulse 200 has a high peak output pressure, illustrated as 9.6 MPa, a rapid rise time (or wave front rise time), illustrated as less than 100 nanoseconds (0.1 microseconds), a short duration, illustrated as less than 500 nanoseconds (0.5 microsecond), and a very short ring down period, illustrated as oscillations with minimal negative amplitudes.

Additionally, FIG. 2A depicts an exemplary waveform of a non-RAP acoustic device for comparison, waveform 250. Waveform 250 is a pressure wave and has a peak output pressure of about 1 MPa and a rise time of about 5000 nanoseconds (5 microseconds). Waveform 250 has a non-zero peak output of 1 MPa or less for a relatively long duration, such as 35 plus microseconds.

Referring to FIG. 2B, reference waveforms for a shock wave and a pressure wave are illustrated. A pressure wave and a shock wave are different types of mechanical waves. Each of the different wave types may have different sub-types, such as focused or planar for shock waves and focused or radial for pressure waves. Pulse 200 is an example of an unfocused or planar shock wave and waveform 250 is an example of a radial pressure wave. Planar shock waves (e.g., non-focused, planar shock waves) often have a therapeutic effect in the body at depths of 0.1-5.5 cm. Focused shock waves can have effects at depths of up to 12 cm. Pressure waves often have a therapeutic effect in the body at depths of up to 3 cm.

In some implementations, an energy flux density of planar shock waves, such as pulse 200, is 0.01 to 0.4 mJ/mm$^2$ at a surface of the skin. Additionally, or alternatively, a positive peak output pressure of planar shock waves, pulse 200, is often 30 MPa or less. For reference, focused shock waves can have an energy flux density of 1.5 mJ/mm$^2$ or greater and positive peak pressures of 100 MPa or greater, while radial pressure waves can have an energy flux density of up to 0.3 mJ/mm$^2$ and positive peak pressures of up to 10 MPa.

In FIG. 2B, an exemplary representative RAP pulse 260 (e.g. shock wave pulse such as pulse 200) and an exemplary representative pressure waveform 265 (e.g., pressure wave pulse) are illustrated side by side for alternative illustration and comparison. Pulse 260 illustrates another example pulse shape for an impulse generated by the described electrohydraulic (EH) spark heads described below. In FIG. 2B RAP pulse 260 has a 0.5 microsecond pulse duration time and pressure waveform 265 has a 500 microsecond pulse duration time.

Referring to FIG. 2C, a comparison between a focused shock wave pulse 270 and an ultrasound pressure waveform 275 is illustrated. In FIG. 2C, an exemplary focused shock wave pulse 270 is illustrated which has a relatively large negative pressure amplitude. FIG. 2C illustrates a compression region which promotes cellular and tissue action. The compression region corresponds to a region where the focused shock wave pulse 270 has/induces positive pressure prior to a negative pressure section and ring down. Cellular and tissue action may be induced by compression regions having a duration of microseconds.

FIG. 2C also illustrates a cavitation region which promotes cellular action. The cavitation region corresponds to a region where the focused shock wave pulse 270 has/induces negative pressure following a positive pressure section and prior to ring down. Cellular action may be induced by cavitation regions having a duration of more than 2 microseconds. Similar to pressure waves 250 and 265, ultrasound wave 275 produces cavitation, but it is minimal as compared to focused shock wave pulse 270.

To illustrate, cavitation bubbles begin to form during the trailing negative pressure pulse of a shock wave. Conventional shock waves (including focused shock wave pulse 270) have negative pressure regions that last greater than 2 microseconds which enables cavitation bubbles sufficient time to grow to their maximum dimension. As a result, cavitation bubbles can grow to large sizes before they collapse with great force causing tissue disruption.

Figure 2D:
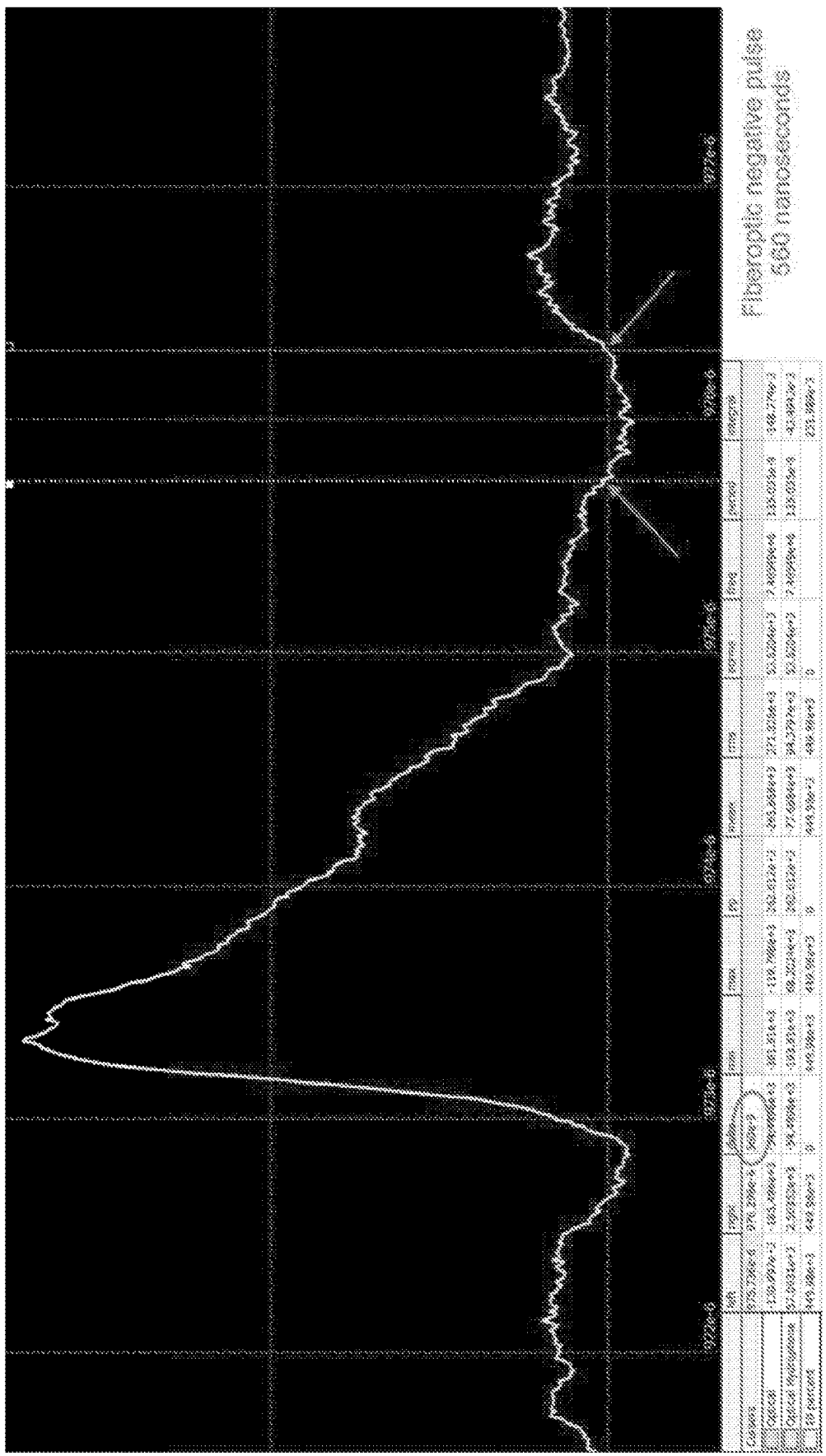
FIG. 2D depicts another waveform that can be emitted by system of FIG. 1 into target tissue.

Referring to FIG. 2D, an exemplary representative compressed RAP pulse 280 with a compressed or reduced negative pulse component. Pulse 280 illustrates another example pulse shape for an impulse generated by the described electrohydraulic (EH) spark heads described below. As compared to focused shock waves, such as 270, and RAPs (e.g., unfocused shock waves), such as 200 and 260, compressed RAP pulse 280 has a compressed negative pressure component, i.e., has reduced amount of time were the pulse has negative pressure and/or a reduced amount of peak negative pressure (MPa).

As illustrated in FIG. 2D, the negative pulse duration (e.g., a duration of the negative pulse component) is 560 nanoseconds (0.560 microseconds). As compared to the negative pulse duration of FIG. 2C, 5 microseconds (5000 nanoseconds), the negative pulse duration of FIG. 2D is reduced. The reduced negative pulse duration greatly reduces cavitation or eliminates cavitation. That is, reduces or eliminates the effects of cavitation on the skin because the limited negative pressure time does not provide sufficient time for the cavitation bubbles to grow to large sizes where their collapse would otherwise cause tissue disruption.

Figure 2E:
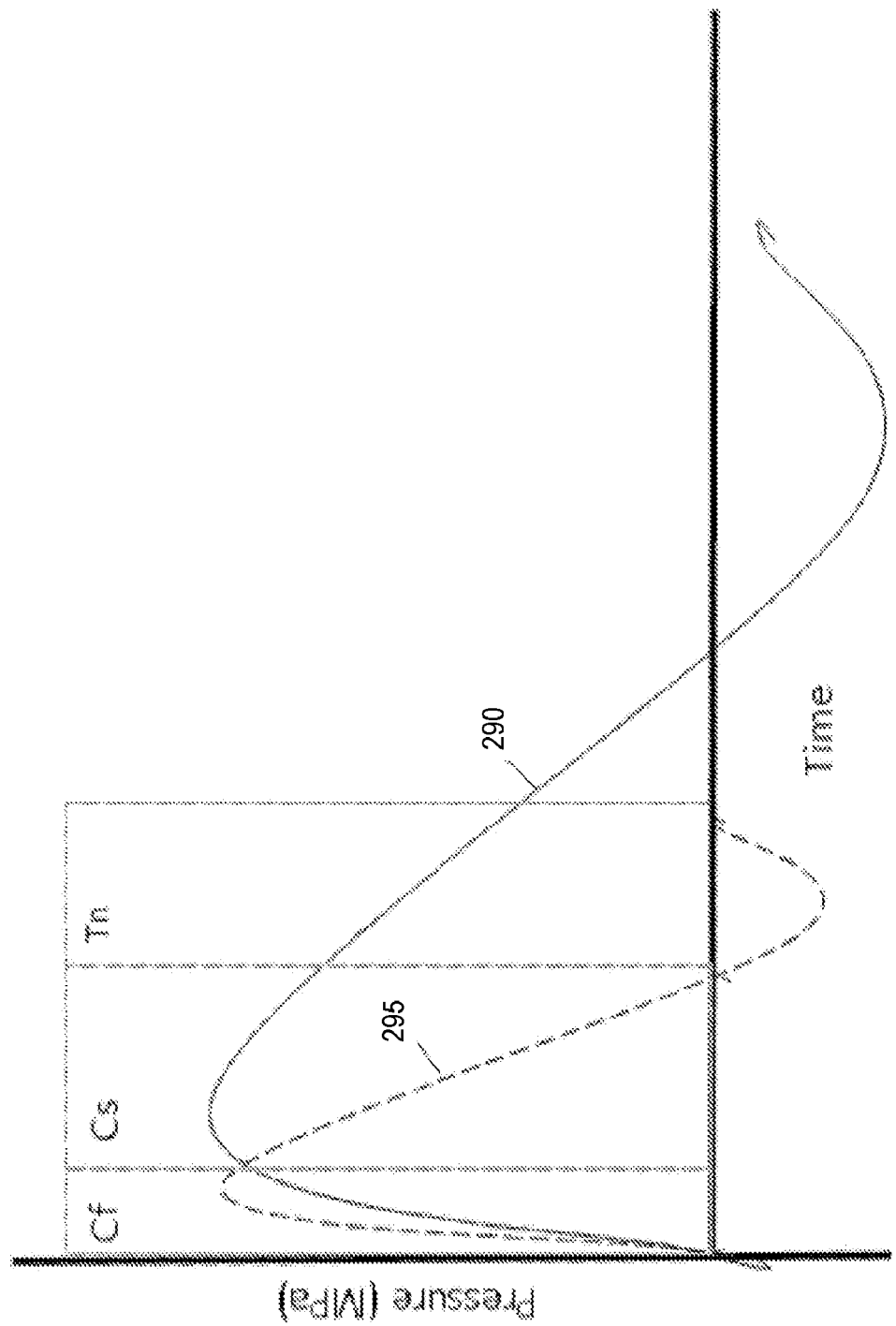
FIG. 2E depicts another waveform that can be emitted by system of FIG. 1 into target tissue.

Referring to FIG. 2E, a comparison between a conventional RAP pulse 290 and a compressed RAP pulse 295 is illustrated to further depict the compression of RAPs described herein as compared to conventional RAPs. Pulse 295 illustrates another example pulse shape for an impulse generated by the described electrohydraulic (EH) spark heads described below. As illustrated in FIG. 2E, the compressed RAP pulse 295 has a shorter overall duration and a faster rise time with similar peak positive pressure, as compared to the conventional RAP pulse 290. Additionally, the compressed RAP pulse 295 has a reduced amount of peak negative pressure, as compared to the conventional RAP pulse 290. Furthermore, the compressed RAP pulse 295 has a reduced or compressed amount of time with negative pressure, as compared to the conventional RAP pulse 290. Specifically, the long duration acoustic tail of the compressed RAP pulse 295 is significantly reduced as compared to the duration of the acoustic tail of the conventional RAP pulse 290. Such a compressed RAP pulse 295 may be generated by a two-stage approach, as described with reference to PCT/US2017/704212.

The compressed RAP pulse 295 is compressed with negative, tensile pressure regions of the shock wave being less than 1 microsecond. As show in FIG. 2E, the trailing negative pressure pulse duration of the compressed RAP pulse 295 is 0.560 microseconds, while the trailing negative pressure pulse duration of the conventional RAP pulse 290 is greater than 2 microseconds. Because the negative, tensile pressure regions of the shock wave are less than one microsecond, the cavitation bubbles may not form at all or may not grow to sufficient size such that the collapse thereof causes tissue damage and pain when compressed RAP pulses 295 are applied.

Compressed RAPs or RAPs with compressed and/or reduced negative pressure components as compared to conventional shock wave pulses, such as 200, 280 and 295, may cause tissue disruption which leads to or promotes a tissue reaction, such as vascularization. Such RAPs, (e.g., 200, 280 and 295), may not cause or induce a cellular reaction, such as cause or induce a cellular action or reaction by cavitation effect. Specifically, the reduced negative pressure and time in which the RAPs described herein have negative pressure reduces cavitation and effects caused thereby. For example, higher levels of cavitation may cause unwanted thermal effects, pain, etc. Thus, the RAPs generated by the acoustic subcision devices described herein are able to induce strong tissue reactions from the mechanical disruption of tissue without cavitation, and thus promote therapeutic use of acoustic waves (e.g., unfocused shock waves) without pain.

One example of a tissue reaction is Fibrosis Reduction. In normal wound healing, myofibroblasts are required for tissue repair. However, in pathologic conditions, activated myofibroblasts become the main or critical effectors of fibrotic disorders. To repair, regenerate, and restore homeostasis after injury, tissue-resident fibroblasts are activated and transform into myofibroblasts (Bae, 2017). In fibrotic disease progression, mechanical stresses in the surrounding microenvironment are a key mediator in the differentiation of myofibroblasts (Bae, 2017).

For fibroblasts and myofibroblasts, mechanical stress can regulate the production of ECM proteins indirectly by stimulating the release of a paracrine growth factor, or directly by triggering an intracellular signaling pathway that activates the genes that produce EMC proteins and growth factors (Chiquet, Renedo, Huber, & Flück, 2003). Focal adhesions at the cellular surface allow mechanical tension generated in the system to be transduced to the cytoskeletal network. These changes create a sensitivity to mechanical tension that transmits to the cell via signaling (e.g., by opening Ca1 channels) to glycoproteins, primarily fibronectin, which acts as ligands attaching to integrins transmitting the signal from the ECM into the cytosol. From the cellular cytoplasm, Smad3, Sma4 signals are stimulated by this tension to form complexes that enter the nucleus initiating TGF-b1 stimulation, procollagen formation, collagen formation, fibroblast differentiation to myofibroblast, and wound contraction with excess collagen III (Widgerow, 2011).

The alteration in the ECM biomechanical properties, stiffness in particular, may be an important therapeutic target that is able to modulate myofibroblast formation and fibrosis (Bae, 2017). Studies suggest that fibroblasts cultured on low modulus substrates can maintain a normal phenotype. However, when cultured on high modulus substrates they are activated to myofibroblasts (Bae, 2017). Importantly, when cultured on a low modulus substrate, the myofibroblast activation was reversable. Marinkovic et al (Marinkovic, Liu, & Tshumperlin, 2013) demonstrated that the contractile and proliferative function in primary fibroblasts derived from fibrotic lungs were significantly inhibited when they were cultured in soft matrices (e.g., about 1 kPa of elastic modulus). Based on these results, the myofibroblast phenotype may not be a permanent state, but can be reversed by alterations in the matrix properties (Bae, 2017) (Marinkovic, Liu, & Tshumperlin,2013). Wang et al (Wang, Haeger, Kloxin, Leinwan, & Anseth, 2012) demonstrated that the fate of porcine aortic valve myofibroblasts in response to reduced substrate modulus showed a decrease in α-smooth muscle actin (α-SMA), stress fibers and proliferation as well as an increase in myofibroblast apoptosis. Furthermore, the levels of gene expression including α-SMA and connective tissue growth factor (CTGF) were significantly up-regulated when valvular myofibroblasts were cultured on stiff substrates (e.g., 32 kPa of elastic modulus, mimicking pre-calcified diseased tissue) (Wang, Haeger, Kloxin, Leinwan, & Anseth, 2012). Based on these results Wang et al (Wang, Haeger, Kloxin, Leinwan, & Anseth, 2012) suggested that the mechanical stiffness of the substrates can regulate the fate of activated myofibroblasts, resulting in a predominantly quiescent fibroblast population (Bae, 2017) (Wang, Haeger, Kloxin, Leinwan, & Anseth, 2012). Mechanically-based antifibrotic therapy can offer several substantial benefits relative to existing pharmaceutical approaches. These benefits include localized/regional as opposed to systemic activity, ease of dose adjustment and discontinuation that will likely offer improved safety and reduced systemic side effects.

The unfocused, non-cavitating, rapid pulse acoustic shock waves described herein when applied to tissue causes a disruption in tissue structures. This disruption of tissue structures results in a loss of mechanical stiffness of these tissue structures. As a result, the activated myofibroblasts found in fibrotic tissue can be pushed into a quiescent or apoptotic state leading to a reduction of fibrosis. The improvement in the appearance of a scar after RAP treatment is believed to be achieved through microscopic disruption of the scar collagen matrix leading to a reduction in the mechanical stiffness of the scar matrix.

This reduction in mechanical stiffness of the scar matrix can result in the myofibroblast being pushed into a quiescent or apoptotic state leading to an improvement in the appearance of the scar. The high pulse rate of the RAP allows non-invasive scar tissue disruption without cavitation damage or thermal degradation of the surrounding tissue, or the pain that is seen with focused acoustic devices.

The unfocused, non-cavitating, rapid acoustic pulses described herein, when applied to fibrotic tissue, can cause a disruption in the fibrotic tissue structures. If the fibrotic tissue is scar tissue, RAP can cause a disruption in the scar tissue structures. Not to be limiting, in one embodiment the scar tissue is in the form of a keloid scar. In another embodiment, the scar tissue is in the form of a hypertrophic scar. In yet another embodiment, the scar tissue is in the form of a tissue adhesion. In still another embodiment, the scar tissue is in the form of a implant capsular contraction.

Another example of a tissue reaction is Angiogenesis Induction. Angiogenesis is a nonspecific response to tissue disruption (i.e. injury). Angiogenesis and neovascularization play a central role during the initial phases of wound healing. This angiogenic response is stimulated by various growth factors released as a result of tissue disruption and inflammatory cell infiltration.

Vascular endothelial growth factor A (VEGF-A) is a signaling protein produced by cells that stimulates the formation of blood vessels. VEGF-A is essential for adults during organ remodeling and diseases that involve blood vessels, for example, in wound healing, tumor angiogenesis, diabetic retinopathy, and age-related macular degeneration.

VEGF-A expression in normal skin is absent. However, mechanical disruption in skin provokes a strong upregulation of VEGF-A expression, which correlates both temporally and spatially with the proliferation of new blood vessels. The end result is seen as increased vascular density in the affected area. It has been theorized, i.e., the 'angiogenic hypothesis', that the release of angiogenic growth factors is a nonspecific response to tissue injury, which can be created by a variety of methods.

The rapid acoustic pulses of this invention when applied to tissue cause a disruption in tissue structures. This tissue disruption can result in the release of angiogenic growth factors leading to the proliferation of new blood vessels.

As a result, the unfocused, non-cavitating, rapid acoustic pulses of this inventions when applied to tissue can cause a disruption in the tissue structures thereby inducing a tissue reaction in the form of new blood vessel formation. Not to be limiting, but in one embodiment the RAP can be used to induce new blood vessel formation in non-healing wounds. In another embodiment, RAP can be used to induce new blood vessel formation in skin. In yet another embodiment, RAP can be used to induce new blood vessel formation in adipose tissue. In yet another embodiment, RAP can be used to induce new blood vessel formation in muscle tissue, such as cardiac muscle tissue. In yet another embodiment, RAP can be used to induce new blood vessel formation in tissue related to reproductive health, such as used in the treatment of erectile dysfunction, in vaginal rejuvenation, etc.

In some embodiments, the shock wave generating probe can emit a shock wave comprising the following waveform characteristics in a transmitting medium. A transmitting medium can be a tissue (e.g., an adipose tissue) or an aqueous solution (e.g., a saline solution, such as one at 0.1-10% concentration). In some embodiments, a shock wave emitted at the outlet window of the probe and/or delivered to the treatment area can have a shock wave front rise time of less than 500 ns, less than 400 ns, less than 300 ns, less than 250 ns, less than 200 ns, less than 100 ns, less than 80 ns, less than 50 ns, or less than 20 ns as measured in a transmitting medium. For example, a shock wave emitted at the outlet window of the probe and/or delivered to the treatment area can have shock wave front rise time of 100 ns, 200 ns, 300 ns, 400 ns, 500 ns, etc. In some embodiments, the actual acoustic pulse amplitude emitted may be 0.5 to 50 MPa.

In some embodiments, the probe emits a shock wave at a pulse repetition rate (also referend to as a pulse rate) of at least 10 Hz. For example, the probe emits a shock wave at a pulse repetition rate of between 10 Hz and 1000 Hz., such as 20, 30, 40, 50, 60, 70, 80 90, 100, 150, 200, 250, 300, 350, 400, 450, 500, 550, 600, 650, 700, 750, 800, 850, 900, 950, 1000 Hz, or any value or range therebetween. In some embodiments, the probe emits a shock wave at a pulse rate of between 10 Hz and 100 Hz. In some embodiments, the probe emits a shock wave at a pulse rate of between 20 Hz and 75 Hz. In some embodiments, the probe emits a shock wave at a pulse rate of between 100 Hz and 500 Hz. In some embodiments, the probe emits a shock wave at a pulse rate of between 500 Hz and 1000 Hz. In some embodiments, the emitted waves are configured according to the characteristics above to induce minimal to no detectable transient cavitation in a transmitting medium.

As a result, the long treatment times seen with the prior art, along with the problems associated with these long treatment times (e.g., office space, costs, discomfort, etc.) can be avoided using this invention. For example, in some embodiments, a treatment session can be 1 to 60 minutes within a 24 hour period. A treatment session can be 1, 2, 4, 5, 8, 10, 12, 15, 18, 20, 22, 24, 26, 28, 30, 40, 45, 60 minutes or any value or within any range therebetween. A treatment session can include multiple treatment applications, such as multiple treatment applications to distinct treatment locations/sites within a treatment area or multiple treatment applications to multiple treatment areas. A treatment location may include or corresponds to a scar, a dermal ridge, a dimple, or cellulite (e.g., Grade 2 cellulite and above). A treatment session can be performed daily, every other day, every three days, weekly, bi-weekly, monthly, bi-monthly, and quarterly. A treatment plan can comprise 1 to 20 sessions within a one-year period, such as 1, 2, 3, 4, 5, 6, 7, 8, 9, 10, 11, 12, 13, 14, 15, 16, 17, 18, 19, 20 sessions or any value therebetween. In some embodiments, a treatment plan comprises a session at least once per two weeks for at least 6 weeks.

As described with reference to FIG. 1, the acoustic submission system 100 includes a shock wave generator. The shock wave generator can be configured to deliver defocused planar waves with the above-described characteristics. In some embodiments, EH waves are generated. For example, the systems and apparatus described in U.S. Patent Publication No. 2014/0257144 can be configured to apply EH shock waves at the described rate, energy level, and duration. In particular, the shock wave generating apparatus can be configured to generate a planar, defocused shock wave front.

Figure 3:
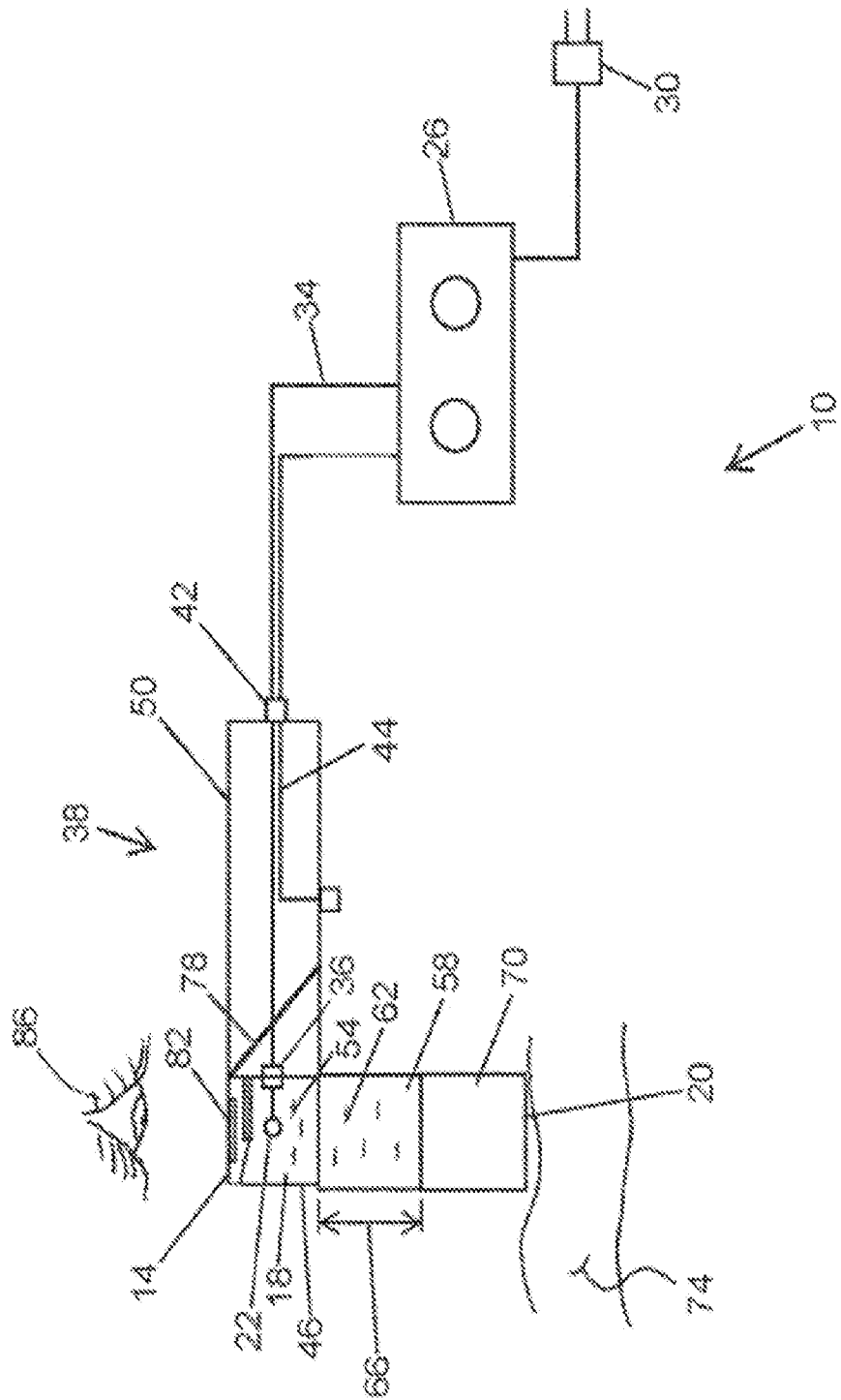
FIG. 3 depicts a block diagram of an example of an electro-hydraulic (EH) shock wave generating acoustic subcision device.

With reference to FIG. 3, such a system can include a handheld probe (e.g., with a first housing, such as in FIG. 4) and a separate controller or pulse-generation system (e.g., in or with a second housing coupled to the handheld probe via a flexible cable or the like). In the embodiment shown, apparatus 10 comprises: a housing 14 defining a chamber 18 and a shock wave outlet 20; a liquid (54) disposed in chamber 18; a plurality of electrodes (e.g., in spark head or module 22) configured to be disposed in the chamber to define one or more spark gaps; and a pulse-generation system 26 configured to apply voltage pulses to the electrodes at a rate of between 10 Hz and 1000 Hz, such as between 10 Hz and 100 Hz, 100 Hz and 500 Hz, or 500 Hz and 1000 Hz. In this embodiment, the pulse-generation system 26 is configured to apply the voltage pulses to the electrodes such that portions of the liquid are vaporized to propagate shock waves through the liquid and the shock wave outlet window.

In the embodiment shown, pulse-generation system 26 is configured for use with an alternating current power source (e.g., a wall plug). For example, in this embodiment, pulse-generation system 26 comprises a plug 30 configured to be inserted into a 110V wall plug. In the embodiment shown, pulse-generation system 26 comprises a capacitive/inductive coil system, on example of which is described below with reference to FIG. 7. In the embodiment shown, pulse-generation system 26 is (e.g., removably) coupled to the electrodes in spark head or module 22 via a high-voltage cable 34, which may, for example, include two or more electrical conductors and/or be heavily shielded with rubber or other type of electrically insulating material to prevent shock. In some embodiments, high-voltage cable 34 is a combined tether or cable that further includes one or more (e.g., two) liquid lumens through which chamber 18 can be filled with liquid and/or via which liquid can be circulated through chamber 18 (e.g., via combined connection 36). In the embodiment shown, apparatus 10 comprises a handheld probe or handpiece 38 and cable 34 is removably coupled to probe 38 via a high-voltage connector 42, which is coupled to spark head or module 22 via two or more electrical conductors 44. In the embodiment shown, probe 38 comprises a head 46 and a handle 50, and probe 38 can comprise a polymer or other electrically insulating material to enable an operator to grasp handle 50 to position probe 38 during operation. For example, handle 50 can be molded with plastic and/or can be coated with an electrically insulating material such as rubber.

In the embodiment shown, a liquid 54 (e.g., a dielectric liquid such as distilled water, or conductive liquid such as saline) is disposed in (e.g., and substantially fills) chamber 18. In this embodiment, spark head 22 is positioned in chamber 18 and surrounded by the liquid such that the electrodes can receive voltage pulses from pulse-generation system 26 (e.g., at a rate of between 10 Hz and 1000 Hz, 10 Hz and 100 Hz, 100 Hz and 500 Hz, or 500 Hz and 1000 Hz) such that portions of the liquid are vaporized and the collapse of the vapor bubble generates a shock wave that will propagate through the liquid and shock wave outlet 20. In the embodiment shown, probe 38 includes an acoustic delay chamber 58 between chamber 18 and outlet 20. In this embodiment, acoustic delay chamber is substantially filled with a liquid 62 (e.g., of the same type as liquid 54) and has a length 66 that is sufficient to permit shock waves to form and/or be directed toward outlet 20. In some embodiments, length 66 may be between 2 millimeters (mm) and 25 millimeters (mm). In the embodiment shown, chamber 18 and acoustic-delay chamber 58 are separated by a layer of sonolucent (acoustically permeable or transmissive) material that permits shock waves to travel from chamber 18 into acoustic-delay chamber 58. In other embodiments, liquid 62 may be different than liquid 54 (e.g., liquid 62 may comprise bubbles, water, oil, mineral oil, and/or the like). Certain features such as bubbles may introduce and/or improve a nonlinearity in the acoustic behavior of liquid 54 to increase the formation of shock waves.

In further embodiments, chamber 18 and acoustic-delay chamber 58 may be unitary (i.e., may comprise a single chamber). In further embodiments, acoustic-delay chamber 58 may be replaced with a solid member (e.g., a solid cylinder of elastomeric material such as polyurethane). In the embodiment shown, probe 38 further includes an outlet member 70 removably coupled to the housing at a distal end of the acoustic delay chamber, as shown. Member 70 is configured to contact an external area located above tissue 74, and can be removed and either sterilized or replaced between patients. Member 70 comprises a polymer or other material (e.g., low-density polyethylene or silicone rubber)

that is acoustically permeable to permit shock waves to exit acoustic-delay chamber 58 via outlet 20. In some embodiments, an acoustic coupling gel (not shown) may be disposed between member 70 and tissue 74 to lubricate and provide additional acoustic transmission into tissue 74.

In the embodiment shown, probe 38 includes an acoustic mirror 78 that comprises a material (e.g., glass) and is configured to reflect a majority of sound waves and/or shock waves that are incident on the acoustic mirror. As shown, acoustic mirror 78 can be angled to reflect sound waves and/or shock waves (e.g., that originate at spark head 22) toward outlet 20 (via acoustic-delay chamber) in a defocused manner. In the embodiment shown, housing 14 can comprise a translucent or transparent window 82 that is configured to permit a user to view (through window 82, chamber 18, chamber 58, and member 70) a region of a patient (e.g., tissue 74) comprising target cells (e.g., during application of shock waves or prior to application of shock waves to position outlet 20 at the target tissue). In the embodiment shown, window 82 comprises an acoustically reflective material (e.g., glass) that is configured to reflect a majority of sound waves and/or shock waves that are incident on the window. For example, window 82 can comprise clear glass of sufficient thickness and strength to withstand the high-energy acoustic pulses produced at spark head 22 (e.g., tempered plate glass having a thickness of about 2 mm and an optical transmission efficiency of greater than 50%).

In FIG. 3, a human eye 86 indicates a user viewing the target tissue through window 82, but it should be understood that target tissue may be "viewed" through window 82 via a camera (e.g., a digital still and/or video camera). By direct or indirect observation, acoustic energy can be positioned, applied, and repositioned according to target tissues, such as a region of cellulite, and by indications of acoustic energy, such as a change in the color of the tissue.

Figure 4:
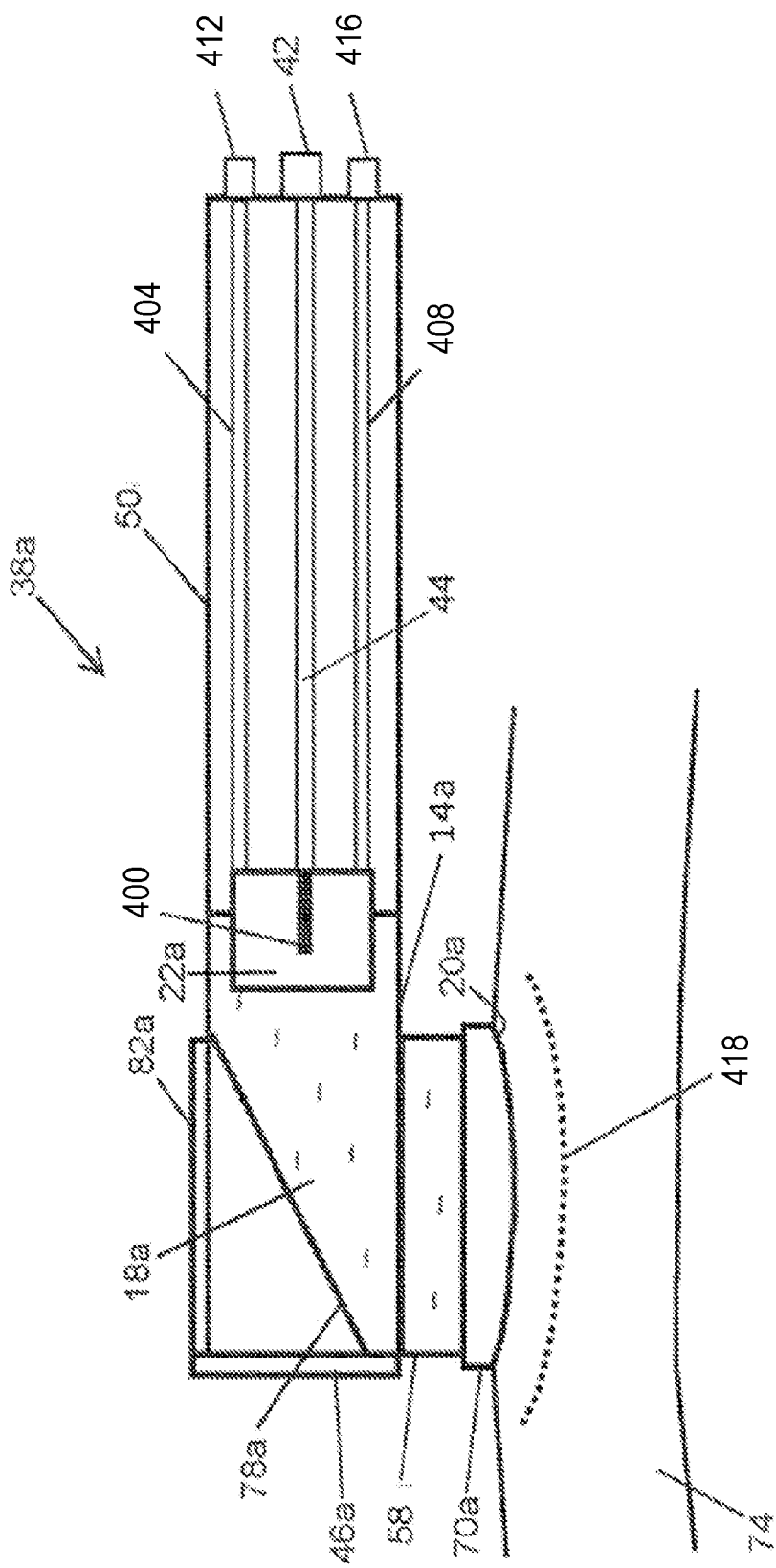
FIG. 4 depicts a cross-sectional side view of a handheld probe for some embodiments of the present EH shock wave generating acoustic subcision devices.

FIG. 4 depicts a cross-sectional side view of a second embodiment 38a of the present handheld probes or handpiece for use with some embodiments of the present EH shock wave generating systems and apparatuses. Housing 14a is substantially similar in some respects to housing 14 of FIG. 3, for example housing 14a houses or encloses some components of probe 38a. Probe 38a is substantially similar in some respects to probe 38, and the differences are therefore primarily described here. For example, probe 38a is also configured such that the plurality of electrodes of spark head 22a are not visible to a user viewing a region (e.g., of target tissue) through window 82a and outlet 20a. However, rather than including an optical shield, probe 38a is configured such that spark head 22a (and the electrodes of the spark head) are offset from an optical path extending through window 82a and outlet 20a. In this embodiment, acoustic mirror 78a is positioned between spark head 22a and outlet 20a, as shown, to define a boundary of chamber 18a and to direct acoustic waves and/or shock waves from spark head 22a to outlet 20a. In the embodiment shown, window 82a can comprise a polymer or other acoustically permeable or transmissive material because acoustic mirror 78a is disposed between window 82a and chamber 18a and sound waves and/or shock waves are not directly incident on window 82a (i.e., because the sound waves and/or shock waves are primarily reflected by acoustic mirror 78a).

In the embodiment shown in FIG. 4, spark head 22a includes a plurality of electrodes 400 that define a plurality of spark gaps. The use of multiple spark gaps can be advantageous because it can double the number of pulses that can be delivered in a given period of time. For example, after a pulse vaporizes an amount of liquid in a spark gap the vapor must either return to its liquid state or must be displaced by a different portion of the liquid that is still in a liquid state. In addition to the time required for the spark gap to be re-filled with water before a subsequent pulse can vaporize additional liquid, sparks also heat the electrodes. As such, for a given spark rate, increasing the number of spark gaps reduces the rate at which each spark gap must be fired and thereby extends the life of the electrodes. Thus, ten spark gaps potentially increases the possible pulse rate and/or electrode life by a factor of ten.

As noted above, high pulse rates can generate large amounts of heat that may increase fatigue on the electrodes and/or increase the time necessary for vapor to return to the liquid state after it is vaporized. In some embodiments, this heat can be managed by circulating liquid around the spark head. For example, in the embodiment of FIG. 4, probe 38a includes conduits 404 and 408 extending from chamber 18a to respective connectors 412 and 416, as shown. In this embodiment, connectors 412 and 416 can be coupled to a pump to circulate liquid through chamber 18a (e.g., and through a heat exchanger). For example, in some embodiments, pulse-generation system 26 (FIG. 3) can comprise a pump and a heat exchanger in series and configured to be coupled to connectors 412 and 416 via conduits or the like. In some embodiments, a filter can be included in probe 38a, in a spark generation system (e.g., 26), and/or between the probe and the spark generation system to filter liquid that is circulated through the chamber.

As illustrated in FIG. 4, application of each shock wave to a target tissue includes a wave front 418 propagating from outlet 20a and traveling outward through tissue 74. As shown, wave front 418 is curved according to its expansion as it moves outwardly and partially according to the shape of the outer surface of outlet member 70a that contacts tissue 74. In other embodiments, such as that of FIG. 3, the outer shape of the contact member can be planar.

In the present embodiments, a pulse rate of a few Hz to many KHz (e.g., up to 5 MHz) may be employed. Because the fatiguing event produced by a plurality of pulses, or shock waves, is generally cumulative at higher pulse rates, treatment time may be significantly reduced by using many moderately-powered shock waves in rapid succession rather than a few higher powered shock waves spaced by long durations of rest. As noted above, at least some of the present embodiments (e.g., those with multiple spark gaps) enable electro-hydraulic generation of shock waves at higher rates. For example, FIG. 5A depicts a timing diagram 500 enlarged to show two sequences of voltage pulses 504, 508 applied to the electrodes of the present embodiments with a delay period 512 in between, and FIG. 5B depicts a timing diagram 516 showing a greater number of voltage pulses applied to the electrodes of the present embodiments.

In additional embodiments that are similar to any of spark head 22a, 22b, 22c, a portion of the respective sidewall (120, 120a, 120b) may be omitted such that the respective spark chamber (124, 124a, 124b) is also omitted or left open such that liquid in a larger chamber (e.g., 18 or 18a) of a corresponding handpiece can freely circulate between the electrodes. In such embodiments, the spark chamber (e.g., sidewall 120, 120a, 120b can include liquid connectors or liquid may circulate through liquid ports that are independent of spark chamber (e.g., as depicted in FIG. 4).

A series of events (sparks) initiated by a plurality of bursts or groups 504 and 508 delivered with the present systems and apparatuses can comprise a higher pulse rate (PR) that can reduce treatment time relative to lower PRs which may need to be applied over many minutes. The embodiments can be used to deliver shock waves at the desired pulse rate.

Figure 6:
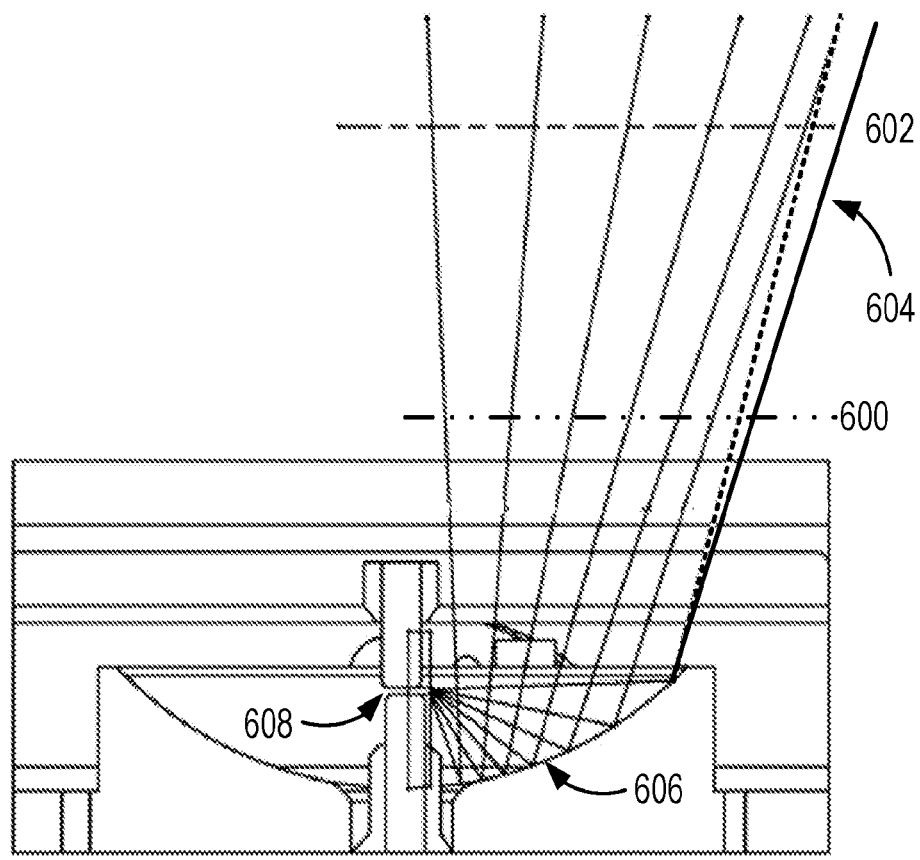
FIG. 6 depicts a free-form reflector and a graphical illustration of acoustic waves.

FIG. 6 depicts a free-form reflector. The free-form reflector may be designed using a process of spline interpolation. In the embodiment shown, the resulting reflector shape can be modeled, for example, using an acoustic finite element method (FEM) simulation. FEM refers to a numerical technique for finding approximate solutions to boundary value problems. If a FEM simulation determines the free-form acoustic reflector is viable, a physical prototype can then be made and, if desired, physically tested.

In the embodiment shown, after the reflector shape is defined, ray tracing is used to approximate energy density that will be reflected by the reflector. Traditionally, ray tracing refers to a technique for generating an image by tracing paths of light and simulating the effects of its encounters with virtual object. Here, and as depicted in FIG. 6, ray tracing can be performed to approximate the energy density from the reflector shape defined by spline interpolation. In FIG. 6, acoustic waves 604 (depicted as vectors) are generated at an electrode gap 608 and reflected off of the free-form reflector 606. These acoustic waves ideally have a uniform pressure density once they reach a target tissue depth 600 and have been dissipated by at least a factor of two by the time they reach a diffusion depth 602 (e.g., a treatment cessation depth or an intended treatment cessation depth). In FIG. 6, acoustic waves 604 are approximately evenly spaced at the target tissue depth 600 indicating an approximately uniform energy distribution across the profile of the reflector. However, at the diffusion depth 602, the rays are farther apart indicating a lower energy density. While a uniform pressure density at the target tissue depth is ideal, peak pressure variations of 10, 20, or 30 percent over/under other peak pressure readings from the free-form reflector may also perform the desired therapeutic function with no undesired results.

FIG. 6 also includes a dashed line depicting a crossing or overlapping ray. Overlapping rays (or intersecting rays) are common in parabolic reflector designs. Such rays are indicative of increases in peak pressure as waves may combine and exhibit constructive interference, i.e., increase in magnitude. However, in free-form, i.e., not or non-parabolic or parabaloid, acoustic reflector designs, the rays do not intersect. That is the rays do not intersect before or after the diffusion depth 602. Accordingly, the free-form acoustic reflector does not cause increases in peak pressure at various positions past the diffusion 602.

Figure 7:
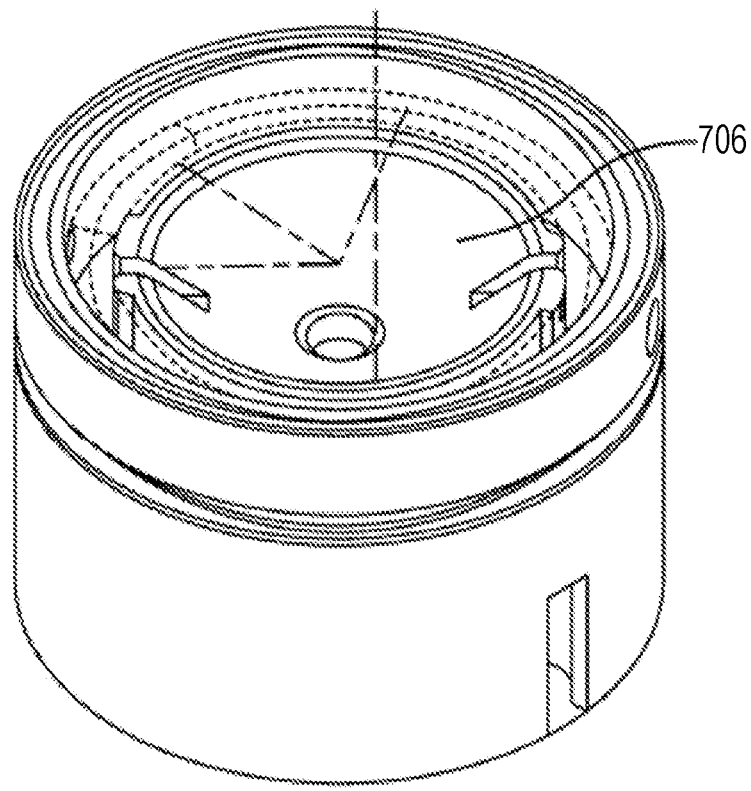
FIGS. 7 and 8 depict isometric and cross-sectional views of a sparkhead portion of an acoustic subcision device, respectively.
Figure 8:
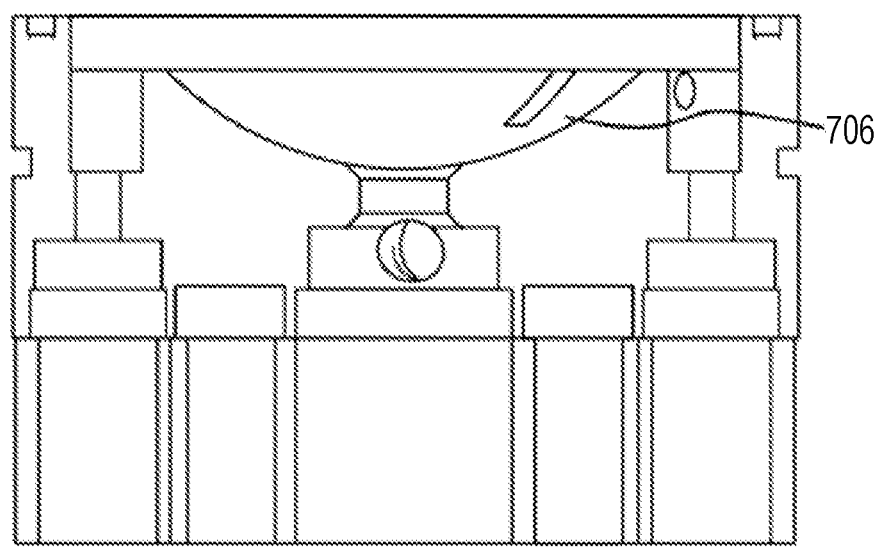

FIGS. 7 and 8 depict an embodiment of the therapeutic wave generator. FIG. 7 depicts an isometric view of a sparkhead portion of the disclosed therapeutic wave generator, comprising a free-form reflector 706. Additionally, FIG. 8 depicts a cross-section of a sparkhead portion of one embodiment of the therapeutic wave generator, comprising a free-form reflector 706.

Figure 9:
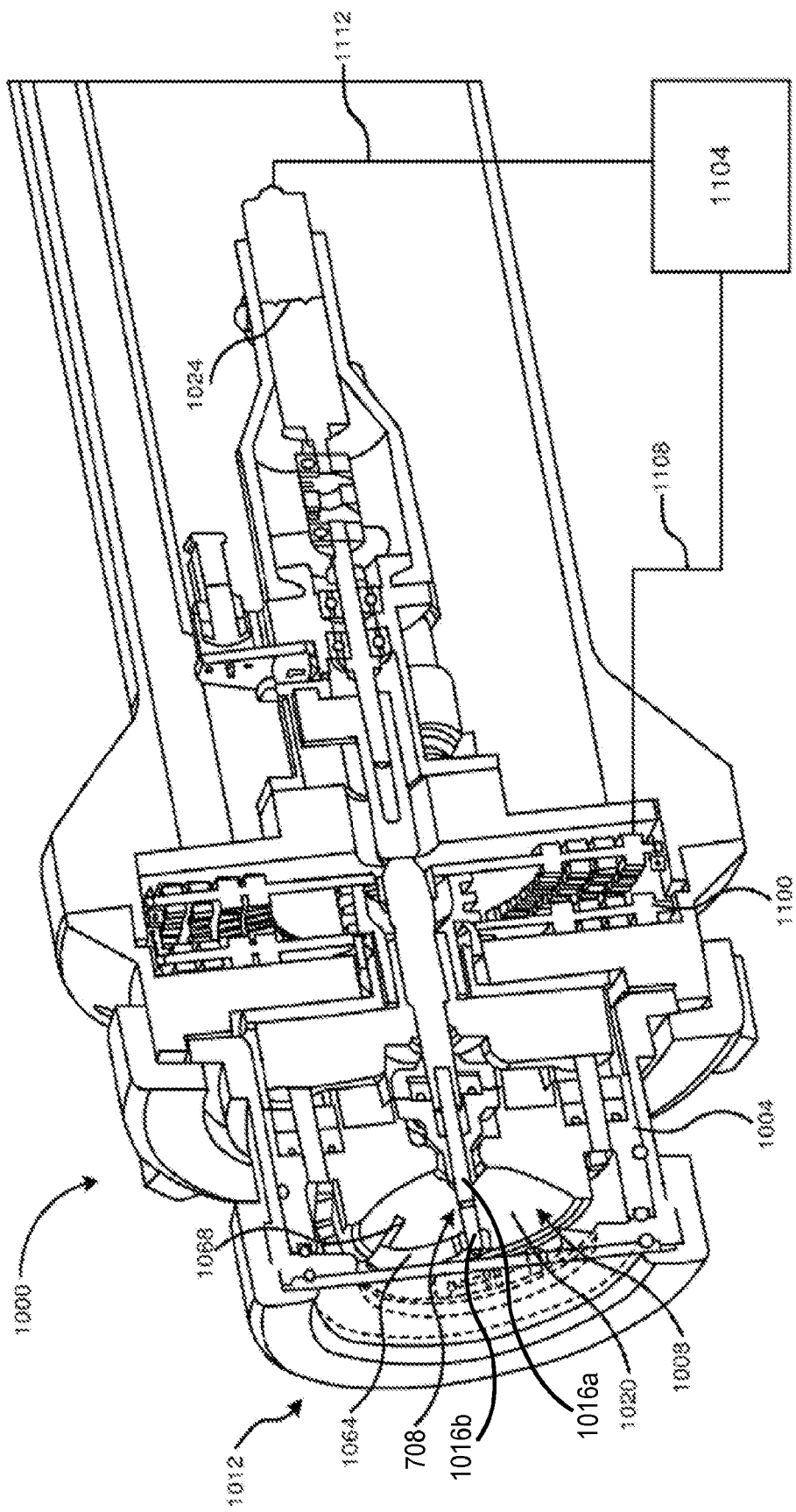
FIG. 9 depicts a cross-sectional view of one embodiment of an acoustic subcision device for electrohydraulic generation of acoustic waves that have improved acoustic wave fronts.

FIGS. 9, 10, and 11A-11C illustrate examples of an apparatus for electrohydraulic generation of acoustic wave. FIG. 9 depicts a cross-sectional drawing of one embodiment of an apparatus for electrohydraulic generation of acoustic waves that have improved acoustic wavefronts. As shown in FIG. 9, the apparatus 1000 for electrohydraulic generation of acoustic waves comprises: a housing 1004 defining a chamber 1008 and a shock wave outlet 1012; a liquid disposed in the chamber 1008; an acoustic reflector 1020 within the chamber 1008; a plurality of electrodes 1016a, 1016b (e.g., in the spark head or module) configured to be disposed in the chamber 1008 to define one or more spark gaps 708; and a pulse generation system configured to apply voltage pulses to the electrodes 1016a, 1016b at a rate of between 10 Hz and 5 MHz. In the embodiment shown, acoustic reflector 1020 is or comprises a free-form reflector, while in other embodiments, the acoustic reflector may be parabaloid.

In this embodiment, a stabilized acoustic wavefront is achieved using a free-form acoustic reflector that has the spark gap, formed from a plurality of electrodes, maintained at a constant focal location from the acoustic reflector.

Figure 10:
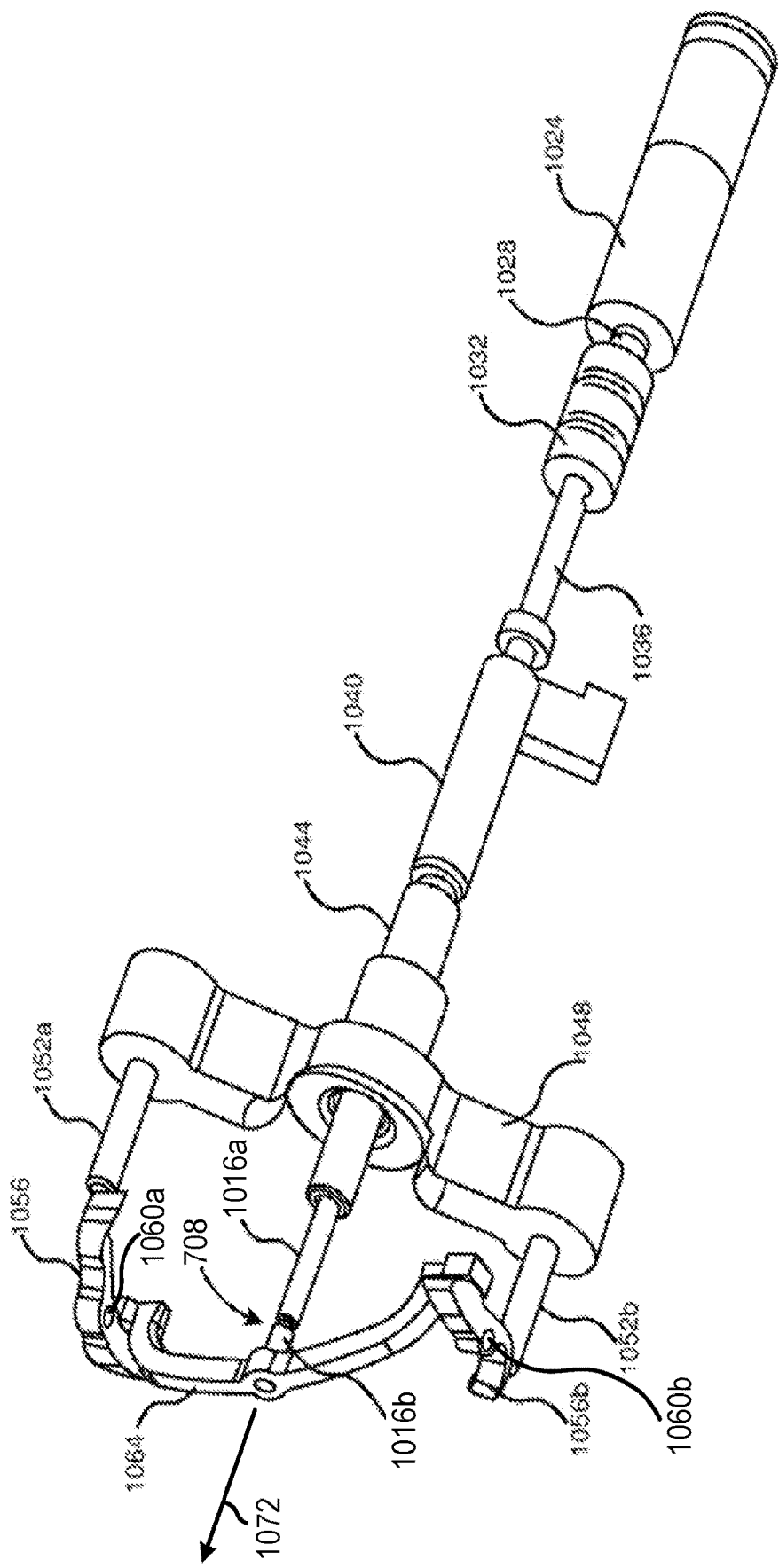
FIG. 10 depicts a perspective view of certain components the acoustic subcision device of FIG. 9.
Figures 11A, 11B, 11C:
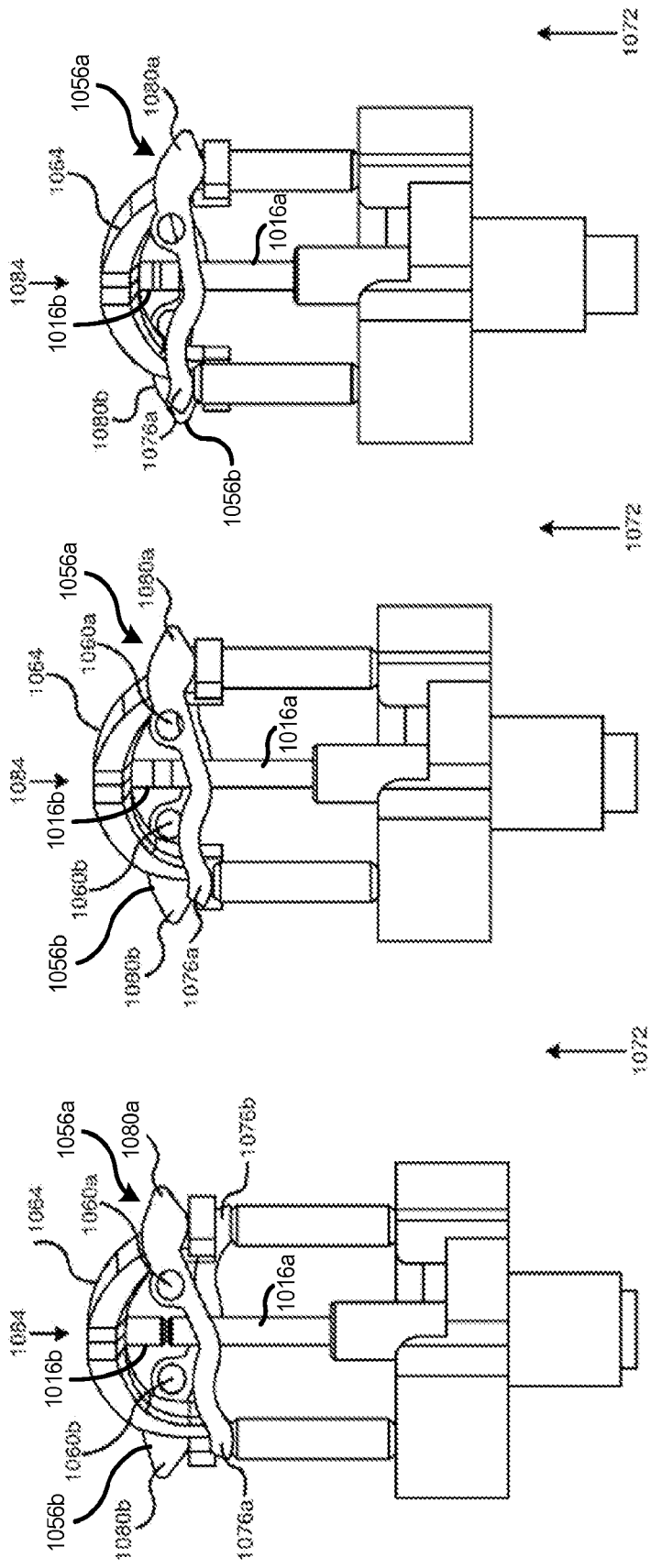
FIGS. 11A-11C depict three views illustrating the function of the components of FIG. 10.

In some of the present embodiments, a spark gap between a plurality of (e.g., two) electrodes is automatically adjusted using a single servomotor 1024 to maintain the spark gap at a substantially constant focal location from the reflector. For example, in the embodiment shown in FIGS. 9, 10, and 11A-11C, a single servomotor is used to move a pair of electrodes in such a way that the size and location of the electrode gap are maintained substantially constant. FIG. 9 depicts a perspective, cross-sectional view of a portion of an apparatus or probe 1000 that can be connected to a power source to electrohydraulically generate shock waves; FIG. 10 depicts a perspective view of the components of probe 1000 that permit adjustment of the electrodes to maintain the size and location of the spark gap; and FIGS. 11A-11C depict the components of FIG. 10 at three different positions illustrating the maintenance of the spark gap.

In the embodiment shown, apparatus 1000 includes a housing 1004 defining a chamber 1008 and a shock wave outlet 1012, and the chamber configured to receive (e.g., be filled with) a liquid such as water or saline. As shown, apparatus 1000 also comprises a plurality of electrodes 1016a, 1016b and an acoustic reflector 1020 disposed in (e.g., defining part of the boundary of) the chamber 1008. As shown, electrodes 1016 are configured to be disposed in chamber 1008 to define one or more spark gaps 708 having a size (i.e., distance between end surfaces of the electrodes 1016a and 1016b) and a location. In the embodiment shown, reflector 1020 is a free-form reflector.

In the embodiment shown, apparatus 1000 comprises a single servomotor 1024 mechanically coupled to the plurality of electrodes 1016a, 1016b, and is configured to adjust each of the electrodes, to maintain the size and location of spark gap 708 substantially constant. In this embodiment, servomotor 1024 has an output shaft 1028 with a chuck or coupler 1032 that couples shaft 1028 to a lead screw 1036 that is coupled via threads to a shuttle or pusher 1040 such that rotation of lead screw 1036 results in longitudinal movement of pusher 1040. A primary electrode 1016a is coupled to (e.g., configured to be pushed by) pusher 1040; for example, in the embodiment shown, a primary electrode carrier 1044 extends/carries primary electrode 1016a and extends to pusher 1040 as shown. In other embodiments, electrode carrier 1044 and primary electrode 1016a may be unitary (e.g., formed of a single piece of material). As shown, a spreader bar 1048 is coupled in fixed relation to primary electrode carrier 1044, and spreader bar 1048 carries two pusher rods 1052a, 1052b extending from spreader bar 1048 and configured to interact with two respective pivot arms 1056a, 1056b. As shown, pivot arms 1056a, 1056b are each pivotally coupled (e.g., via pins) to housing 1004 at respective pivot points 1060a, 1060b such that, as pusher rods 1052a, 1052b advance in direction 1064.

In this embodiment, secondary electrode 1016b is coupled to (and carried by) a secondary electrode carrier 1064. As shown, secondary electrode carrier 1064 has an inverted U-shape and is slidably coupled to housing 1004 (e.g., slidably disposed in a slot or track 1068). Additionally, a spring or other biasing member (not shown) biases secondary carrier 1064 and secondary electrode 1016b in a direction 1072 away from primary electrode 1016a.

In this configuration, and as shown in the progression in FIGS. 11A-11C, when motor 1024 is actuated, shaft 1028 rotates lead screw 1036 which, in turn, longitudinally advances shuttle 1040, primary electrode carrier 1044, primary electrode 1016a, spreader bar 1048, and pusher rods 1052a, 1052b in direction 1072. As these components advance, pusher rods 1052a, 1052b contact, and impart a force in direction 1072 on, respective first ends 1076a, 1076b of pivot arms 1056a, 1056b. The upward (in the orientation depicted in FIGS. 11A-11C) force on first ends 1076a, 1076b causes pivot arms 1056a, 1056b to pivot around their respective pivot points 1060a, 1060b, and moves the pivot arms' respective second ends 1080a, 1080b downward to impart a force in direction 1084 on secondary electrode carrier 1064 to move secondary electrode 1016b toward primary electrode 1016a. In this way, as the electrodes erode during use, a single servomotor can simultaneously move primary electrode 1016a upward and secondary electrode downward 1016b downward to maintain both the size and position of the electrode gap between the ends of the electrodes 1016a, 1016b.

Because the primary electrode 1060a is the anode, primary electrode 1060a may wear or degrade with each spark discharge at a rate faster than the secondary electrode 1060b that is the cathode, with a specific ratio. The length of first ends 1076a, 1076b of pivot arms 1056a, and 1056b from the pivot points 1060a, 1060b; and the length of the second ends 1076a, 1076b of pivot arms 1056a, and 1056b from the pivot points 1060a, 1060b; may be designed such that when motor 1024 moves one step to move primary electrode 1060a a fixed distance upward in the direction of 1072, the differential lengths of the pivot arms 1056a, 1056b from the pivot points 1060a, 1060b will cause the second ends 1076a, 1076b to push secondary electrode carrier 1064 to move secondary electrode 1016b downward in the direction of 1084 with the same ratio as the differential wear of the anode (electrode 1016a) and the cathode (electrode 1016b), thereby maintaining the gap 708 at the proper length while keeping the gap at the focal point of the reflector 1020.

In the embodiment shown, apparatus 1000 also houses a circuit board assembly 1100 which, as described in U.S. Provisional Patent Application No. 62/365,009 (incorporated above), is configured to receive voltage from an external pulse generation system (not shown) and deliver voltage pulses to and/or through primary electrode 1016a to generate sparks between the electrodes and thereby shock waves. In the embodiment shown, a controller 1104 is coupled in electrical communication with one or both of the electrodes (e.g., via circuit board assembly 1100 as shown or, in other embodiments, directly) via connection 1108, and with motor 1024 via connection 1112, such that the controller can control motor 1024 based on measurements of sparks between the electrodes. For example, to maintain a constant electrode gap size and location, a closed loop control is used to signal motor 1124 to feed the electrode forward and maintain spark gap 708 at the desired size. This closed loop control may be performed by measuring the pulse time of the electrical discharge at a particular charge voltage. The characteristics of the electrical discharge correlate very closely to the spark gap 708 (e.g., electrode gap) distance. By measuring these characteristics, closed loop control can be performed by signaling the motor 1024 to move and thereby maintain the gap between the electrodes and, in turn, maintain the desired electrical characteristics of the discharge.

In some embodiments, controller 1104 is a component of the spark-generation system (e.g., the functionality described for controller 1104 is incorporated into the instructions or code executed by the primary discharge controller of the spark-generation system). For example, motor 1024 can be driven directly from the main discharge controller of the spark-generation system by applying electrical pulses directly to the motor windings by means of extended leads. In other embodiments, controller 1104 is a second and/or independent controller with a separate adjustment function. For example, controller 1104 can be mounted in the housing and can receive analog or digital signals (e.g., electrical, optical, and/or the like) from a or the primary controller of the spark-generation system.

The electrohydraulic shock wave generators disclosed herein produces acoustic wavefronts having an improved acoustic wavefront uniformity. According to one embodiment, this improved acoustic wavefront uniformity is achieved through the use of an electrohydraulic generator using a free-form acoustic reflector and a single servomotor electrode adjustment system. As a result, the electrohydraulic apparatuses disclosed here provides more consistent, more comfortable, acoustic shock wave therapy when used to treat a patient.

Figure 12:
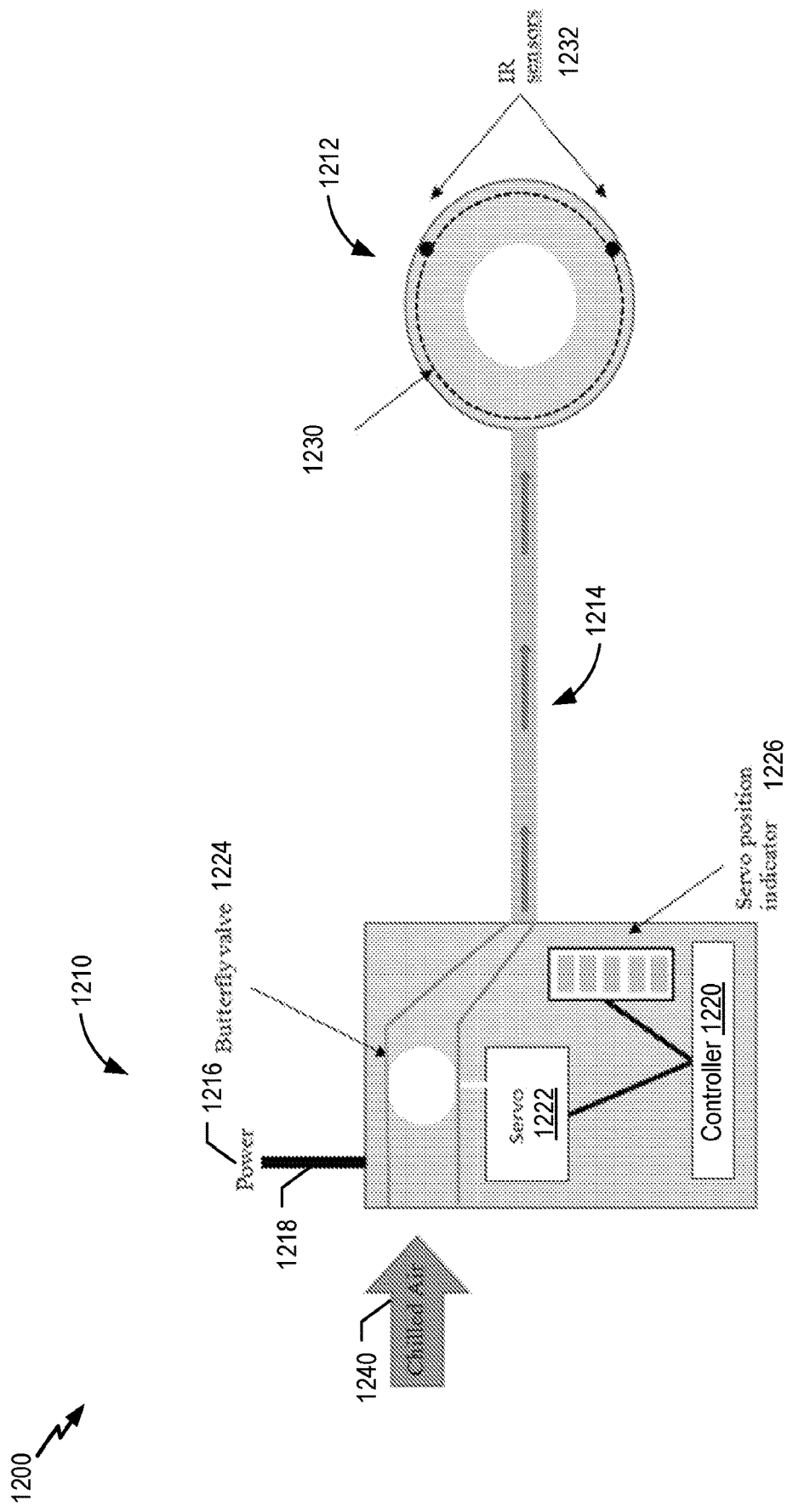
FIG. 12 depicts a schematic diagram of an example of a vacuum system.

FIG. 12 illustrates a schematic drawing of an example of a vacuum system, such as vacuum system 112 of FIG. 1. FIG. 12 depicts a distributed vacuum system 1200 including a controller 1210 (e.g., control unit) and a vacuum head 1212 (e.g., remote head) capable of being used for assisting in application of one or more types of therapies. In FIG. 12, the vacuum head 1212 is separate from the controller 1210 and is coupled to the controller via a flexible tube or conduit, referred to as an umbilical 1214.

The controller 1210 (e.g., control unit) includes a controller 1220 (e.g., control logic, circuit board, processor and memory, field programmable gate array, etc.), a motor 1222 (e.g., a servo or servo motor), a valve 1224 (e.g., a butterfly valve), and an indicator 1226. As illustrated in FIG. 12, controller 1210 is coupled to a power source 1218 (e.g., via a power cable 1216). In other implementations, controller 1220 is battery powered and includes a battery or other power source. The controller 1220 is configured to control motor 1222 to operate valve 1224, such as control or adjust a position of the valve 1224. Additionally, controller 1220 is configured to control indicator 1226 to indicate a position of the valve 1224. Accordingly, controller 1220 is configured to control delivery of negative pressure and/or chilled air 1240 to vacuum head 1212.

Chilled air 1240 may be used for only some procedures. For example, chilled air may be suitable for laser induced optical breakdown (LIOB) therapies when laser or electromagnetic waves/radiation are emitted to a treatment area. The chilled air 1240 may not be used with, such as may provide little to no benefit for, acoustic subcision therapies or treatments. However, inclusion of chilled air components and functionality into vacuum system 1200 may enable a single vacuum system (e.g., 1200, such as 1210 and/or 1212 thereof) to be used in acoustic subcision treatments and other treatments (e.g., LIOB treatments, such as tattoo removal).

The vacuum head 1212 includes one or more lights 1230 and one or more sensors 1232. As illustrated in FIG. 12, vacuum head 1212 includes one or more LEDs and one or more infrared sensors. In some implementations, the one or more LEDs are configured to provide light to a base and/or window of the vacuum head to light up a treatment location. Additionally, or alternatively, the vacuum head 1212 is configured to provide an indication via the one or more LEDs. For example, the vacuum head 1212 may be configured to provide an indication of vacuum status. To illustrate, vacuum head 1212 may indicate operational status (e.g., negative pressure or vacuum achieved and/or maintained), vacuum release (e.g., loss of vacuum or negative pressure), or both via the one or more LEDs. The umbilical 1214 may include one or more lumens, such as one or more dedicated lumens for providing negative pressure, chilled air, return air, etc.

In other implementations, controller 1210 may include a power switch (e.g., 1302) configured to activate and/or apply negative pressure. For example, controller 1210 may not include one or more of the controller 1220, the motor 1222, the valve 1224, or the indicator 1226. To illustrate, the controller 1210 may include or correspond to a control system of a pump (e.g., control activation or on/off of the pump). Alternatively, controller 1210 includes one or more of the controller 1220, the motor 1222, the valve 1224, or the indicator 1226, but in such implementations, the one or more of the controller 1220, the motor 1222, the valve 1224, the indicator 1226, or a combination thereof, correspond to vacuum or negative pressure. To illustrate, the valve 1224 may be configured to control application of negative pressure responsive to the motor 1222 controlled by the controller 1220, and the indicator 1226 indicates vacuum pressure or valve 1224 position. In such implementations where chilled air components and/or functionality is omitted, vacuum head 1212 may include one port, such as a vacuum port and may not include a second or chilled air port. Additionally, or alternatively, umbilical 1214 may include a single lumen (e.g., negative pressure lumen).

Figure 13:
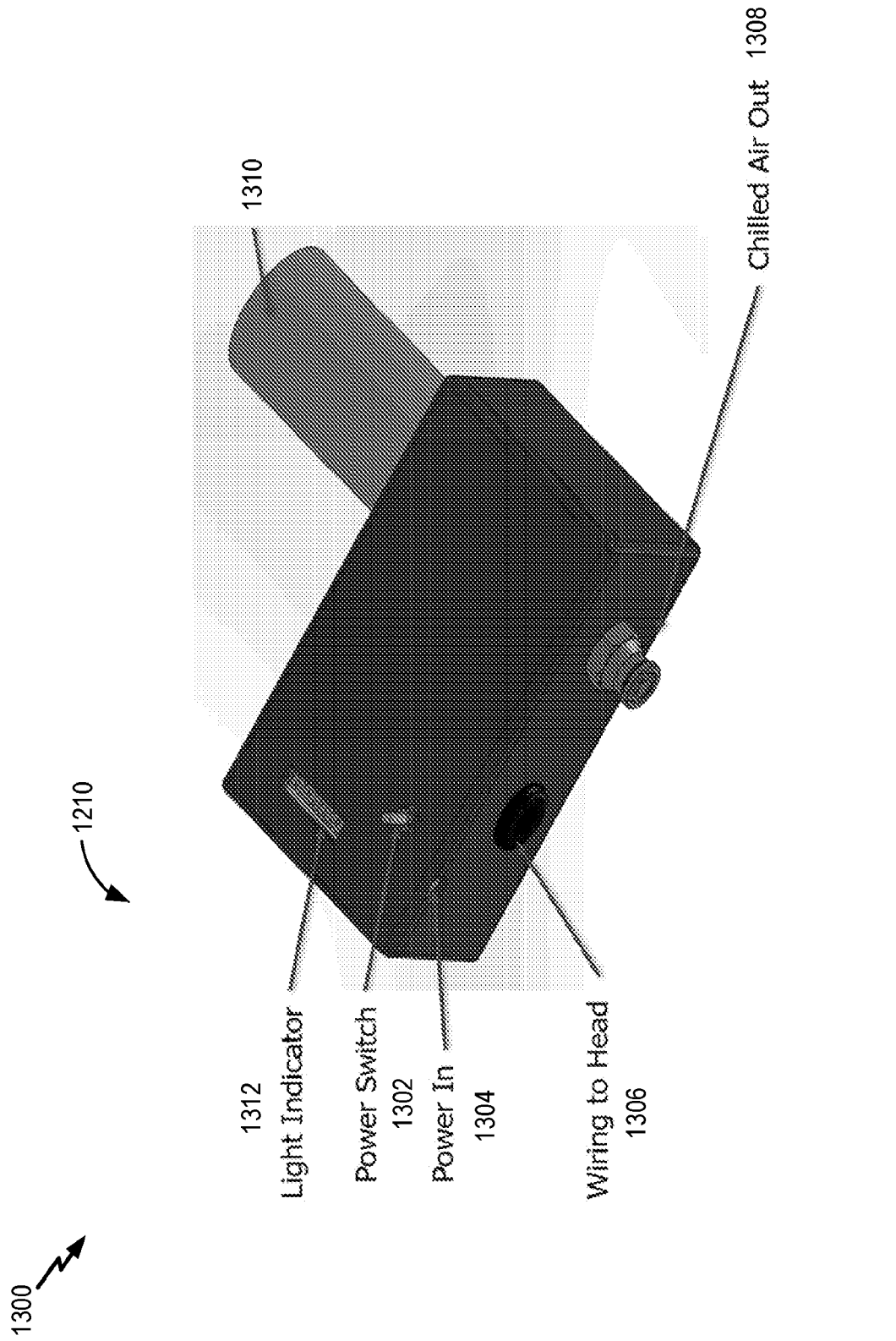
FIG. 13 depicts a perspective view of an example of a controller of a vacuum system.

FIG. 13 illustrates a perspective view 1300 of an example of the controller 1210 (e.g., a control unit). As illustrated in FIG. 13, the controller 1210 includes a power switch 1302, a power in port or jack 1304 configured to receive a plug, a wiring port 1306, an air port (e.g., a chilled air out port, a vacuum port, or both) 1308, an output tube or conduit 1310, and an indicator light 1312.

Figure 14:
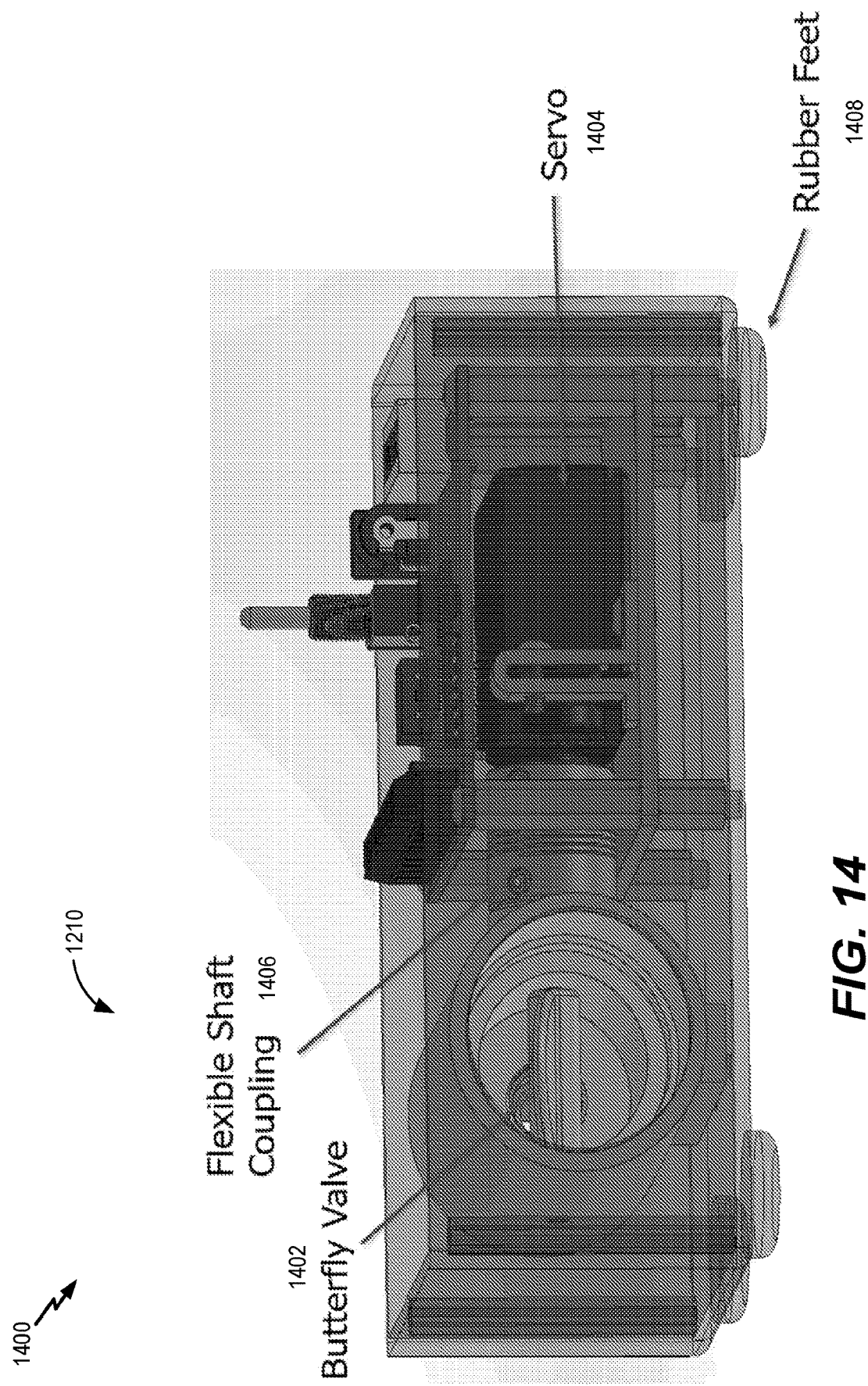
FIG. 14 depicts a perspective semi-transparent view of the example of the controller of FIG. 13.

FIG. 14 illustrates a perspective, semi-transparent view an example of the controller 1210 (e.g., a control unit) illustrating an example of placements of internal component of the controller 1210. As illustrated in FIG. 14, controller 1210 includes a butterfly valve 1402 coupled to a servo motor 1404 via a flexible shaft 1406. The controller 1210 further includes rubber feet 1408. An illustrative placement of other components of controller 1210 is also depicted in FIG. 14.

Figure 15:
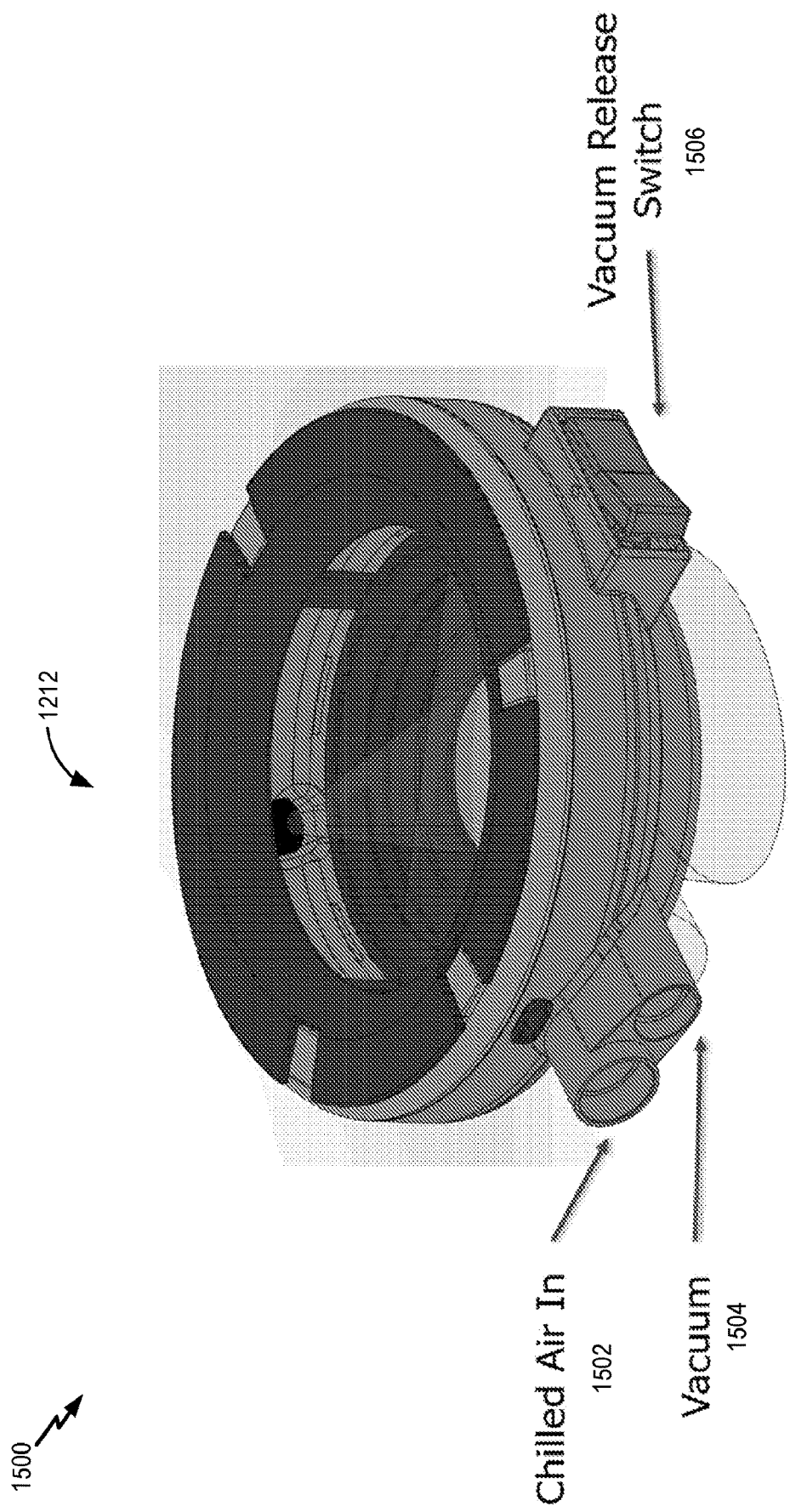
FIG. 15 depicts a perspective view of an example of a vacuum head of a vacuum system.

FIG. 15 illustrates a perspective view 1500 of an example of the vacuum head 1212 (e.g., a remote head). Vacuum head 1212 includes one or more ports. As illustrated in FIG. 15, the vacuum head 1212 includes a chilled air intake port 1502, a vacuum pressure intake port 1504, and a vacuum release switch 1506. In other implementations, vacuum head 1212 does not include the chilled air intake port 1502, such as when the vacuum head 1212 is not used to provide LIOB therapies. In some implementations, the vacuum head 1212 further includes one or more lights (e.g., 1232, such as LEDs).

The vacuum head 1212 is configured to assist in selectively providing acoustic subcision to a target area in a biological medium. As shown, vacuum head 1212 is configured to be used with an acoustic subcision device, such as acoustic subcision devices described herein, some of which may be positioned within the vacuum head. A distal (or lower in the orientation of FIG. 14) end of vacuum head 1212 is configured to be pressed against a biological medium (e.g., tissue 192 or skin). For example, a housing of vacuum head 1212 can comprise a polymer or other material. As shown, the housing of vacuum head 1212 defines one or more internal channels and one or more openings (e.g., an annular opening) through which vacuum is communicated (e.g., continuously or at multiple points around a perimeter of a treatment area) to apply suction to the skin or other biological medium. As used in this disclosure, the term "vacuum" refers to a pressure that is lower than ambient atmospheric pressure (e.g., negative pressure), rather than a complete absence of matter.

In some implementations, vacuum head 1212 includes a window (e.g., a transparent window) that allows transmission of shock waves through the vacuum head 1212, assists with cooling of the skin or other biological medium (e.g., by providing a heat sink that draws thermal energy from the skin or by providing chilled air), and/or assists with stabilization of the skin or other biological medium (e.g., by creating an enclosed space in which the vacuum or suction can be applied to the skin). In some embodiments, the window can comprise a sapphire material that may, for example, be cooled prior to being placed in contact with the biological medium (e.g., skin).

In some such implementations, the vacuum head 1212 assists in isolating a section of biological medium by pulling a portion of biological medium to come into contact with the window. This stabilizes the portion of biological medium for treatment. As shown in FIG. 15, in this embodiment, the housing of vacuum head 1212 includes external connections (e.g., ports 1502, 1504) through which a vacuum source can be connected to internal channels to be communicated to a treatment area.

In other embodiments, vacuum head 1212 also comprises a thermometer (e.g., an infrared or other non-contact thermometer) coupled to the housing and oriented to monitor the temperature of the skin or other biological medium. Other embodiments may omit the window in favor of an uncovered void or opening, omit a thermometer, and/or omit a light source (e.g., LED).

FIGS. 16A-16E illustrate additional views of examples of vacuum heads (e.g., remote heads) of a vacuum system, such as vacuum system 112 or 1200. FIG. 16A illustrates a perspective view of an example of a vacuum head 1612. FIG. 16B illustrates a side cross-section view of the vacuum head 1612 of FIG. 16A. Referring to FIG. 16A, an exemplary layout of lights 1632 and sensors 1634 are illustrated. In FIG. 16A, vacuum head include multiple indication lights 1632A (e.g., White LEDs), illumination lights 1632B (e.g., RGB LEDs), and sensors 1634 (e.g., underneath green circuit board), such as temperature sensors, pressure sensors, or both. FIG. 16 also illustrates the layout of lights 1632 and sensors 1634 and further illustrates a flange 1622 coupled to a bottom or base of body or housing of the vacuum head 1612. As illustrated in FIGS. 16A and 16B, flange 1622 (e.g., compliant member) is configured to form a seal with a treatment site to enable generation and maintenance of a vacuum or negative pressure by the vacuum head 1612.

FIGS. 16C and 16D illustrate additional views of the flange 1622 of the vacuum head 1612 of FIGS. 16A and 16B. Referring to FIG. 16C, a perspective view of the flange 1622 is illustrated. FIG. 16D illustrates a side cross-section view of the flange 1622 of FIG. 16C. In some implementations, flange 1622 is made of or includes a photopolymer.

FIG. 16E illustrates a side cross-section view of a vacuum head 1652.

Vacuum head 1652 includes an overmolded flange 1624 and a compact or low profile base (e.g., housing or body), relative to vacuum head 1612. Flange 1624 operates similar to flange 1622. The flanges 1622, 1624 illustrated in FIGS. 16A-16E may have a hardness of 30 Shore A to 50 Shore A in some implementations. The flanges 1622, 1624 may be configured to operate at pressure of about 5 in of mercury (in Hg), roughly 24 in HG under atmospheric pressure. Although no lights or sensors are illustrated in FIG. 16E, in other implementations, vacuum head 1652 includes lights (e.g., 1632A, 1632B, or both), sensors (e.g., 1634), or a combination thereof.

FIGS. 17A and 17B illustrate views of an example of integrated vacuum system. FIG. 17A illustrates a perspective view 1700 an example of the integrated vacuum system 1712 (e.g., integrated head). An integrated system refers to the controller or control unit (e.g., one or more components thereof) being included in a housing (also referred to as a vacuum head housing) that also includes or defines the vacuum head. The integrated vacuum system 1712 includes a housing or base defining one or more ports. Similar to the other vacuum systems, integrated vacuum system 1712 is also coupled to a power source, a chilled air source and/or a vacuum source. As illustrated in FIG. 17A, the integrated vacuum system 1712 includes LEDs and sensors. In other implementations, the integrated vacuum system 1712 may omit lights (e.g., LEDs), sensors, or both.

FIG. 17B illustrates a side view cut away 1750 of the example of the vacuum head 1212 (e.g., a remote head) illustrated in FIG. 17A. FIG. 17B illustrates through channels defined by the integrated vacuum system 1712 that correspond to the one or more ports illustrated in FIG. 17A. Additionally, the internal channels, annular ring, and window/opening referenced in FIG. 15 are illustrated in the vacuum head 1212 of the integrated vacuum system 1712 in FIG. 17B.

Figure 18:
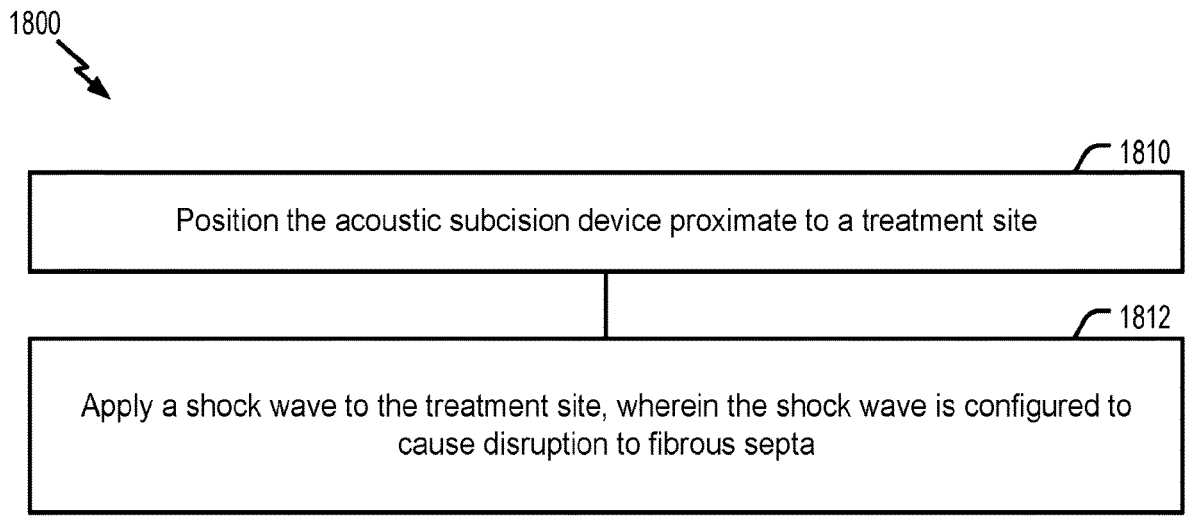
FIG. 18 depicts a flowchart illustrating an example of a method of treating a patient to improve the appearance of cellulite using an acoustic subcision device.

FIG. 18 illustrates a method 1800 of treating a patient to improve the appearance of cellulite using an acoustic subcision device. The method 1800 may be performed at or by system 100 (e.g., device 110 thereof), system 600, etc. Method 1800 includes positioning the acoustic subcision device proximate to a treatment site, at 1810. For example, the acoustic subcision device may include or correspond to acoustic subcision device 110, probe 38, probe 38a, system 600, the apparatus 1000, and the treatment site may include or correspond to a treatment area, tissue site 150, a treatment location within a treatment area, tissue 74, or tissue 192.

Method 1800 further includes applying a shock wave to the treatment site, wherein the shock wave, at 1812. For example, the shock wave may include or correspond to a shock wave pulse such as a rapid acoustic pulse (RAP). To illustrate, one of the acoustic subcision devices described above generates the shock wave pulse 132 of FIG. 1 or pulse 200 of FIG. 2A.

In some implementations, method 1800 further comprises applying a plurality of shock waves to the treatment site, wherein the plurality of shock waves are applied at a pulse repetition rate between 10 Hz and 200 Hz, 50 Hz and 100 Hz, 20 Hz and 500 Hz, or 10 Hz and 1000 Hz.

In some implementations, method 1800 further comprises applying the plurality of shock waves to the treatment site in discrete intervals, wherein the intervals have a duration of 1 to 3 minutes and correspond to a particular treatment location within the treatment site.

In some implementations, method 1800 further comprises positioning a vacuum head on the treatment site; applying the vacuum head to the treatment site; and generating a negative pressure. For example, the vacuum head may include or correspond to vacuum system 112, vacuum system 1202, vacuum head 1212, or integrated vacuum system 1612. To illustrate, a vacuum head 1212 is attached to tissue 192 of tissue site 150. In a particular implementation, method 1800 further comprises applying chilled air to the treatment site, as described with reference to FIG. 15.

Thus, method 1800 describes method of treating a patient to improve the appearance of cellulite using an acoustic subcision device. The acoustic subcision device enables therapeutic treatments and medical treatments to cause physical effects in tissue to cause disruption in fibrous septa in subcutaneous fat. As compared to current subcision devices and techniques, method 1800 is non-invasive, thereby increasing applicability and reducing complications and patient discomfort. Accordingly, the acoustic subcision devices and methods described herein may enable improved treatment of adipose tissue defects, thereby advancing patient comfort and confidence in the treatment.

Figure 19:
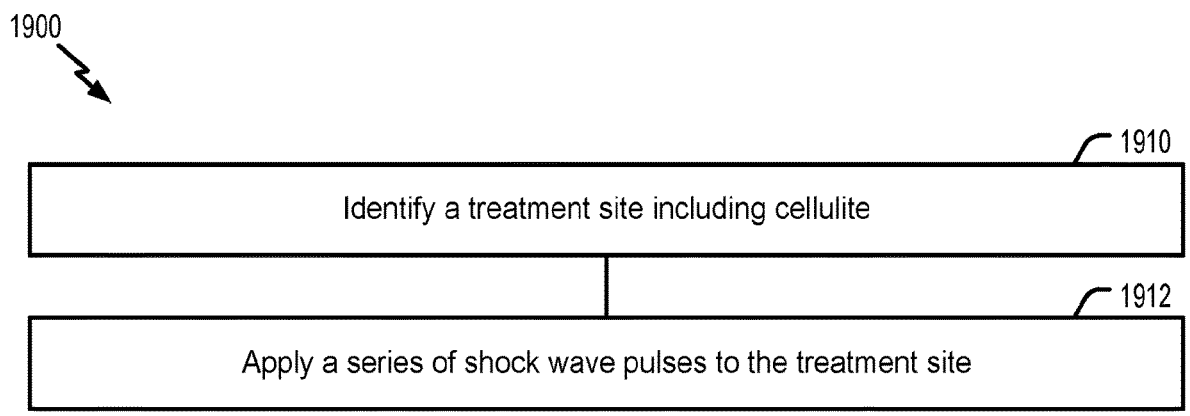
FIG. 19 depicts a flowchart illustrating an example of a method treating a patient to improve the appearance of cellulite by causing disruption to fibrous structures using rapid acoustic pulses.

FIG. 19 illustrates a method 1900 of treating a patient to improve the appearance of cellulite by causing disruption to fibrous structures (dermal and/or subdermal) using rapid acoustic pulses. The method 1900 may be performed by a patient or care provider using one or more components of system 100 or system 600. Method 1900 includes identifying a treatment site including cellulite, at 1910. For example, the treatment site may include or correspond to a treatment area, tissue site 150, a treatment location within a treatment area, tissue 74, or tissue 192. To illustrate, a patient or care provider (e.g., a technician, nurse, doctor, etc.) identifies a treatment site or area that includes cellulite or that corresponds to cellulite. In some implementations, method 1900 further includes identifying treatment locations within a treatment site or area.

Method 1900 also includes applying a series of shock wave pulses to the treatment site, wherein the shock wave pulses, at 1912. For example, the shock wave may include or correspond to a shock wave pulse such as a rapid acoustic pulse (RAP). To illustrate, an acoustic subcision device (e.g., acoustic subcision device 110, probe 38, probe 38a, system 600, the apparatus 1000) applies pulses 132 or pulses 200 as described herein, such as described with reference to FIGS. 5A and 5B.

In some implementations, method 1900 further comprises applying a plurality of shock waves to the treatment site, wherein the plurality of shock waves are applied at a pulse repetition rate between 10 Hz and 200 Hz, 50 Hz and 100 Hz, 20 Hz and 500 Hz, or 10 Hz and 1000 Hz.

In some implementations, method 1900 further comprises applying the plurality of shock waves to the treatment site in discrete intervals, wherein the intervals have a duration of 1 to 3 minutes and correspond to a particular treatment location within the treatment site.

In some implementations, method 1900 further comprises positioning a vacuum head on the treatment site; applying the vacuum head to the treatment site; and generating a negative pressure. For example, the vacuum head may include or correspond to vacuum system 112, vacuum system 1202, vacuum head 1212, or integrated vacuum system 1612. To illustrate, a vacuum head 1212 is attached to tissue 192 of tissue site 150. In a particular implementation, method 1900 further comprises applying chilled air to the treatment site, as described with reference to FIG. 15.

Thus, method 1900 treating a patient to improve the appearance of cellulite by causing disruption to dermal and/or subdermal fibrous structures using rapid acoustic pulses. The rapid acoustic pulses (e.g., a peak pressure, pressure rise and fall time, and repetition rate thereof) enable therapeutic treatments and medical treatments to cause physical effects in tissue to cause disruption in fibrous septa in subcutaneous fat. As compared to current subcision devices and techniques, method 1900 is non-invasive, thereby increasing applicability and reducing complications and patient discomfort. As compared to current pressure wave techniques or invasive techniques, method 1900 targets previously untreatable cellulite (e.g., advanced or Grade 2 and above cellulite) and other fibrotic conditions and utilizes targeted treatment sessions of increased peak pressure, pressure rise and fall time, and repetition rates to such targets to induce cumulative shock/stress that causes physical effects (e.g., disruption of sclerotic septa). Accordingly, the acoustic subcision devices and methods described herein may enable improved treatment of adipose tissue defects, thereby advancing patient comfort and confidence in the treatment.

Although method 1800 describes treating fibrous septa, other types of tissue may be treated, such as skin, adipose tissue, muscle tissue, organ tissue (e.g., reproductive organ tissue and/or corresponding skin tissue thereof), etc., in other implementations. Additionally, although method 1900 describes the treatment site as including cellulite, in other implementations the treatment site may include other things in addition to or in the alternative of cellulite, such as a keloid, a hypertrophic scar, or an implant capsular contraction. In some such implementations, compressed, non-cavitating RAPs (e.g., 200, 280, 295) may be used, such as unfocused or planar shock waves with a negative pulse component duration of less than 2 microseconds.

Figure 21B:
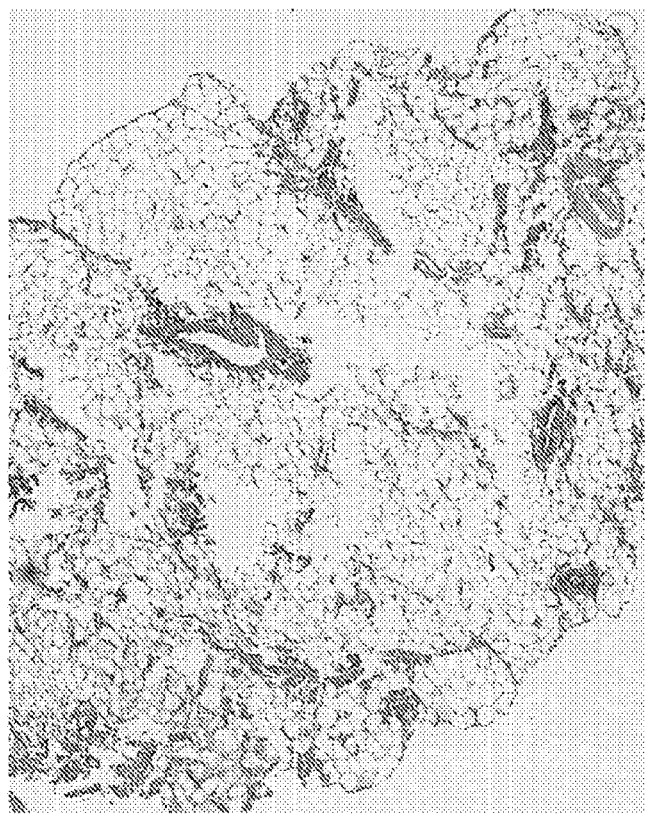
FIGS. 21A and 21B depict two photographs of slides illustrating comparisons of fibrous septa.
Figure 20A:
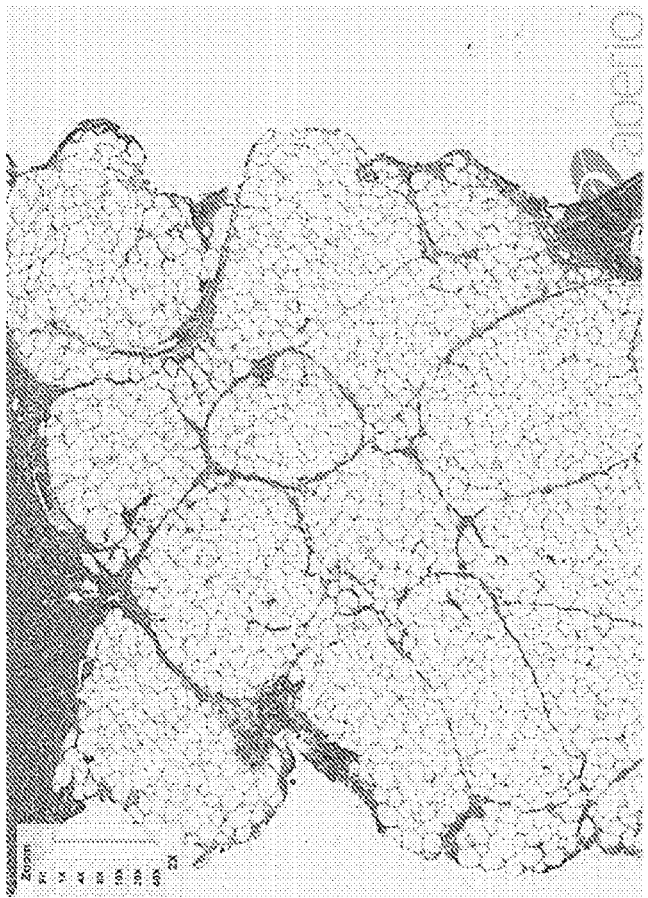
Figure 21B:
Figure 21A:
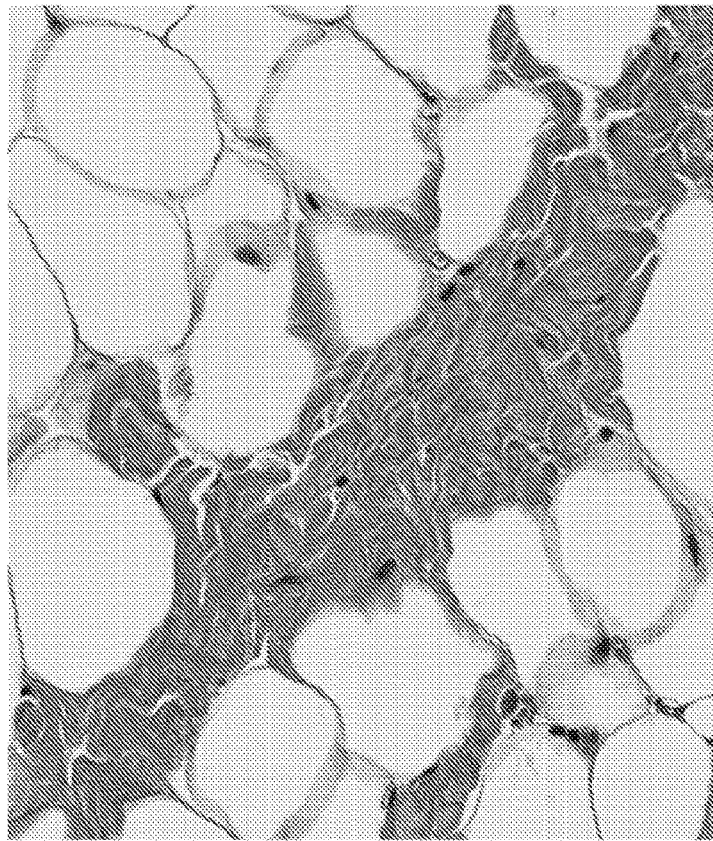
Figures 22A, 22B:
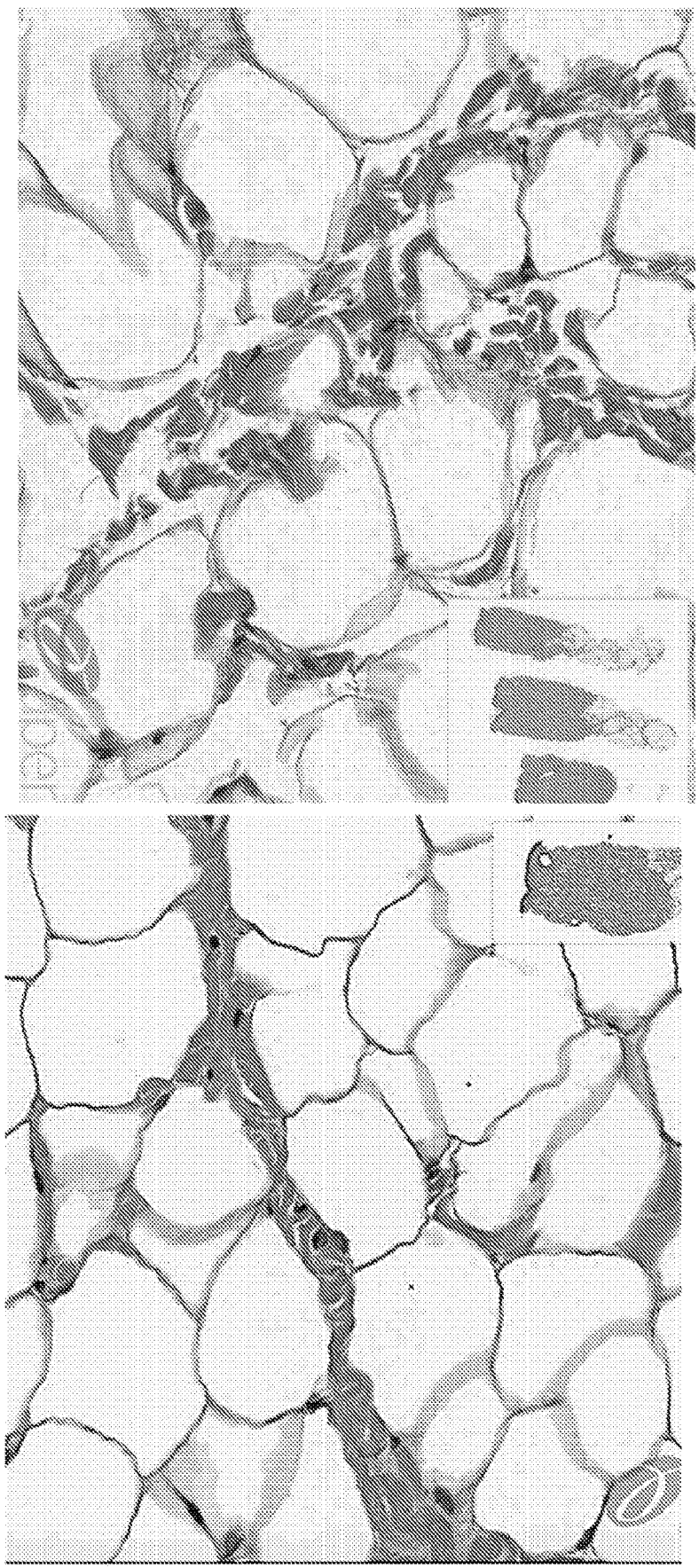
FIGS. 22A and 22B depict two photographs of slides illustrating comparisons of fibrous septa.

Referring to FIGS. 20A-22B, representative histologic slides depicting fibrous septa in subcutaneous fat and treated fibrous septa post therapy which has been disrupted are illustrated. FIGS. 20A, 21A, and 22A illustrate representative histologic slides illustrating fibrous septa of Gottingen Minipigs, such fibrous septa are representative of human fibrous septa that corresponds to cellulite, scars, dermal ridges, etc. FIGS. 20B, 21B, and 22B illustrate representative histologic slides illustrating fibrous septa after treatment with acoustic subcision.

Figures 23A, 23B:
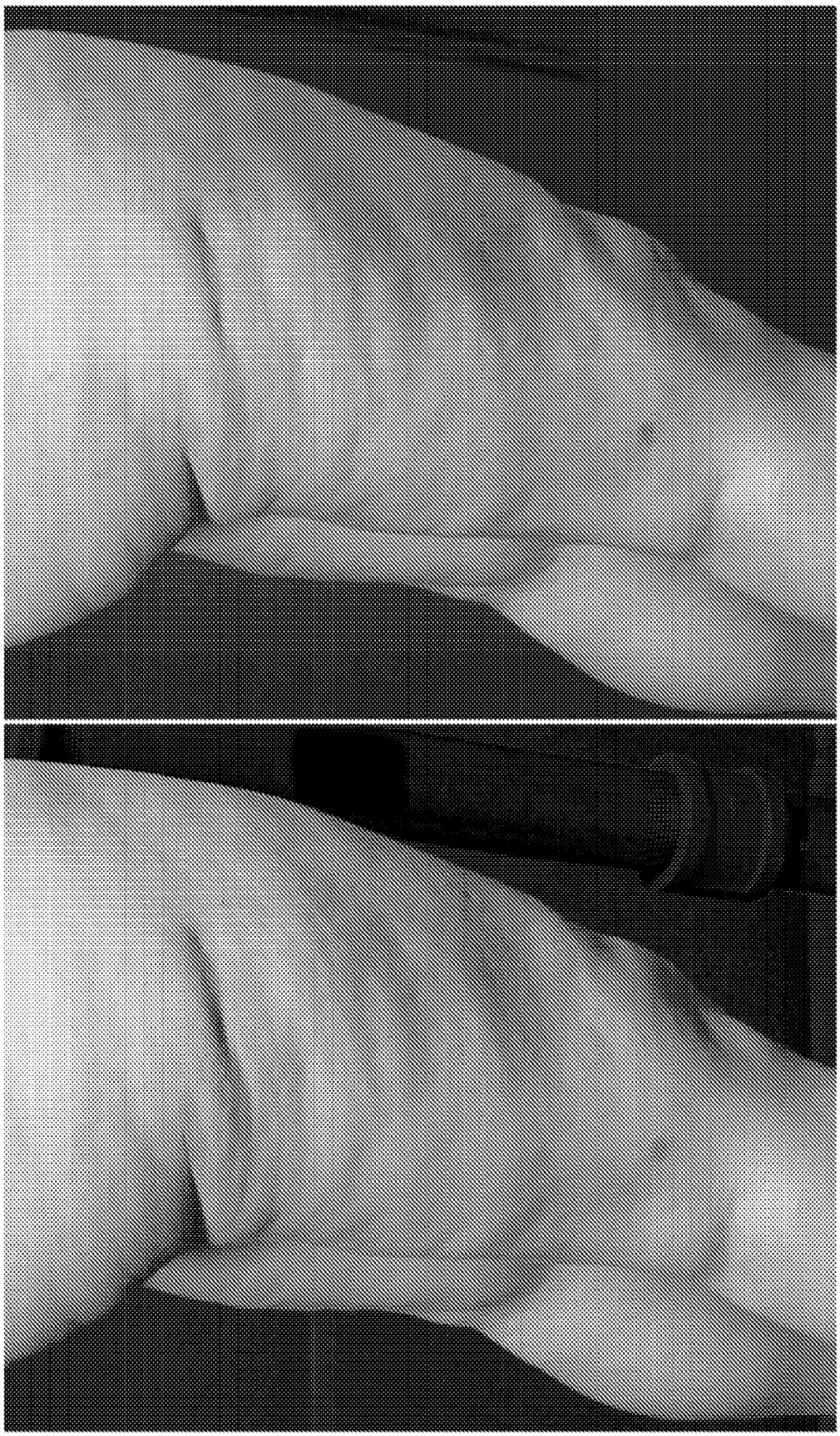
FIGS. 23A and 23B depict two photographs illustrating comparisons of cellulite before (FIG. 23A) and after (FIG. 23B) treatment with an Acoustic Subcision Device.

Referring to FIGS. 23A and 23B, before and after treatment photos are illustrated for a representative human patient. FIG. 23A is an image illustrating a cellulite dermal ridge on a thigh of a patient prior to treatment. FIG. 23B is an image illustrating the cellulite dermal ridge of FIG. 23A 12-weeks post treatment.

Referring to FIGS. 24A-30B, representative slides depicting treated fibrous septa post therapy, which has been disrupted, and tissue reactions, such as vascularization and collagenesis are illustrated. FIGS. 20A-30B are described further with reference to the Experimental Results section.

Experimental Results

Experiments were conducted to demonstrate the acoustic subcision device of this invention.

I. Example 1

Acoustic Subcision of Subcutaneous Fibrous Septa

A study was undertaken using Gottingen Minipigs, weighing about 30 kilograms, to evaluate the fibrous extracellular matrix disruption in subcutaneous fat using an acoustic subcision device that produced acoustic pulses having a high (relative to a second study described below in Example 2 and about 10 MPa) mean peak output pressure (i.e., average of the peak output pressures of each pulse). The acoustic subcision device produced unfocused, non-cavitating, rapid acoustic pulses (RAPs). Such unfocused, non-cavitating, rapid acoustic pulses (RAPs) may include or correspond to pulses 200, 280, 295.

The general procedure was to anesthetize the animals and prepare the mid-ventral sites by removing skin hair using hair clippers and then a razor. An acoustic subcision device was then used to provide high-frequency shock waves at the treatment site with each shock wave having a peak output pressure of about 10 MPa at a pulse repetition rate of 50 Hz for two minutes.

Following the treatment with high frequency shock waves, a biopsy was taken at the treatment site using a 3 mm circular punch biopsy instrument. The treated tissue sample was placed in a buffered formalin solution. Tissue slides were then made from the treated tissue sample and stained with hematoxylin and eosin (H&E) stain for microscopic examination. Tissue slides made from an untreated tissue samples served as control samples.

FIGS. 20A and 20B provide histological images at a 2× magnification showing the fibrous septa in the subcutaneous tissue. FIG. 20A illustrates fibrous septa of the untreated site, and FIG. 20B illustrates fibrous septa of the treated site. As can be seen from the histology images of FIGS. 20A and 20B, in comparison to the fibrous septa of the untreated site in FIG. 20A, the fibrous septa of the treated site in FIG. 20B appears to have experienced major disruption. FIG. 20B also illustrates that there was no evidence of cavitation or thermal damage in the tissue from the treated site. Furthermore, blood vessels remained intact and undamaged without any evidence of gross hematoma FIGS. 21A and 21B provide histological images from different tissue samples at a 20× magnification of showing the fibrous septa in the subcutaneous tissue.

FIG. 21A illustrates fibrous septa of untreated site, and FIG. 21B illustrates fibrous septa of the treated site. Again, as can be seen from the histology images of FIGS. 20A and 20B, in comparison to the fibrous septa of the untreated site in FIG. 21A, the fibrous septa of the treated site in FIG. 21B appears to have major disruption. FIG. 21B also illustrates that there was no evidence of cavitation or thermal damage in the tissue from the treated site. The results of this study support the ability of rapid acoustic pulses of this invention to cause acoustic subcision of subcutaneous fibrous septa.

II. Example 2

Acoustic Subcision of Subcutaneous Fibrous Septa

Another study was undertaken using Gottingen Minipigs to evaluate the fibrous septa disruption in subcutaneous fat using the acoustic subcision device that produced acoustic pulses having a medium (about 6 MPa) mean peak output pressure. The same general procedure as outlined in Example 1 was followed. However, the acoustic subcision device was then used to provide high-frequency shock waves at the treatment site with each shock wave having a mean peak output pressure of about 6 MPa at a pulse repetition rate of 100 Hz for three minutes.

FIGS. 22A and 22B provide histological images at a 20× magnification showing the fibrous septa in the subcutaneous tissue. FIG. 22 A illustrates fibrous septa of the untreated site, and FIG. 22B illustrates fibrous septa of a treated site. As can be seen from the histology images of FIGS. 22A and 22B, in comparison to the fibrous extracellular matrix of the untreated site of FIG. 22A, the fibrous extracellular matrix of the treated site in FIG. 22B appears to have major disruption. FIG. 22B also illustrates that there was no evidence of cavitation or thermal damage in the tissue from the treated site. The results of this study further support the ability of rapid acoustic pulse technology to cause acoustic subcision of subcutaneous fibrous structures. The results of this study also support the ability of acoustic subcision by RAP to safely cause disruption in tissue structures Experiments were conducted on humans to observe effects of acoustic subcision by shock waves on cellulite, such as fibrous subdermal septa, including sclerotic septa, in subcutaneous fat corresponding thereto.

III. Example 3

Pilot Study

An Institutional Review Board (IRB) approved human clinical trial was undertaken to test the effectiveness of the acoustic subcision device of this invention to improve the appearance of cellulite dimples or ridges caused from sclerotic fibrous septa. The goals of the pilot study were to verify that application of the non-invasive Acoustic Subcision Device (ASD) is well tolerated by patients, and that its application results in an improvement in the appearance of cellulite as measured by a reduction in the mean Simplified Cellulite Severity Score (CSS).

Women with Grade II cellulite and a BMI of less than 30 were eligible for enrollment. An area of about 25 cm×25 cm on an upper thigh of one randomly selected leg of each participant was treated in a single session with 20, one-minute applications of the ASD at 20 treatment sites within the area for a total of 20 minutes of treatment per patient in a single visit. Each of the 20 treatment sites received a one-minute application. Each high-frequency shock wave application had a mean peak output pressure of about 6 MPa at a pulse repetition rate of 50 Hz. Histologic evidence from animal studies has shown that these rapid acoustic pulses disrupt the collagen fibers throughout the adipose septa, effectively resulting in disruption and possibly subcision of the septa. Standardized photographs were taken before, and 12 weeks after treatment. These pre/post photograph pairs were assessed by three blinded reviewers who were asked to identify which photograph was taken post-treatment, and to provide 0 to 5-point CSS scores for both photographs. Adverse events and pain on a 0 to 10-point scale were recorded after treatment with 0 indicating no pain and 10 indicating worst possible pain.

Five women ages 30 to 54 were enrolled in the study. Only mild folliculitis that resolved within hours was noted at the treatment sites, with no erythema, edema, or contusions reported. Pain was rated at a level of "0" (no pain) on the 0-10 point scale at 97% of the treatment sites. The highest score was a 4 at one treatment site by one participant when the ASD was applied directly over the greater trochanter of the femur, which was resolved by repositioning the ASD lateral to the trochanter. Blinded assessment by the three reviewers showed an average reduction in CSS from 4.27 to 3.03 ($p<0.001$), and 100% correct identification of the post-treatment photograph from the pre/post treatment pair.

Results of this Pilot Study indicated that a single treatment session with the non-invasive, nearly painless Acoustic Subcision Device results in a significant improvement in the appearance of cellulite with no down time for the patient.

IV. Example 4

Treatment of Cellulite—Case Report

This case report was taken from the study described in Example 3 above.

One particular patient in this study had severe cellulite that was marked by a deep dermal-ridge. This type of deep dermal ridge would normally be treated using a surgical procedure, such as incisional subcision (i.e., where a special hypodermic needle is inserted through punctures in the skin to cut septa in subcutaneous fat). In this study, the particular patient's cellulite, including the deep dermal ridge, was treated per the protocol outlined above. FIGS. 23A and 23B illustrate photographs from immediately before the RAP treatment (FIG. 23A) and 12-weeks after the RAP treatment (FIG. 23B). As can be seen in FIGS. 23A and 23B, at the 12-week time point, the RAP treated deep dermal-ridge in the patient's thigh demonstrated obvious improvement. The patient's before and after cellulite photograph series was evaluated by three Independent Physician Review members and scored using Cellulite Severity Scale (Kaminer, et al., 2015). At 12-weeks, the patient cellulite, including the dermal ridge, demonstrated a significant 1.5-point reduction (4.83 before to 3.33 after). The single treatment with the acoustic subcision device using RAP treatment provided significant resolution of the cellulite ridge in this patient without any pain, bruising, swelling, or downtime.

The above specification and examples provide a description of the process and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present methods are not intended to be limited to the particular steps disclosed. Rather, they include all modifications and alternatives falling within the scope of the claims, and embodiments other than the one shown may include some or all of the features of the depicted embodiment. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

V. Example 5

Inducing a Tissue Reaction by RAPs

A study was undertaken using Gottingen Minipigs, weighing about 30 kilograms, to evaluate inducing a tissue reaction (e.g., vascularization) by physical disruption of tissue structures using (non-cavitating) compressed RAPs, such as 200, 280 and 295. The same general procedure as outlined in Example 1 was followed. However, the RAPs had a mean peak output pressure of 8-9 MPa at a rate of 50 Hz for two minutes. In addition, the RAPs had a negative pulse component duration of under 2 microseconds.

Figures 24A, 24B:
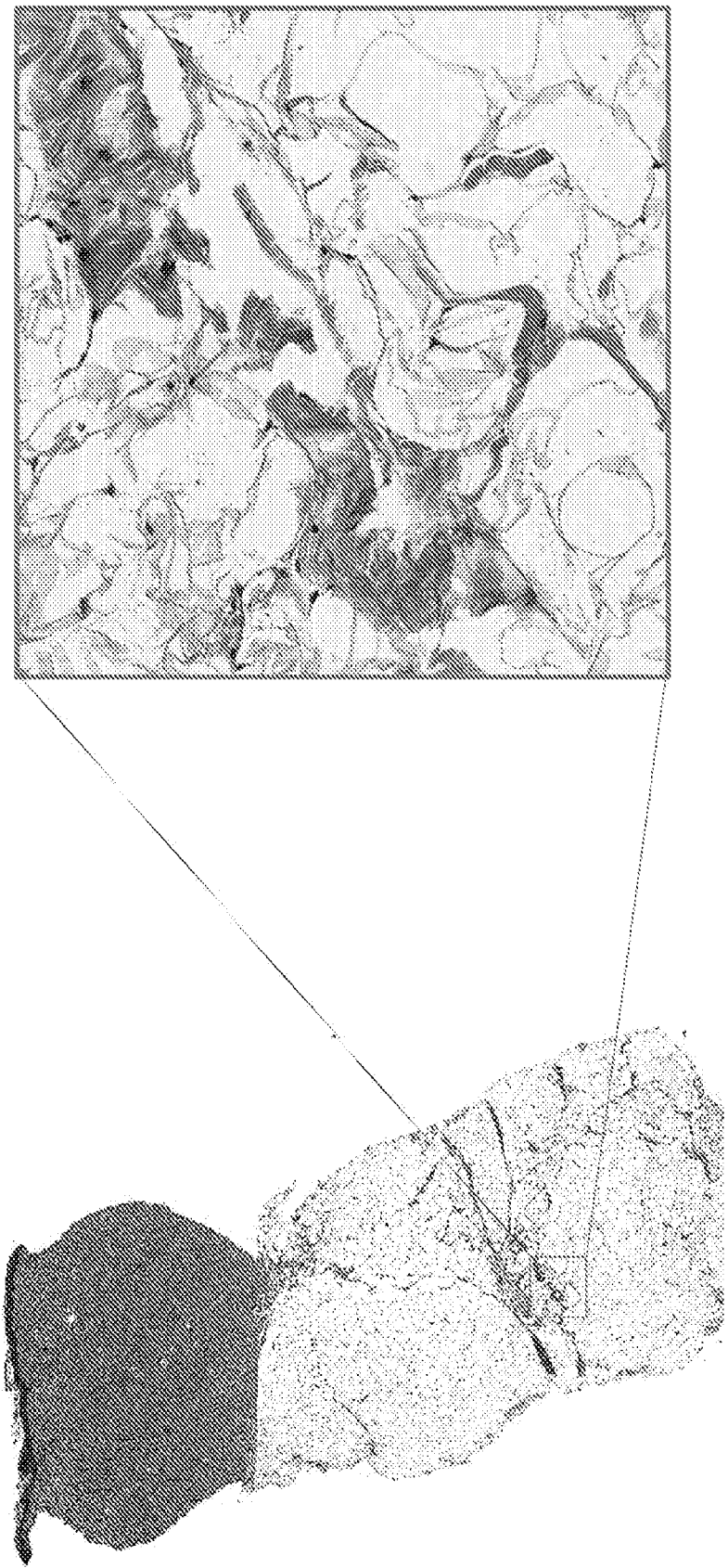
FIGS. 24A and 24B depict two photographs of a slide illustrating fibrous septa.

FIGS. 24A-26 provide histological images showing the disruption of tissue (e.g., fibrous septa) in the subcutaneous tissue at different times after treatment. Referring to FIG. 24A, FIG. 24A is a histological image at a 5× magnification showing the disruption of tissue (e.g., fibrous septa) in the subcutaneous tissue immediately after treatment. FIG. 24B is an enlarged histological image of a portion of the histological image of FIG. 24A showing the disruption of tissue (e.g., fibrous septa) in the subcutaneous tissue immediately after treatment in more detail.

Figure 25B:
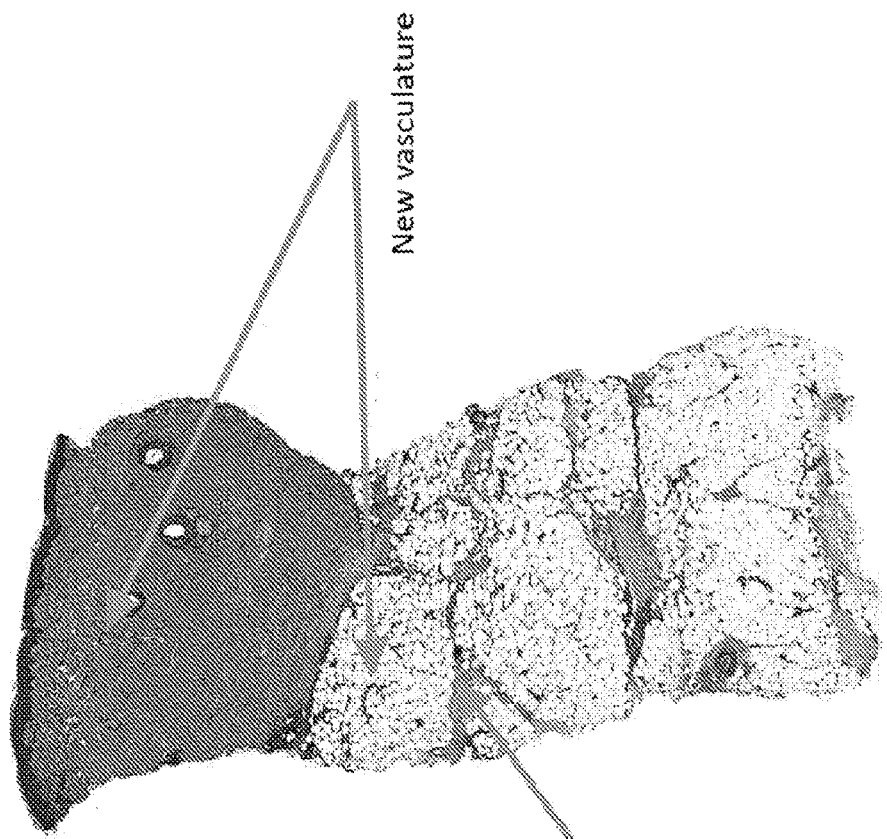
FIGS. 25A and 25B depict two photographs of slides illustrating comparisons of fibrous septa and new vasculature.
Figure 25A:
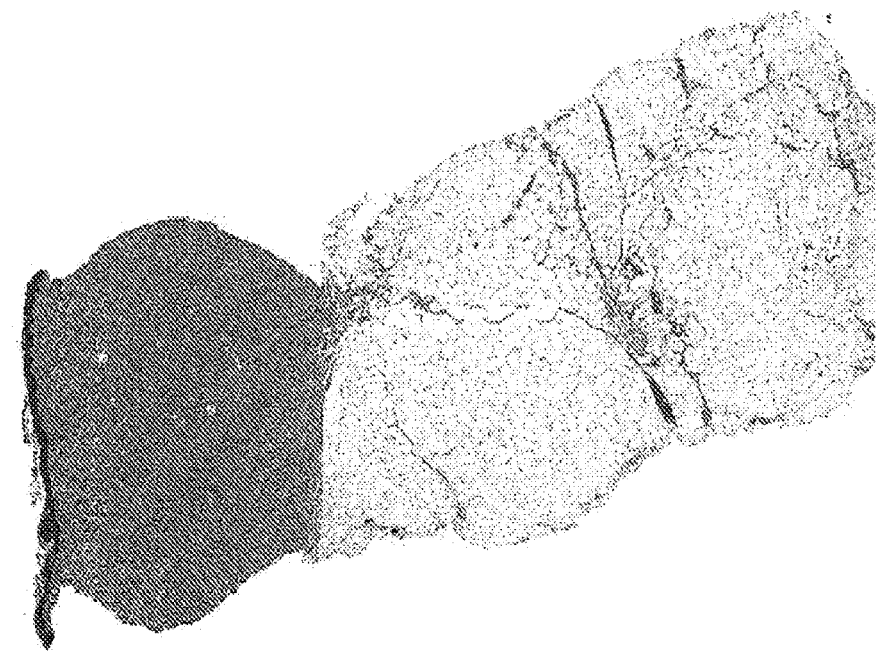

FIGS. 25A and 25B provide histological images at a 5× magnification that compares the tissue immediately post-treatment (FIG. 25A, similar to FIG. 24A) to the tissue 6-days post-treatment (FIG. 25B). As shown in FIG. 25B, the tissue at 6-days post-treatment has demonstrated a significant tissue reaction (e.g., vascularization), as compared to the tissue shown in FIG. 25A.

Figure 26:
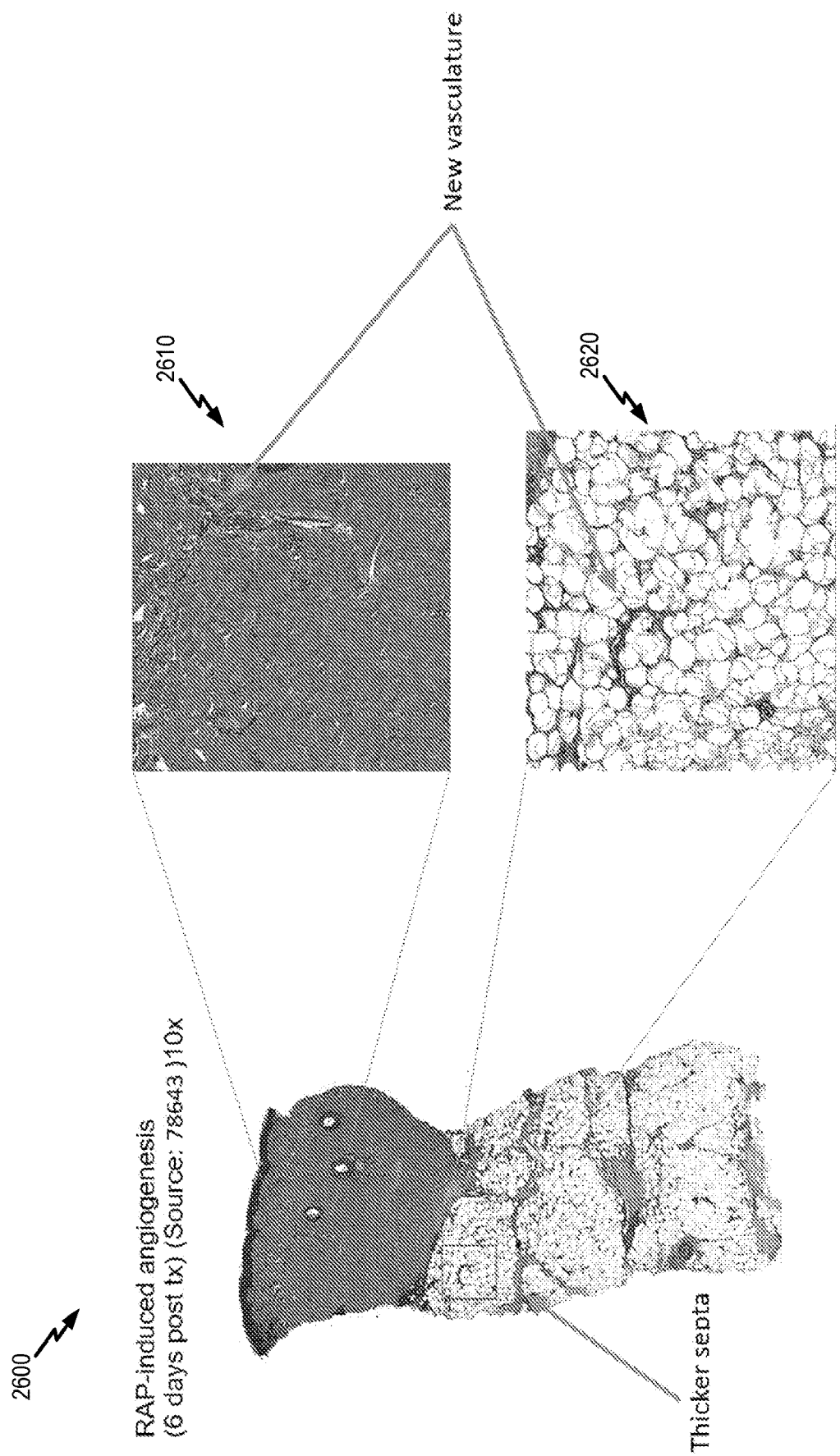
FIG. 26 depicts three photographs of a slide illustrating new vasculature of fibrous septa.

FIG. 26 provides detailed histological images of the tissue samples 6-days post-treatment illustrated in FIG. 25B. FIG. 26 includes a histological image 2600 at 10 times magnification of the tissue samples 6-days post-treatment similar to FIG. 25B. FIG. 26 further includes two further enlarged sections 2610 and 2620 illustrating dermis and subcutaneous tissue. Both the dermis illustrated in enlarged section 2610 and the subcutaneous tissue illustrated in enlarged section 2620 demonstrate significant tissue reaction in the form of thicker fibrous septa secondary to new collagen deposition and new vasculature. As can be seen from the close-up histology images (enlarged sections 2610 and 2620), both the adipocytes and the fibrous septa appear to have experienced disruption. There was no evidence of cavitation or thermal damage in the tissue.

The results of this study support the ability of the acoustic subcision device RAP to safely cause tissue disruption leading to a tissue reaction as demonstrated by induction of new collagen and new blood vessels in the dermis and subcutaneous fat tissue.

VI. Example 6

Inducing a Tissue Reaction by RAPs

Another study was undertaken using Gottingen Minipigs to evaluate inducing tissue reaction (e.g., vascularization) by physical disruption of tissue structures using non-non-cavitating) compressed RAPs, such as 200, 280 and 295. The same general procedure as outlined in Example 1 was followed. However, the RAPs had a mean peak output pressure of about 8-9 MPa, had a negative pulse component duration of under 2 microseconds, and were provided at a rate of 50 Hz for two minutes, similar to Example 5.

Figure 27B:
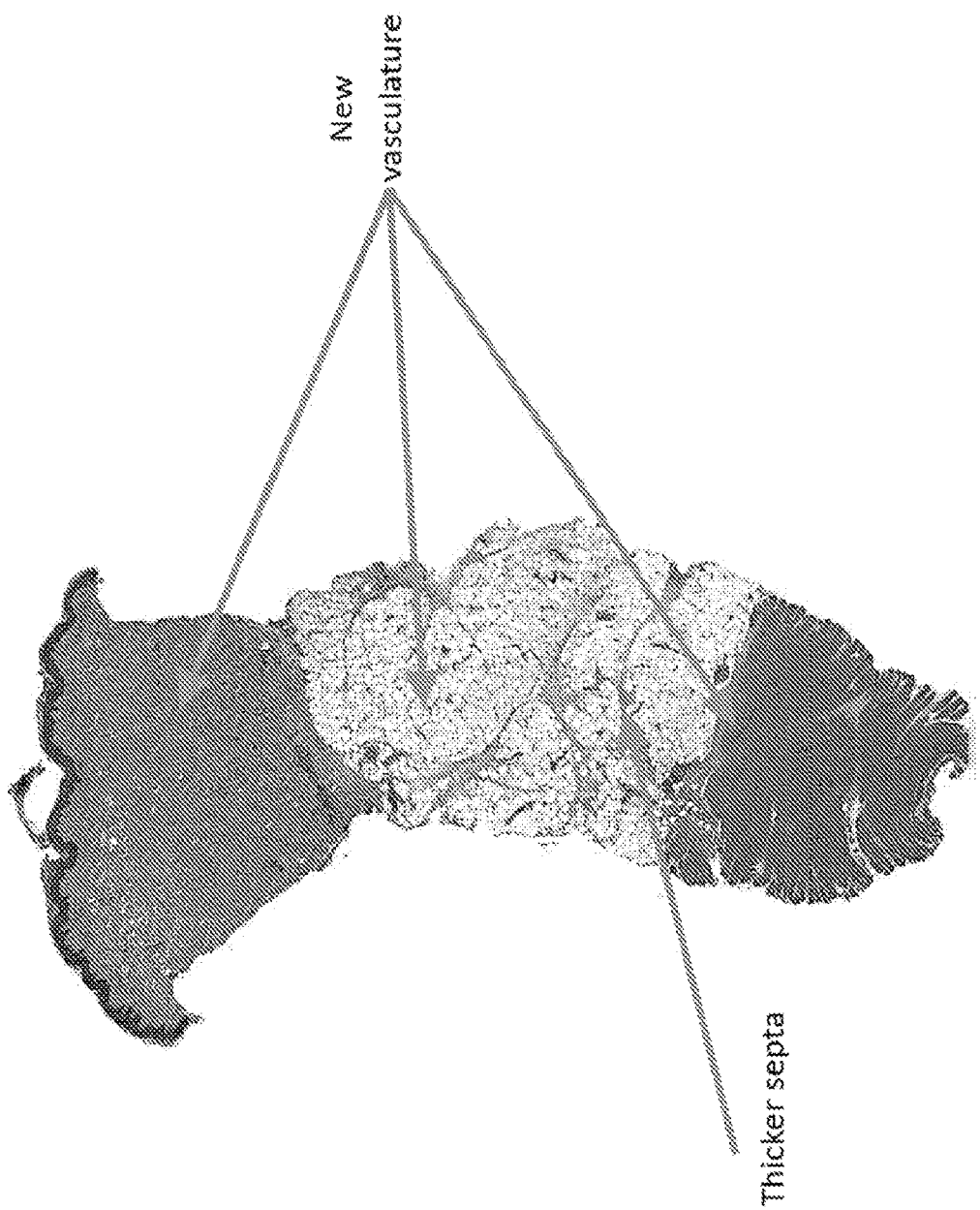
FIGS. 27A and 27B depict two photographs illustrating comparisons of fibrous septa and illustrating new vasculature.
Figure 27A:
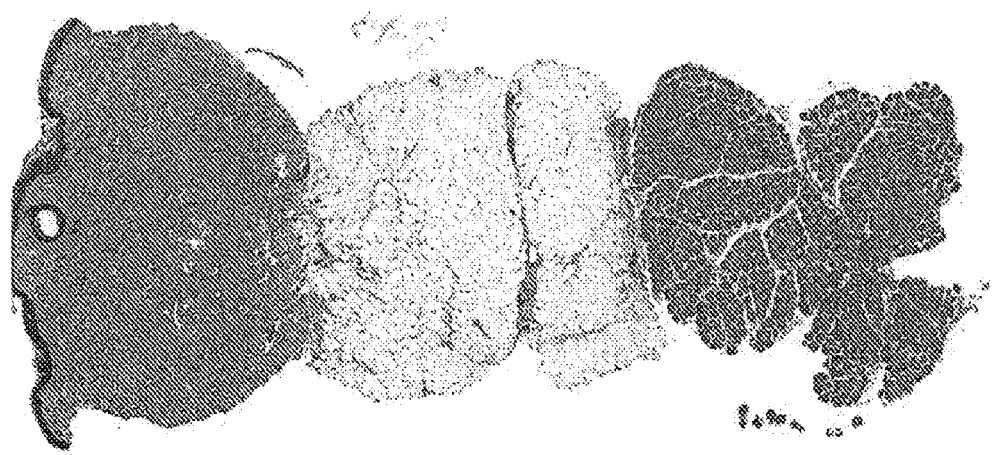

FIGS. 27A and 27B provide histological images at a 5× magnification showing the disruption of tissue (e.g., fibrous extracellular matrix) in the subcutaneous tissue immediately after treatment (FIG. 27A) to tissue from the same treatment site 6-days post-treatment (FIG. 27B). The tissue at 6-days post-treatment demonstrated a significant tissue reaction in the form of thicker fibrous septa from collagen deposition and new vasculature. There was no evidence of cavitation or thermal damage in the tissue.

Figure 28B:
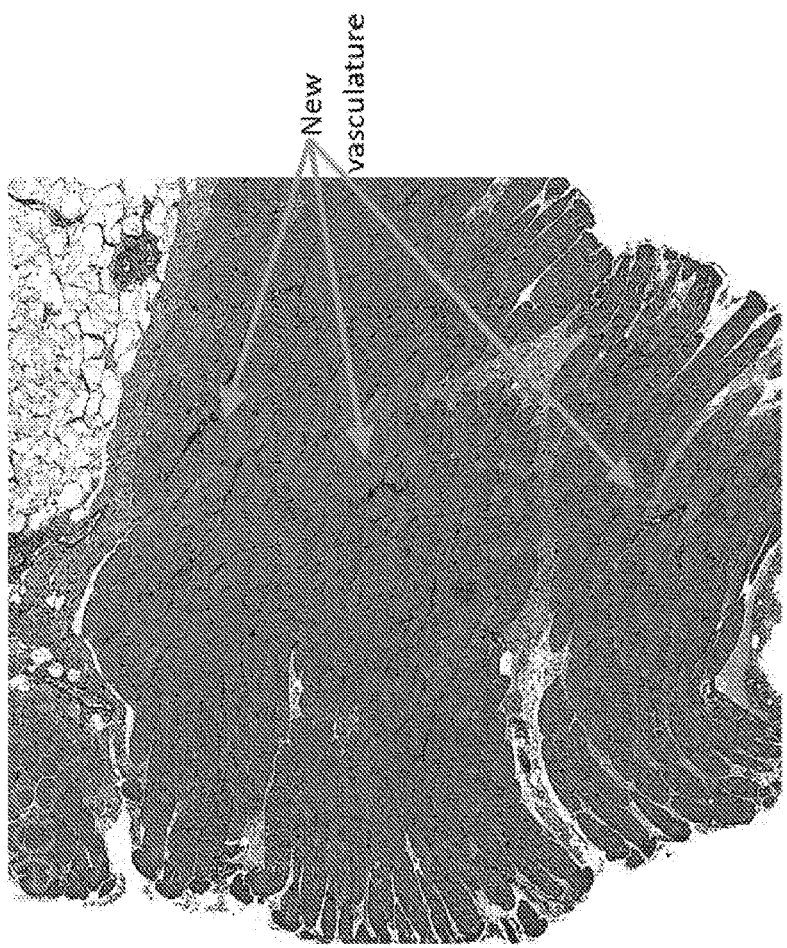
FIGS. 28A and 28B depict two photographs illustrating comparisons of fibrous septa and illustrating new vasculature in muscle.
Figure 28A:
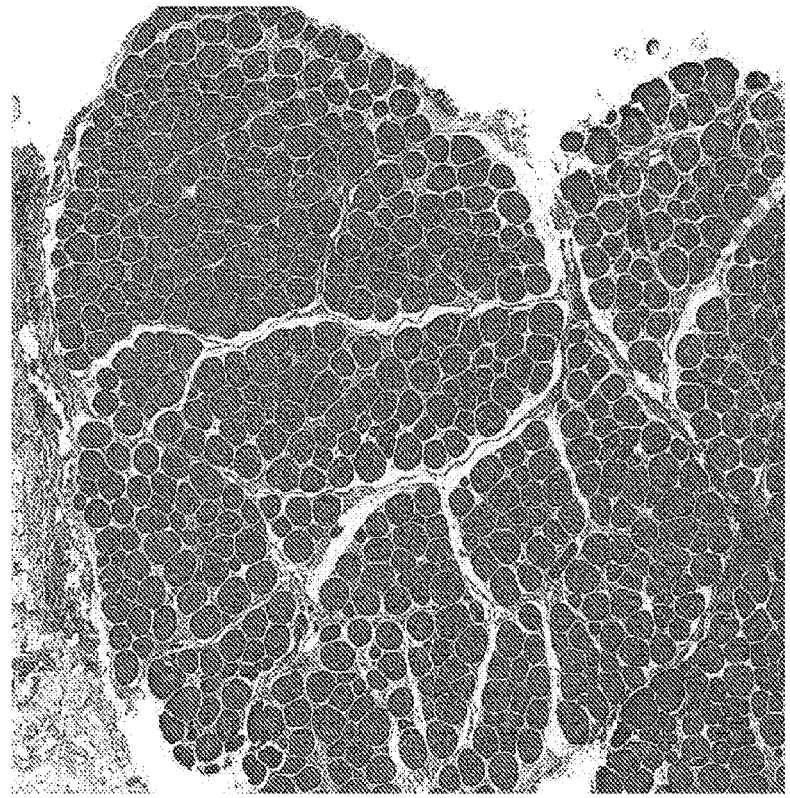

FIGS. 28A and 28B provides a close up histological images of muscle tissue from the day of treatment (FIG. 28A) and 6-days post-treatment (FIG. 28B). The muscle tissue 6-days post-treatment demonstrates significant tissue reaction in the form of increased vascularization.

The results of this study support the ability of the acoustic subcision device RAP to safely cause tissue disruption leading to a tissue reaction as demonstrated by induction of new collagen and new blood vessels in the dermis, subcutaneous fat tissue, and muscle tissue.

VII. Example 7

Inducing a Tissue Reaction by RAPs in Humans

In another study, a middle-age female subject, that was schedule to undergo an abdominoplasty, was treated with acoustic subcision to evaluate inducing physical disruption of the dermal extracellular matrix tissue structures using RAP. A treatment site and a control site were defined and marked with a pen. With no anesthesia, the acoustic subcision device provided RAP to the treatment site. The RAPs provided by the acoustic subcision device had a mean peak output pressure of about 4-6 MPa and were provided at a rate of 50 Hz for about 2 minutes per each 10 cm$^2$ area. In addition, the RAPs had a negative pulse component duration of under 2 microseconds. The participant reported no discomfort during the RAP application.

Four-days post-treatment, the participant underwent the abdominoplasty on the control site. After the surgical procedure, the treatment site and control site areas on the excised skin were biopsied using 3 mm circular punch biopsy instruments. The tissue samples were placed in buffered formalin. Histological slides of the tissue samples were stained with H&E for microscopic examination.

Figure 29B:
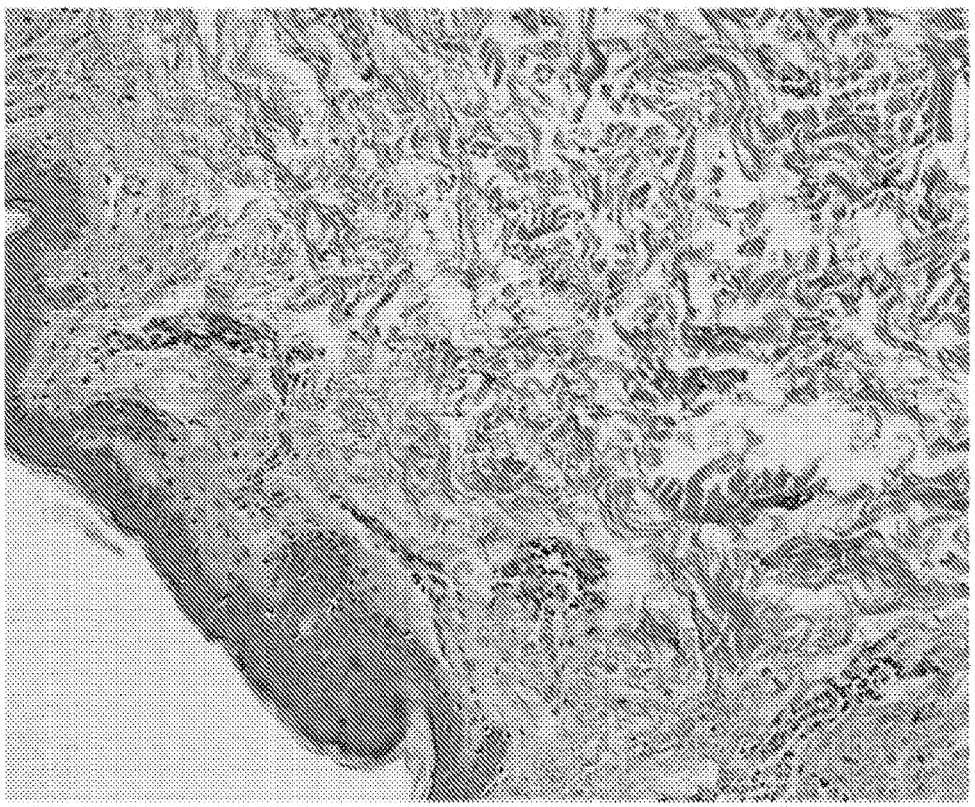
FIGS. 29A and 29B depict two photographs illustrating comparisons of dermal collagen.
Figure 29A:
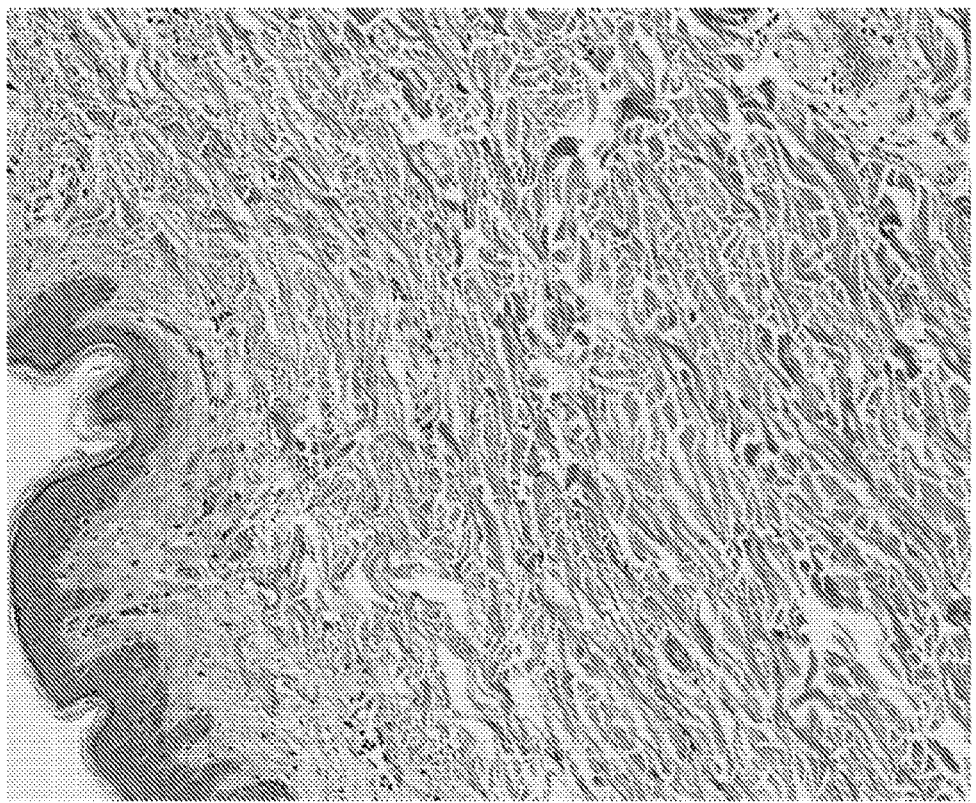

FIGS. 29A and 29B provide histological images at a 10× magnification of the tissue 4-days post-treatment for the control site (FIG. 29A) and treatment site (FIG. 29B). As can be seen, in comparison to the control site tissue in FIG. 29A, the treatment site tissue in FIG. 29B demonstrates marked tissue disruption. There was no evidence of cavitation or thermal damage in the tissue of the treatment site (FIG. 29B).

Figure 30B:
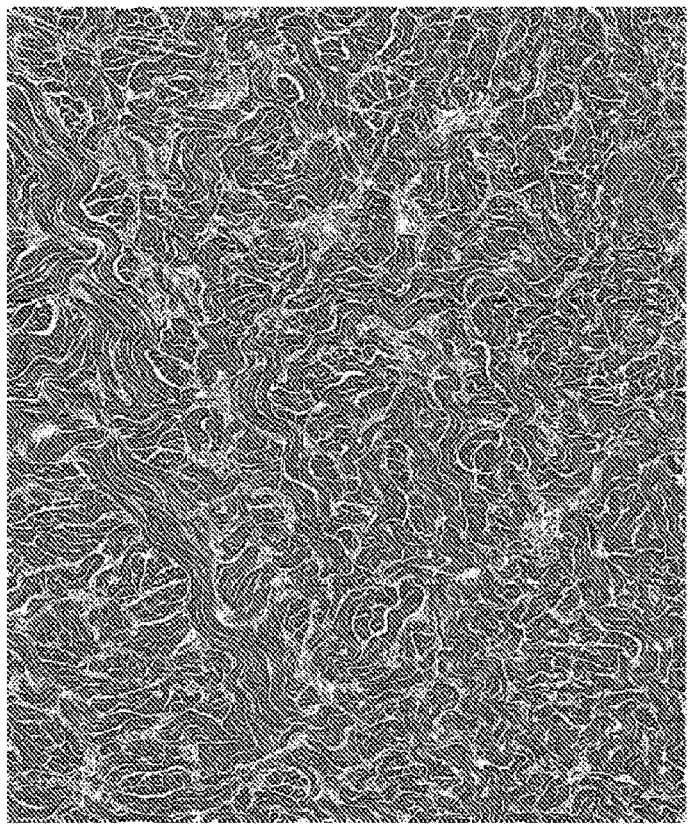
FIGS. 30A and 30B depict two photographs illustrating comparisons of dermal collagen.
Figure 30A:
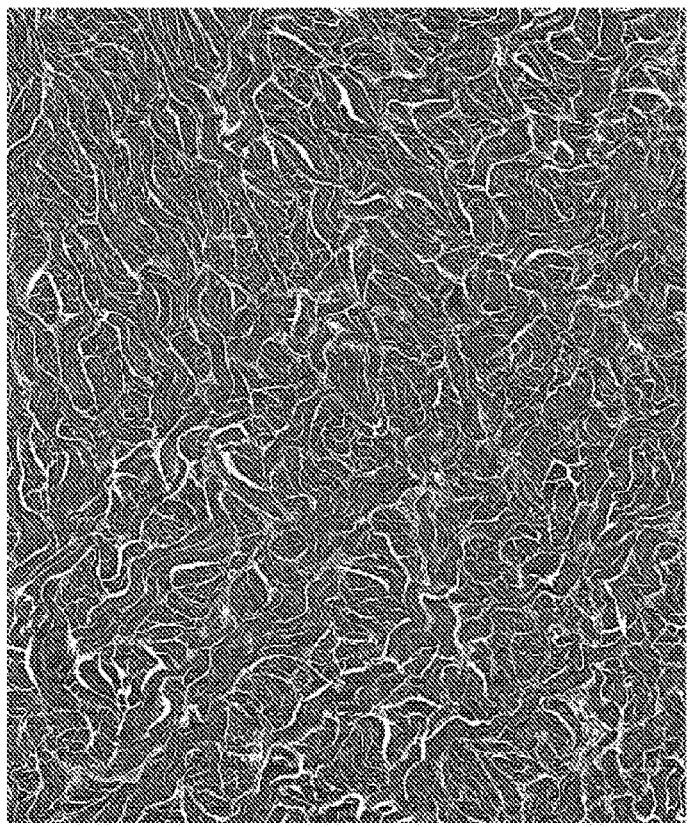

In similar animal studies, the disrupted dermal tissue induces a tissue reaction as demonstrated by increase in new collagen (collagenesis) at 62-days post treatment as shown in FIG. 30A (Day 0) and 30B (Day 62). The slides shown in FIGS. 30A and 30B are at 8× magnification and illustrate that new collagen (blue when stained) has developed over the 62 days after the treatment.

The results of this study once again support the ability of unfocused, non-cavitating, rapid pulse acoustic shock waves to safely cause a disruption in tissue (i.e., dermis) structure with no evidence of cavitation or thermal damage. Furthermore, the disrupted tissue induces a tissue reaction as demonstrated by increase in new collagen in the dermis.

The results of the studies of Examples 5-7 support the ability of the acoustic subcision device RAP to safely cause tissue disruption leading to a tissue reaction, such as vascularization and/or dermal collagenesis.

Example 8

Treating Human Scar Tissue Using RAP

Another study was performed to evaluate inducing a reduction of the fibrotic scar using acoustic subcision, a middle-age female subject with a fibrotic scar at a site of an older healed caesarian section incision was treated with RAP. The treatment site was marked with a pen and baseline 3-D photographs were taken using an Antera 3D camera (Miravex). With no anesthesia, the acoustic subcision device provided RAP to a hydrogel covered treatment site. The RAPs provided by the acoustic subcision device had a mean peak output pressure of about 4-6 MPa and were provided at a rate of 50 Hz for about 6 minutes to the fibrotic scar site. In addition, the RAPs had a negative pulse component duration of under 2 microseconds. The participant reported no discomfort during the RAP application.

Six-weeks following the treatment of the subject, 3-D photographs were once again taken of the treated fibrotic scar site. The results showed that the volume of the fibrotic scar had decreased by about 7% and the height of the fibrotic scar had decreased by about 29%.

The results of the studies support the ability of the acoustic subcision device to safely cause tissue disruption leading to a tissue reaction, such as a reduction in fibrotic scar tissue.

Example 9

Reduction of Fibrotic Scars Using RAP

A single-site proof of concept IRB approved human clinical study was performed to evaluate the safety, tolerability, and efficacy of the RAP device for the temporary improvement in the appearance of fibrotic scars. The RAP device produces high intensity acoustic shock waves at a rapid rate of 50 pulses per second and is capable disrupting dermal fibrous structures and subdermal fibrous structures. It has the potential to improve the appearance of scars through both micro-disruption of the scar tissue matrix and down-regulation of fibrotic fibroblasts leading to scar remodeling. The RAP device has been successfully used in two IRB-approved human clinical trials to accelerate laser-based tattoo removal, and in a proof of concept trial to improve the appearance of cellulite.

A single 6-minute RAP session was used to treat 11 fibrotic scars (i.e., keloid or hypertrophic scars) in 10 participants. Immediately post treatment, unexpected adverse events (UAEs) and treatment tolerability were recorded. Assessment of scar dimensions and appearance was performed using before and after photos taken with a 3-dimensional multispectral camera (Antera 3D Pro, Miravex, Dublin, Ireland). Images acquired with the Antera 3D Pro were analyzed using proprietary software for changes in scar volume and height from pretreatment to the 12 week followup. At the 12 week followup, participants were asked to fill out a "patient satisfaction" survey.

3D scar assessment of the pre- and post-treatment photographs of 11 treated scars demonstrated an average reduction in volume of 29.6% ($p<0.01$) (range 2% to −48%), and an average reduction in height of 14.6% ($p<0.005$) (range 0% to −34%). Except for mild erythema and pinpoint bleeding, no UAEs occurred from the RAP treatment. The treatment sessions were considered tolerable by all subjects. The average pain score was 2.2 (on a 0-10 pain score with 10 being the worse possible pain). Seven of 10 participants agreed or strongly agreed that the scar was improved, while two were neutral, and one disagreed. Eight of 10 agreed or strongly agreed that they would do the treatment again, while one was neutral, and one disagreed. Finally, six of 10 agreed or strongly agreed that they would recommend the treatment to a friend, while three were neutral, and one disagreed.

The treatment of fibrotic scars using the RAP device is safe and tolerable. Follow up at 12 weeks demonstrates that RAP provides significant improvements in the appearance of fibrotic scars from a single short duration, noninvasive treatment, with minimal pain, and most patients express satisfaction with the amount of progress. The dermal The claims are not intended to include, and should not be interpreted to include, means-plus- or step-plus-function limitations, unless such a limitation is explicitly recited in a given claim using the phrase(s) "means for" or "step for," respectively.

REFERENCES

[1] Amore, R., Amuso, D., Leonardi, V., Sbarbati, A., & et al. (2018, May 18). Treatment of dimpling from cellulite. *Plast Reconstr Surg Glob Open*, 1-8.
[2] Bae, S. (2017, 5). Antifibrotic Effects of Vibratory Stimulation. *All Dissertations/*1879. Clemson University TigerPrints.
[3] Chandrashekar, B. S., & Nandini, A. S. (2010, May-August). Acne Scar Subcision. *J Cutan Aesthet Surg.*, 3(2), 126-126.
[4] Chiquet, M., Renedo, A. S., Huber, F., & Flück, M. (2003). How do fibroblasts translate mechanical signals into changes in extracellular matrix production? *Matrix Biology*, 22, 73-80.
[5] Freund, J. B., Colonius, T., & Evan, A. P. (2007, September). A cumulative shear mechanism for tissue damage initiation in shock-wave lithotripsy. *Ultrasound Med Biol.*, 33(9), 1495-1503.
[6] Howard, D., & Sturtevant, B. (1997). In vitro study of the mechanical effects of shock-wave lithotripsy. *Ultrasound in Med. & Biol.*, 23(7), 1017-1122.
[7] Jookaki, H., & Panzer, M. V. (2018). Skin mechanical properties and modeling: A review. *Proc IMechE Part H: J Engineering in Medicine*.
[8] Kaminer, M. S., Coleman, W. P., Weiss, R. A., Robinson, D. M., Coleman, W. P., & Hornfeld, C. (2015,March). Multicenter pivotal study of vacuum-assisted precise tissue release for the treatment of cellulite. *American Soc of Derm Surg*, 41(3).
[8] Marinkovic, A., Liu, F., & Tshumperlin, D. J. (2013). Matrices of physiologic stiffness potently Inactivate idiopathic pulmonary fibrosis fibroblasts. *Am. J. Respir. Cell Mol. Biol*, 48, 422-430.
[9] Wang, J. H.-C., Thampatty, B. P., Lin, J.-S., & Im, H.-J. (2007, Apr. 15). Mechanoregulation of gene expression in fibroblasts, *Gene*. 2007, Apr. 15; 391(1-2): 1-15., 391(1-2).
[10] Widgerow, A. D. (2011). Cellular/extracellular matrix cross-talk in scar evolution and control. *Wound Rep Reg* (2011), 19, 117-133.

The invention claimed is:

1. An acoustic subcision device configured to cause disruption of fibrous structures using rapid acoustic pulses, the acoustic subcision device comprising:
   a housing;
   a pulse generation system coupled to the housing; and
   a controller coupled to the pulse generation system and configured to cause the pulse generation system to generate shockwave pulses, wherein the shockwave pulses are configured to cause disruption of fibrous adipose septa, and wherein the controller is configured to generate shockwave pulses that are compressed shockwave pulses having:
      a positive pulse component; and
      a negative pulse component,
      wherein the negative pulse component has a duration of less than 2 microseconds.

2. The acoustic subcision device of claim 1, wherein each acoustic wavefront of the shockwave pulses has a rise time of less than 500 ns and is directed to a depth at which there is adipose tissue.

3. The acoustic subcision device of claim 1, wherein each acoustic wavefront of the shockwave pulses is substantially planar.

4. The acoustic subcision device of claim 1, wherein the acoustic subcision device is configured to output the shockwave pulses at a pulse repetition rate of greater than 20 Hz.

5. The acoustic subcision device of claim 1, further comprising a vacuum head configured to generate negative pressure at a treatment site.

6. The acoustic subcision device of claim 5, further comprising:
a valve;
a motor coupled to the valve and configured to adjust the valve;
an indicator configured to output an indication corresponding to a position of the valve; and
a conduit coupled to the controller and to the vacuum head;
wherein the controller configured to send control signals to the motor and the indicator.

7. The acoustic subcision device of claim 6, wherein the vacuum head includes:
a vacuum head housing defining a window and one or more ports;
a compliant member coupled to the vacuum head housing;
one or more sensors coupled to the vacuum head housing; and
one or more lights coupled to the vacuum head housing.

8. A method of treating a patient to improve an appearance of cellulite using an acoustic subcision device, the method comprising:
positioning an acoustic subcision device that is configured to emit shockwave pulses proximate to a treatment site, wherein a controller of the subcision device is configured to generate shockwave pulses that are compressed shockwave pulses comprising:
a positive pulse component; and
a negative pulse component,
wherein the negative pulse component has a duration of less than 2 microseconds; and
applying a plurality of shockwaves to a treatment location of the treatment site until a fibrous adipose septa within the treatment site is ruptured, wherein the plurality of shockwaves comprise compressed shockwave pulses.

9. The method of claim 8, further comprising:
repositioning the acoustic subcision device to a second treatment location of the treatment site;
applying a second plurality of shockwaves to the second treatment location until a second fibrous adipose septa within the second treatment location is ruptured.

10. The method of claim 9, further comprising adjusting one of applied intensity, rate of wave pulses, wave form shape, or duration of exposure to the shockwaves before applying the second plurality of shockwaves to the second treatment location.

11. The method of claim 9, further comprising locating a dermal ridge or dimple within the treatment site, and wherein multiple shockwaves are applied to the dermal ridge or dimple.

12. The method of claim 9, wherein a treatment duration for the treatment location of the treatment site is one minute.

13. The method of claim 9, wherein the plurality of shockwaves correspond to unfocused and non-cavitating shockwaves.

14. The method of claim 9, wherein the shockwave pulses are substantially planar shockwaves.

15. The method of claim 9, wherein the plurality of shockwaves have a peak output pressure of 6 MPa and a pulse repetition rate of 100 Hz.

16. The method of claim 9, further comprising:
positioning a vacuum head on the treatment site;
applying the vacuum head to the treatment site; and
generating negative pressure at the treatment site.

17. A method of treating a patient to improve an appearance of cellulite by causing disruption to fibrous structures using rapid acoustic pulses, the method comprising:
identifying a treatment site including cellulite or a dimple; and
positioning a head of an acoustic subcision device at a first location on an epidermal layer of the treatment site, wherein a controller of the subcision device is configured to generate shockwave pulses that are compressed shockwave pulses comprising:
a positive pulse component; and
a negative pulse component;
wherein the negative pulse component has a duration of less than 2 microseconds;
directing a plurality of shockwaves to a subcutaneous layer of the treatment site at the first location, wherein the plurality of shockwaves comprise compressed shockwave pulses; and
rupturing one or more sclerotic fibrous adipose septa within the subcutaneous layer of the treatment site at the first location.

18. The method of claim 17, further comprising:
evaluating a grade of the cellulite at the treatment site;
based on the grade, determining a peak pressure and a pulse repetition rate of the plurality of shockwaves and a treatment time;
directing the plurality of shockwaves at the determined peak pressure and pulse repetition rate for the determined treatment time to rupture the one or more sclerotic fibrous adipose septa.

19. The method of claim 18, wherein:
the grade of the cellulite is grade II or above;
the peak pressure is between approximately 5 and 10 MPa,
the pulse repetition rate is approximately 50 Hz,
the treatment time is approximately 2 minutes.

20. The method of claim 17, further comprising:
positioning the head of the acoustic subcision device at a second, third, fourth, and fifth location on the epidermal layer of the treatment site; and
for each of the second, third, fourth, and fifth locations:
directing the plurality of shockwaves to the subcutaneous layer of the treatment site at the location; and
rupturing one or more sclerotic fibrous adipose septa within the subcutaneous layer of the treatment site at the location.

* * * * *